US011111542B2

(12) United States Patent
Wang et al.

(10) Patent No.: US 11,111,542 B2
(45) Date of Patent: Sep. 7, 2021

(54) METHOD FOR IDENTIFYING HIGH-RISK AML PATIENTS

(71) Applicant: UNIVERSITY HEALTH NETWORK, Toronto (CA)

(72) Inventors: Jean Wang, Toronto (CA); John Dick, Toronto (CA); Stanley Ng, Toronto (CA); Mark Minden, Toronto (CA); Amanda Mitchell, Toronto (CA); Weihsu Chen, Toronto (CA); Peter Zandstra, Toronto (CA); James Kennedy, Jamaica Plain, MA (US)

(73) Assignee: UNIVERSITY HEALTH NETWORK, Toronto (CA)

( * ) Notice: Subject to any disclaimer, the term of this patent is extended or adjusted under 35 U.S.C. 154(b) by 0 days.

(21) Appl. No.: 16/075,808

(22) PCT Filed: Feb. 6, 2017

(86) PCT No.: PCT/CA2017/000025
§ 371 (c)(1),
(2) Date: Aug. 6, 2018

(87) PCT Pub. No.: WO2017/132749
PCT Pub. Date: Aug. 10, 2017

(65) Prior Publication Data
US 2019/0300956 A1    Oct. 3, 2019

Related U.S. Application Data

(60) Provisional application No. 62/292,254, filed on Feb. 6, 2016, provisional application No. 62/348,365, filed on Jun. 10, 2016, provisional application No. 62/426,300, filed on Nov. 24, 2016, provisional application No. 62/429,205, filed on Dec. 2, 2016.

(51) Int. Cl.
| *C12Q 1/6883* | (2018.01) |
| *C12Q 1/6851* | (2018.01) |
| *C12Q 1/6874* | (2018.01) |
| *G01N 33/574* | (2006.01) |
| *G16B 25/10* | (2019.01) |
| *G16B 25/20* | (2019.01) |
| *G16B 25/00* | (2019.01) |
| *G16B 99/00* | (2019.01) |
| *C40B 40/06* | (2006.01) |
| *C40B 40/08* | (2006.01) |

(52) U.S. Cl.
CPC ......... *C12Q 1/6883* (2013.01); *C12Q 1/6851* (2013.01); *C12Q 1/6874* (2013.01); *C40B 40/06* (2013.01); *C40B 40/08* (2013.01); *G01N 33/57426* (2013.01); *G16B 25/00* (2019.02); *G16B 25/10* (2019.02); *G16B 25/20* (2019.02); *G16B 99/00* (2019.02); *C12Q 2600/106* (2013.01); *C12Q 2600/118* (2013.01); *C12Q 2600/158* (2013.01); *G01N 2800/52* (2013.01); *G01N 2800/60* (2013.01)

(58) Field of Classification Search
None
See application file for complete search history.

(56) References Cited

U.S. PATENT DOCUMENTS

| 7,474,767 B2 | 1/2009 | Sen et al. | |
| 2001/0051344 A1* | 12/2001 | Shalon | B82Y 30/00 435/6.11 |

FOREIGN PATENT DOCUMENTS

| EP | 2458014 | 5/2012 |
| WO | WO 2005/043164 | 5/2005 |
| WO | WO 2005/045434 | 5/2005 |
| WO | WO 2005/080601 | 9/2005 |
| WO | WO 2007/037611 | 4/2007 |

OTHER PUBLICATIONS

Cobb et al (Crit Care Med 2002 vol. 30 p. 2711) (Year: 2002).*
Lucentini (The Scientist, 2004, vol. 18, p. 20) (Year: 2004).*
Enard et al. (Science 2002 vol. 296 p. 340) (Year: 2002).*
Alibhai, et al., "Outcomes and Quality of Care in Acute Myeloid Leukemia Over 40 Years," *Cancer*, 115(13);2903-2911, 2009.
Altschul, et al., "Basic Local Alignment Search Tool," *Journal of Molecular Biology*, 215(3); 403-410, 1990.
Brandwein, et al., Predictors of Response to Reinduction Chemotherapy for Patients with Acute Myeloid Leukemia Who Do not Achieve Complete Remission with Frontline Induction Chemotherapy, *American Journal of Hematology*, 83; 54-58, 2008.
Castaigne, et al., "Effect of Gemtuzumab Ozogamicin on Survival of Adult Patients with De-Novo Acute Myeloid Leukaemia (ALFA-0701): A Randomised, Open-Label, Phase 3 Study," *Lancet*, 379(9825); p. 1508-p. 1516, 2012.
Chen, et al., "An Integrated Analysis of Heterogeneous Drug Responses in Acute Myeloid Leukemia that Enables the Discovery of Predictive Biomarkers," *Cancer Research*, 76(5); 987-1297. (in press), 2016.

(Continued)

*Primary Examiner* — Katherine D Salmon
(74) *Attorney, Agent, or Firm* — Norton Rose Fulbright US LLP

(57) ABSTRACT

There is described herein a method of prognosing or classifying a subject with acute myeloid leukemia (AML) comprising: (a) determining the expression level of at least 3 genes in a test sample from the subject selected from the group consisting of DNMT3B, ZBTB46, NYNRIN, ARHGAP22, LAPTM4B, MMRN1, DPYSL3, KIAAQ125. CDK6, CPXM1, SOCS2, SMIM24, EMP1, NGFRAP1, CD34, AKR1C3, GPR56; and (b) comparing expression of the at least 3 genes in the test sample with reference expression levels of the at least 3 genes from control samples from a cohort of patients; wherein a difference or similarity in the expression of the at least 3 genes in the test sample and the reference expression levels is used to prognose or classify the subject with AML into a low risk group or a high risk group for worse survival.

5 Claims, 33 Drawing Sheets
Specification includes a Sequence Listing.

(56) References Cited

OTHER PUBLICATIONS

Cheson, et al., "Revised Recommendations of the International Working Group for Diagnosis, Standardization of Response Criteria, Treatment Outcomes, and Reporting Standards for Therapeutic Trials in Acute Myeloid Leukemia," *Journal of Clinical Oncology*, 21: 4642-4647, 2003.
Dai, et al., Evolving gene/transcript definitions significantly alter the interpretation of GeneChip data. *Nucleic Acids Research*, 33; e175, 2005.
Dohner, et al., "Diagnosis and Management of Acute Myeloid Leukemia in Adults: Recommendations from an International Expert Panel, On Behalf of the European LeukemiaNet," *Blood*, 115(3); 453-474, 2010.
Du, et al., "lumi: a Pipeline for Processing Illlumina Microarray," *Bioinformatics*, 24(13);1547-1548, 2008.
Eppert, et al., "Stem Cell Gene Expression Programs Influence Clinical Outcome in Human Leukemia," *Nature Medicine*, 17; 1086-1093, 2011.
Ferrara & Schiffer, "Acute Myeloid Leukaemia in Adults," *Lancet*, 381; 484-495, 2013.
Fine & Gray, "A Proportional Hazards Model for the Subdistribution of a Competing Risk," *Journal of the American Statistical Association*, 94; 496-509, 1999.
Fong, et al., "BET Inhibitor Resistance Emerges from 5 Leukaemia Stem Cells," *Nature*, 525;538-542, 2015.
Friedman, et al., "Regularization Paths for Generalized Linear Models via Coordinate Descent," *Journal of Statistical Software*, 33;1-22, 2010.
Gautier, et al., "affy—analysis of Affymetrix GeneChip data at the probe level," *Bioinformatics*, 20; 307-315, 2004.
Geiss, et al.. "Direct Multiplexed Measurement of Gene Expression with Color-Coded Probe Pairs," *Nature Biotechnology*, 26; 317-325, 2008.
Gentles, et al., "Association of a Leukemic Stem Cell Gene Expression Signature with Clinical Outcomes in Acute Myeloid Leukemia," *Journal of the American Medical Association*, 304(24); 2706-2715, 2010.
Grimwade, et al., "Refinement of Cytogenetic Classification in Acute Myeloid Leukemia: Determination of Prognostic Significance of Rare Recurring Chromosomal Abnormalities Among 5876 Younger Adult Patients Treated in the United Kingdom Medical Research Council Trials," *Blood*, 116; 354-365, 2010.
Guzman, et al., The Sesquiterpene Lactone Parthnolide Induces Apoptosis of Human Acute Myelogenous Leukemia Stem and Progenitor Cells, *Blood*, 105(11); 4163-4169, 2005.
Hills, et al., "Addition of Gemtuzumab Ozogamicin to Induction Chemotherapy in Adult Patient with Acute Myeloid Leukaemia: A Meta-Analysis of Individual Patient Data from Randomised Controlled Trials," *Lancet Oncology*, 15(9); p. 986-p. 966, 2014.
How, et al., "Influence of FL T3-Internal Tandem Duplication Allele Burden and White Blood Cell Count on the Outcome in Patients with Intermediate Risk Karyotype Acute Myeloid Leukemia," *Cancer*, 118(24); 6110-6117, 2012.
Illumina, Inc. "HumanHT-12 v4 Beadchip", Datasheet, retrieved Apr. 10, 2017 from the Internet: https://www.illumina.com/content/dam/illuminatmarketing/documents/products/product_information_sheets/product_info_humanht-12.pdf.
International Search Report and Written Opinion Issued in Corresponding PCT Application No. PCT/CA2017/000025, dated Apr. 25, 2017.
Ivey, et al., "Assessment of Minimal Residual Disease in Standard-Risk AML," *New England Journal of Medicine*, 374; 422-433, 2016.
Jin, et al., "Monoclonal Antibody-Mediated Targeting of CD123, IL-3 Receptor Alpha Chain, Eliminates Human Acute Myeloid Leukemic Stem Cells," *Cell Stem Cell*, 5; 31-42, 2009.
Jin, et al., Targeting of CD44 Eradicates Human Acute Myeloid Leukemic Stem Cells, *Nature Medicine*, 12(10);1167-1174, 2006.

Jung, et al., "An LSC Epigenetic Signature is Largely Mutation Independent and Implicates the HOXA Cluster in AML Pathogenesis," *Nature Communications*, 6(Document 8489); 1-12, 2015.
Klein, et al., "Quantitative Comparison of Microarray Experiments with Published Leukemia Related Gene Expression Signatures," *BMC Bioinformatics*, 10; 422, 2009.
Kohlmann, et al., "Gene Expression Profiling in AML with Normal Karyotype Can Predict Mutations for Molecular Markers and Allows Novel Insights into Perturbed Biological Pathways," *Leukemia*, 24;1216-1220, 2010.
Kreso & Dick, "Evolution of the Cancer Stem Cell Model," *Cell Stem Cell*,14; 275-29, 2014.
Krivtsov, et al., "Cell of Origin Determines Clinically Relevant Subtypes of MLL-Rearranged AML," *Leukemia*, 27; 852-860, 2013.
Kundu, et al., "PredictABEL: An R Package for the Assessment of Risk Prediction Models," *European Journal of Epidemiology*, 26; 261-264, 2011.
Laurenti, "The Transcriptional Architecture of Early Human Hematopoiesis Identifies Multilevel Control of Lymphoid Commitment," *Nature Immunology*, 14(7); 756-763, 2013.
Laurenti, et al., "CDK6 Levels Regulate Quiescence Exit in Human Hematopoietic Stem Cells," *Cell Stem Cell*, 16; 302-313, 2015.
Lechman, et al., "miR-126 Regulates Distinct Self-Renewal Outcomes in Normal and Malignant Hematopoietic Stem Cells," *Cancer Cell*, 29(2); 214-228, 2016 (in press).
Levine, et al., "Data-Driven Phenotype Dissection of AML Reveals Progenitor-Like Cells that Correlate with Prognosis," *Cell*, 162; 184-197, 2015.
Li, et al., SIRT1 Activation by a C-MYC Oncogenic Network Promotes the Maintenance and Drug Resistance of Human FL T3-ITD Acute Myeloid Leukemia Stem Cells, *Cell Stem Cell*, 15; 431-446, 2014.
MacRae, et al., "RNASeq Reveals Spliceosome and Proteasome Genes as Most Consistent Transcripts in Human Cancer Cells," *PLoS One*, 8; e72884, 2013.
Metzeler, et al., "An 86-probe-set Gene Expression Signature Predicts Survival in Cytogenetically Normal Acute Myeloid Leukemia," *Blood*, 112; 4193-4201, 2008.
Milyavsky, et al., "A Distinctive DNA Damage Response in Human Hematopoietic Stem Cells Reveals an Apoptosis-Independent Role for p53 in Self Renewal," *Cell Stem Cell*, 7; 186-197, 2010.
Ng, et al., "A 17-Gene Stemness Score for Rapid Determination of Risk in Acute Leukemia," *Nature*, 540; 433-437, 2016.
Nielsen, et al., "Analytical Validation of the PAM50-Based Prosigna Breast Cancer Prognostic Gene Signature Assay and nCounter Analysis System Using Formalin-Fixed Paraffin-Embedded Breast Tumor Specimens," *BMC Cancer*, 14; 177, 2014.
Notta, et al., "Isolation of Single Human Hematopoietic Stem Cells Capable of Long-Term Multilineage Engraftment," *Science*, 333; 218-221, 2011.
Novershtern, et al., "Densely Interconnected Transcriptional Circuits Control Cell States in Cell Human Hematopoiesis," *Cell*, 144; 296-309, 2011.
Papaemmanuil, et al., "Genomic Classification and Prognosis in Acute Myeloid Leukemia," *New England Journal of Medicine*, 374; 2209-2221, 2016.
Pearce, et al., "AML Engraftment in the NOD/SCIO Assay Reflects the Outcome of AML: Implications for Our Understanding ofthe Heterogeneity of AML," *Blood*, 107;1166-1173, 2006.
Qiao, et al., "PERT: A Method for Expression Deconvolution of Human Blood Samples from Varied Microenvironmental and Developmental Conditions," *PLoS Computational Biology*, 8: e1002838, 2012.
Ritchie, et al., "limma powers Differential Expression Analyses for RNA-Sequencing and Microarray Studies," *Nucleic Acids Research*, 43;e47, 2015.
Robin, et al., "pROC: An Open-Source Package for R and S+ to Analyze and Compare ROC Curves," *BMC Bioinformatics*, 12; 77, 2011.
Rollig, et al., "Long-Term Prognosis of Acute Myeloid Leukemia According to the New Genetic Risk Classification of the European

(56) References Cited

OTHER PUBLICATIONS

LeukemiaNet Recommendations: Evaluation of the Proposed Reporting System," *Journal of Clinical Oncology*, 29(20);2758 2765, 2011.

Saito, et al., Identification of Therapeutic Targets for Quiescent, Chemotherapy-Resistant Human Leukemia Stem Cells, *Science Translational Medicine*, 2(17); 17ra9, 2010.

Sarry, et al., "Human acute Myelogenous Leukemia Stem Cells are Rare and Heterogeneous When Assayed in NOD/SCID/IL2Ryc-Deficient Mice," *Journal of Clinical Investigation*, 121(1);384-395, 2011.

Schenk, et al., "Inhibition of the LSD1 (KDM1A) Demethylase Reactivates the All-Trans-Retinoic Acid Differentiation Pathway in Acute Myeloid Leukemia," *Nature Medicine*, 18(4); 605-611, 2012.

Scott, et al., Determining Cell-of-Origin Subtypes of Diffuse Large B-Cell Lymphoma Using Gene Expression in Formalin-Fixed Paraffin Embedded Tissue, *Blood*, 123(8):1214-1217, 2014.

Simon, et al., "Regularization Paths for Cox's Proportional Hazards Model via Coordinate Descent," *Journal of Statistical Software*, 39; 1-13, 2011.

The Cancer Genome Atlas Research Network, "Genomic and Epigenomic Landscapes of Adult de Nova Acute Myeloid Leukemia," *New England Journal of Medicine*, 368; 2059-2074, 2013.

Valk, et al., "Prognostically Useful Gene-Expression Profiles in Acute Myeloid Leukemia," *New England Journal of Medicine*, 350; 1617-1628, 2004.

Van Galen, et al., "The Unfolded Protein Response Governs Integrity of the Haematopoietic Stem Cell Pool During Stress," *Nature*, 510; 268-272, 2014.

Verhaak, et al., "Prediction of Molecular Subtypes in Acute Myeloid Leukemia Based on Gene Expression Profiling," *Haematologica*, 94:131-134, 2009.

Walter, et al., "Number of Courses of Induction Therapy Independently Predicts Outcome After Allogeneic Transplantation for Acute Myeloid Leukemia in First Morphological Remission," *Biology of Bone and Marrow Transplantation*, 21(2); 373-378, 2015.

Walter, et al., "Resistance Prediction in AML: Analysis of 4601 Patients from MRC/NCRI, HOVON/SAKK, SWOG and MD Anderson Cancer," *Leukemia*, 29; 312-320, 2015.

Hayette et al., "High DNA Methyltransferase DNMT38 Levels: A Poor Prognostic Marker in Acute Myeloid Leukemia" *PLOS One* 2012, 7(12), 10 pages.

Niederwieser et al., "Prognostic and biologic significance of DNMT3B expression in older patients with cytogenetically normal primary acute myeloid leukemia" *Leukemia* 2015, 29(3), 24 pages.

Partial Supplementary European Search Report issued in corresponding European application No. 17746659.6, dated Sep. 2, 2019.

* cited by examiner

FIG. 12G Optimized induction response sub-signature (PM AML testing subset)

FIG. 12H  Optimized induction response sub-signature (PM AML testing subset)
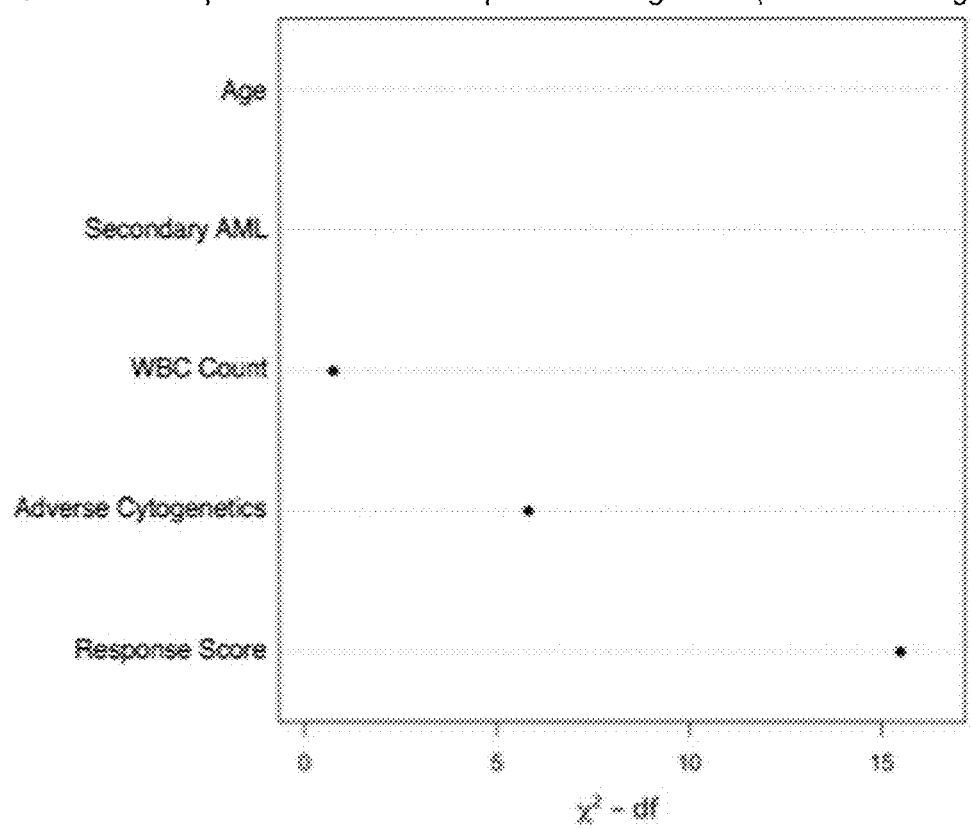
FIG. 13
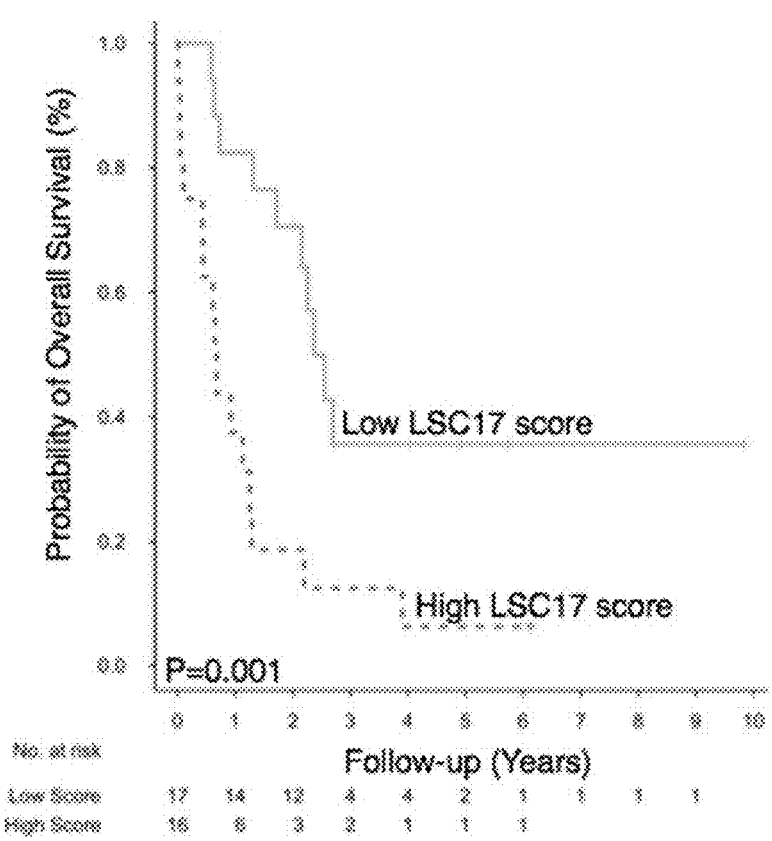

SEQUENCE LISTING

<160> NUMBER OF SEQ ID NOS: 29

<210> SEQ ID NO 1
<211> LENGTH: 100
<212> TYPE: DNA
<213> ORGANISM: Artificial Sequence
<220> FEATURE:
<223> OTHER INFORMATION: probe for AKR1C3

<400> SEQUENCE: 1
agaggacgtc tctatgccgg tgactggaca tatcacctct acttaaatcc gtcctgttta    60
gcgacttcag tcaactacag ctgagtccat aggccagaaa                          100

<210> SEQ ID NO 2
<211> LENGTH: 100
<212> TYPE: DNA
<213> ORGANISM: Artificial Sequence
<220> FEATURE:
<223> OTHER INFORMATION: probe for ARHGAP22

<400> SEQUENCE: 2
ggaactctga acgggcgcgg gaggatgcgg agaggaggaa ccagctgttg cagagggaaa    60
tggaggagtt tttttcgacc ctaggaagct tgactgttgg                          100

<210> SEQ ID NO 3
<211> LENGTH: 100
<212> TYPE: DNA
<213> ORGANISM: Artificial Sequence
<220> FEATURE:
<223> OTHER INFORMATION: probe for C19orf77

<400> SEQUENCE: 3
ggctctctgg gcaaacatgg ttttcatgca cccctcttcc tgagcttggt ccctgcctgg    60
tgattcttct tatactcgga gagcatccct ggttgaggag                          100

<210> SEQ ID NO 4
<211> LENGTH: 100
<212> TYPE: DNA
<213> ORGANISM: Artificial Sequence
<220> FEATURE:
<223> OTHER INFORMATION: probe for CD34

<400> SEQUENCE: 4
atatggtcat agcccagatc agctcctaac ccttatcacc agctgcctct tctgtgggtg    60
acccaggtcc ttgtttgctg ttgatttctt tccagagggg                          100

<210> SEQ ID NO 5
<211> LENGTH: 100
<212> TYPE: DNA
<213> ORGANISM: Artificial Sequence
<220> FEATURE:
<223> OTHER INFORMATION: probe for CDK6

<400> SEQUENCE: 5
agaagcagaa ctgtcagctt gtgccttgag gcttccagaa cgtgtcagat ggagaagtcc    60
aagtttccat gcttcaggca acttagctgt gtacagaagc                          100

<210> SEQ ID NO 6
<211> LENGTH: 100
<212> TYPE: DNA
<213> ORGANISM: Artificial Sequence
<220> FEATURE:
<223> OTHER INFORMATION: probe for CPXM1

<400> SEQUENCE: 6
agcaggtgcg catgggcatt gcaggagtgg tgagggacaa ggacacggag cttgggattg    60
ctgacgctgt cattgccgtg gatgggatta accatgacgt                          100

<210> SEQ ID NO 7
<211> LENGTH: 100
<212> TYPE: DNA
<213> ORGANISM: Artificial Sequence
<220> FEATURE:
<223> OTHER INFORMATION: probe for DNMT3B

<400> SEQUENCE: 7
ggggtgtgct gagttctata atataagctg ccatatattt tgtagacaag tatggctcct    60
ccatatctcc ctcttcccta ggagaggagt gtgaagcaag                          100

<210> SEQ ID NO 8
<211> LENGTH: 100
<212> TYPE: DNA
<213> ORGANISM: Artificial Sequence
<220> FEATURE:
<223> OTHER INFORMATION: probe for DPYSL3

<400> SEQUENCE: 8
ccctgggcag ccagcattca ttgtaagttc cctctttgaa aactggtgtg tgggtgttca    60
gttctgtgtc tggtgggtat ggacagacag taatctcctg                          100

<210> SEQ ID NO 9

```
<211> LENGTH: 100
<212> TYPE: DNA
<213> ORGANISM: Artificial Sequence
<220> FEATURE:
<223> OTHER INFORMATION: probe for EMP1

<400> SEQUENCE: 9
tctagttaag gaaatgttga gggcaagcca ccaaattacc taggctgagg ttagagagat      60
tggccagcaa aaactgtggg aagatgaact ttgtcattat                          100

<210> SEQ ID NO 10
<211> LENGTH: 100
<212> TYPE: DNA
<213> ORGANISM: Artificial Sequence
<220> FEATURE:
<223> OTHER INFORMATION: probe for GPR56

<400> SEQUENCE: 10
cgccctcggc cgcccatcat ggttaattct gtccaacaaa cacacacggg tagattgctg      60
gcctgttgta ggtggtaggg acacagatga ccgacctggt                          100

<210> SEQ ID NO 11
<211> LENGTH: 100
<212> TYPE: DNA
<213> ORGANISM: Artificial Sequence
<220> FEATURE:
<223> OTHER INFORMATION: probe for KIAA0125

<400> SEQUENCE: 11
acagttctga agtcaaaggc tgatgtcctg tttctctttc cctctgtgac cgactccctt      60
cccagtggta acaagtaccc acagcttggt ttgaatttct                          100

<210> SEQ ID NO 12
<211> LENGTH: 100
<212> TYPE: DNA
<213> ORGANISM: Artificial Sequence
<220> FEATURE:
<223> OTHER INFORMATION: probe for LAPTM4B

<400> SEQUENCE: 12
ccaactgact ttatcaagtg gaattgggat atatttgata tacttctgcc taacaacatg      60
gaaaagggtt ttcttttccc tgcaagctac atcctactgc                          100

<210> SEQ ID NO 13
<211> LENGTH: 100
<212> TYPE: DNA
<213> ORGANISM: Artificial Sequence
<220> FEATURE:
<223> OTHER INFORMATION: probe for MMRN1

<400> SEQUENCE: 13
gcagacatcc ttttactggt gacaactgca ctatcaagct tgtggaagaa aatgctttag      60
ctccagattt ttccaaagga tcttacagat atgcacccat                          100

<210> SEQ ID NO 14
<211> LENGTH: 100
<212> TYPE: DNA
<213> ORGANISM: Artificial Sequence
<220> FEATURE:
<223> OTHER INFORMATION: probe for NGFRAP1

<400> SEQUENCE: 14
accgagaaga gtgacagggc tgtgcgctct ggggcacctc atgcagacgg gagtagggag      60
```

```
gctgtttttt gcgcgtgcat atggcggtgg cgggtggggg                         100

<210> SEQ ID NO 15
<211> LENGTH: 100
<212> TYPE: DNA
<213> ORGANISM: Artificial Sequence
<220> FEATURE:
<223> OTHER INFORMATION: probe for NYNRIN

<400> SEQUENCE: 15
gattaagctt cctgactccc agttcaccat gaaaagggtt ctggcaacag gttcaagctg    60
gagaatcctt caaaatgcta cacccacatt ctctccaact                         100

<210> SEQ ID NO 16
<211> LENGTH: 100
<212> TYPE: DNA
<213> ORGANISM: Artificial Sequence
<220> FEATURE:
<223> OTHER INFORMATION: probe for SOCS2

<400> SEQUENCE: 16
gagagaaaga actcctcata ggaatactga agaagtggga aggaaccaag ctgacacagg    60
cctcactgca atttgatatg cctgctgatc agagtctctt                         100

<210> SEQ ID NO 17
<211> LENGTH: 100
<212> TYPE: DNA
<213> ORGANISM: Artificial Sequence
<220> FEATURE:
<223> OTHER INFORMATION: probe for ZBTB46

<400> SEQUENCE: 17
tgtattggag atgtgtctac tattggggga agaggttctc gtaatcgctc ggtgggaaat    60
catggctctg ccgtcctgcc tctctgtggc cgtgggttca                         100

<210> SEQ ID NO 18
<211> LENGTH: 100
<212> TYPE: DNA
<213> ORGANISM: Artificial Sequence
<220> FEATURE:
<223> OTHER INFORMATION: probe for EIF4H

<400> SEQUENCE: 18
ctacacagca tacgtaggaa atctaccttt caatacggtt cagggcgaca tagatgctat    60
ctttaaggat ctcagcataa ggagtgtacg gctagtcaga                         100

<210> SEQ ID NO 19
<211> LENGTH: 100
<212> TYPE: DNA
<213> ORGANISM: Artificial Sequence
<220> FEATURE:
<223> OTHER INFORMATION: probe for HNRNPK

<400> SEQUENCE: 19
gattggtgtg cccgtttaat aaaagaatat ggaaactgaa cagccagaag aaaccttccc    60
taacactgaa accaatggtg aatttggtaa acgccctgca                         100

<210> SEQ ID NO 20
<211> LENGTH: 100
<212> TYPE: DNA
<213> ORGANISM: Artificial Sequence
<220> FEATURE:
```

<223> OTHER INFORMATION: probe for HNRNPL

<400> SEQUENCE: 20
ctctctcaat ggggctgata tctattctgg ctgttgcact ctgaagatcg aatacgcaaa    60
gcctacacgc ttgaatgtgt tcaagaatga tcaggatact                         100

<210> SEQ ID NO 21
<211> LENGTH: 100
<212> TYPE: DNA
<213> ORGANISM: Artificial Sequence
<220> FEATURE:
<223> OTHER INFORMATION: probe for PSMA1

<400> SEQUENCE: 21
ggttgcattg aaaagggcgc aatcagagct tgcagctcat cagaaaaaaa ttctccatgt    60
tgacaaccat attggtatct caattgcggg gcttactgct                         100

<210> SEQ ID NO 22
<211> LENGTH: 100
<212> TYPE: DNA
<213> ORGANISM: Artificial Sequence
<220> FEATURE:
<223> OTHER INFORMATION: probe for PSMD6

<400> SEQUENCE: 22
ataggtcatt aaccctttggc tatatggcag aagcgtttgg tgttggtgtg gaattcattg    60
atcaggaact gtccaggttt attgctgccg ggagactaca                         100

<210> SEQ ID NO 23
<211> LENGTH: 100
<212> TYPE: DNA
<213> ORGANISM: Artificial Sequence
<220> FEATURE:
<223> OTHER INFORMATION: probe for SF3B2

<400> SEQUENCE: 23
ggacggaagt gagacacctc agctcttcac tgtgttgcca gagaagagaa cagccactgt    60
tggaggggcc atgatgggat caacccacat ttatgacatg                         100

<210> SEQ ID NO 24
<211> LENGTH: 100
<212> TYPE: DNA
<213> ORGANISM: Artificial Sequence
<220> FEATURE:
<223> OTHER INFORMATION: probe for SLC25A3

<400> SEQUENCE: 24
tggtatctgt gttgaataaa gaaaaaggta gcagtgcttc tctggtcctc aagagacttg    60
gatttaaagg tgtatggaag ggactgtttg cccgtatcat                         100

<210> SEQ ID NO 25
<211> LENGTH: 100
<212> TYPE: DNA
<213> ORGANISM: Artificial Sequence
<220> FEATURE:
<223> OTHER INFORMATION: probe for UBE2I

<400> SEQUENCE: 25
cggccgcccg agggactttg aacatgtcgg ggatcgccct cagcagactc gcccaggaga    60
ggaaagcatg gaggaaagac cacccatttg gtttcgtggc                         100

```
<210> SEQ ID NO 26
<211> LENGTH: 100
<212> TYPE: DNA
<213> ORGANISM: Artificial Sequence
<220> FEATURE:
<223> OTHER INFORMATION: probe for VPS4A

<400> SEQUENCE: 26
caagctctgc ctcaaagacc gagtgacata agccattccc accctcctag gttcacatcc      60
agggctgtgt cttccttggg ggaggagatg gtgtcgttta                           100

<210> SEQ ID NO 27
<211> LENGTH: 100
<212> TYPE: DNA
<213> ORGANISM: Artificial Sequence
<220> FEATURE:
<223> OTHER INFORMATION: probe for GAPDH

<400> SEQUENCE: 27
cactcctcca cctttgacgc tggggctggc attgccctca acgaccactt tgtcaagctc      60
atttcctggt atgacaacga atttggctac agcaacaggg                           100

<210> SEQ ID NO 28
<211> LENGTH: 100
<212> TYPE: DNA
<213> ORGANISM: Artificial Sequence
<220> FEATURE:
<223> OTHER INFORMATION: probe for TBP

<400> SEQUENCE: 28
acagtgaatc ttggttgtaa acttgaccta aagaccattg cacttcgtgc ccgaaacgcc      60
gaatataatc ccaagcggtt tgctgcggta atcatgagga                           100

<210> SEQ ID NO 29
<211> LENGTH: 100
<212> TYPE: DNA
<213> ORGANISM: Artificial Sequence
<220> FEATURE:
<223> OTHER INFORMATION: probe for ABL1

<400> SEQUENCE: 29
ctgcgtgagc tatgtggatt ccatccagca aatgaggaac aagtttgcct tccgagaggc      60
catcaacaaa ctggagaata atctccggga gcttcagatc                           100
```

METHOD FOR IDENTIFYING HIGH-RISK AML PATIENTS

CROSS-REFERENCE TO RELATED APPLICATIONS

This application is a national phase application under 35 U.S.C. § 371 of International Application No. PCT/CA2017/000025 filed 6 Feb. 2017, which claims priority to U.S. Provisional Applications No. 62/292,254 filed 6 Feb. 2016, No. 62/348,365 filed 10 Jun. 2016, No, 62/426,100 filed 24 Nov. 2016, and No. 62/429,205 filed 2 Dec. 2016. The entire contents of each of the above-referenced disclosures is specifically incorporated by reference herein without disclaimer.

FIELD OF THE INVENTION

The invention relates to gene-related methods and products for the identification of high-risk acute myeloid leukemia (AML) patients, and methods of predicting response to treatment.

BACKGROUND

Refractoriness to induction chemotherapy and relapse after achievement of remission remain the main obstacles to cure in AML[1]. Chemotherapy based on cytarabine plus an anthracycline has been the backbone of AML therapy since the 1970s, with improvements in survival attributable to risk-stratified therapy and better supportive care[2]. Most AML centers initiate standard induction chemotherapy prior to the availability of cytogenetic results; patients are later assigned to post-remission strategies based on cytogenetic abnormalities and a small set of gene mutations that broadly define favorable, intermediate, and adverse risk categories[3-5]. However, in the favorable and intermediate risk groups, a subset of patients rapidly relapse despite the lack of adverse risk factors[6]. For example, cytogenetically normal (CN) patients with NPM1 mutation and without FLT3-ITD are considered better risk, but ~35% relapse within 2 years following conventional therapy[6]. Moreover, patients with cytogenetically- or mutationally-defined adverse risk features do poorly with standard induction therapies, and although patients with non-responding disease can often achieve remission with second-line therapy, a higher number of chemotherapy cycles required to achieve morphologic remission portends a worse outcome, with or without allogeneic stem-cell transplantation (allo-SCT)[7;8]. The ability to identify these high-risk patients prior to starting induction chemotherapy would afford the opportunity to test the benefit of intensified or alternative induction strategies in clinical trials[9]. To achieve this, there is an urgent need for robust biomarkers for rapid and more accurate risk stratification, not only in the post-remission setting but also prior to treatment initiation.

The high rate of relapse in AML has been attributed to the persistence of disease-sustaining leukemia stem cells (LSC) in remission. LSCs possess stem cell properties including quiescence that are linked to therapy resistance[10-15]. In a mouse model of MLL-rearranged AML, an expression profile enriched for stem cell-related genes was associated with increased resistance to conventional chemotherapy[16]. The link between LSC properties and therapy resistance and relapse supports analysis of LSC-specific molecular programs to identify predictive and/or prognostic biomarkers.

Experimentally, LSCs are best assayed by xenotransplantation into immune-deficient mice, as cell surface phenotype alone is unreliable[17;18]. Xenotransplantation assays have been used to elucidate the biologic properties of normal hematopoietic stem cells (HSCs)[19-22], and there is a growing body of evidence that these assays also detect clinically relevant properties of LSCs[18;23;24].

SUMMARY OF THE INVENTION

In an aspect, there is provided a method of prognosing or classifying a subject with AML comprising: (a) determining the expression level of at least 3 genes in a test sample from the subject selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56; and (b) comparing expression of the at least 3 genes in the test sample with reference expression levels of the at least 3 genes from control samples from a cohort of patients; wherein a difference or similarity in the expression of the at least 3 genes in the test sample and the reference expression levels is used to prognose or classify the subject with AML into a low risk group or a high risk group for worse survival.

In preferable embodiments, the method further comprises calculating a LSC Score comprising the weighted sum of expression of each of the at least 3 genes. In some embodiments, classification of the subject into a high-risk group is based on a high LSC Score in reference to the control cohort of AML patients.

In a further aspect, there is provided a method of selecting a therapy for a subject with AML, comprising the steps: (a) classifying the subject with AML into a high risk group or a low risk group according to the methods described herein; and (b) selecting a more aggressive therapy, preferably intensified chemotherapy, for the high risk group or a less aggressive therapy, preferably standard chemotherapy, for the low risk group.

In a further aspect, there is provided a composition comprising a plurality of isolated nucleic acid sequences, wherein each isolated nucleic acid sequence hybridizes to: (a) the mRNA of at least 3 genes selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56; and/or (b) a nucleic acid complementary to a), wherein the composition is used to measure the level of expression of the at least 3 genes.

In a further aspect, there is provided an array comprising, for each of at least 3 genes selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56, one or more polynucleotide probes complementary and hybridizable thereto.

In a further aspect, there is provided a computer program product for use in conjunction with a computer having a processor and a memory connected to the processor, the computer program product comprising a computer readable storage medium having a computer mechanism encoded thereon, wherein the computer program mechanism may be loaded into the memory of the computer and cause the computer to carry out the method described herein.

In a further aspect, there is provided a computer implemented product for predicting a prognosis or classifying a subject with AML comprising: (a) a means for receiving values corresponding to a subject expression profile in a subject sample; (b) a database comprising a reference expression profile representing a control, wherein the subject expression profile and the reference profile each have at least one value representing the expression level of at least 3 genes selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56; wherein the computer implemented product compares the reference expression profile to the subject biomarker expression profile, wherein a difference in the expression profiles is used to prognose or classify the subject with AML into a low risk group or a high risk group for worse survival.

In a further aspect, there is provided the computer-implemented product described herein carrying out the method described herein.

In a further aspect, there is provided a computer implemented product for guiding therapy for a subject with AML comprising the computer implemented product described herein, wherein the computer implemented product further recommends levels of therapies based on whether the subject with AML has been classified into the low risk group or the high risk group.

In a further aspect, there is provided a computer readable medium having stored thereon a data structure for storing the computer-implemented product described herein.

In a further aspect, there is provided a computer system comprising (a) a database including records comprising a reference expression profile of at least 3 genes selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56 for a cohort of patients; (b) a user interface capable of receiving a selection of expression levels of the at least 3 genes for use in comparing to the reference expression profile in the database; (c) an output that displays a prediction of prognosis or therapy wherein a difference in the expression profiles is used to prognose or classify the subject with AML into a low risk group or a high risk group of worse survival.

In a further aspect, there is provided a kit comprising reagents for detecting the expression of at least 3 genes selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56 in a sample.

In a further aspect, there is provided, a method of predicting therapy resistance in a subject with AML comprising: (a) determining the expression level of at least 3 genes in a test sample from the subject selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56; and (b) comparing expression of at least 3 genes in the test sample with reference expression levels of at least 3 genes from control samples from a cohort of patients; wherein a difference or similarity in the expression of at least 3 genes in the test sample and the reference expression levels is used to predict therapy resistance.

Figure 1A:
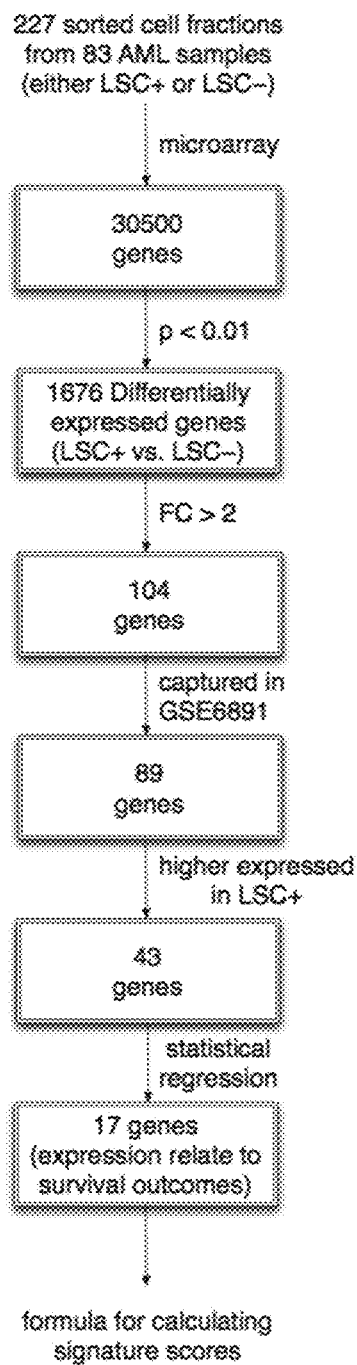
FIG. 1 shows analysis of LSC-Specific Gene Expression Identifies an Optimal 17-Gene Prognostic Signature. Panel A shows the strategy used to identify the 17 LSC signature genes. Panel B shows the gene expression (GE) patterns of the top 104 DE genes between 138 LSC+ and 89 LSC− cell populations. Each column represents one gene and each row represents one cell fraction, arranged from top to bottom in ascending correlation to the LSC+ reference profile. The horizontal black and white bars denote LSC+ and LSC− cell fractions, respectively. r is the coefficient of correlation between engraftment status (LSC+ vs. LSC−) of each cell fraction and its GE similarity to the LSC+ reference profile. In Panel C, the gray scale indicates the similarity of global GE of each cell fraction (shown in the same order as in Panel B) to that of stem cell enriched cell populations (HSC plus multipotent progenitors, MPP) and mature myeloid cell populations (granulocytes, GRAN; monocytes, MONO) from hUBC. r is the coefficient of correlation between similarity to the LSC+ reference profile and similarity to the hUBC cell types for each cell fraction as indicated. Panel D shows the GE patterns of the 89 DE genes that were captured in the GSE6891 microarray training dataset. The relative ordering of the 89 genes (in rows from bottom to top) is the same as in Panel B (in columns from left to right). GE profiles (in columns) are arranged by correlation to the LSC+ reference profile. The vertical black and white bars denote samples with LSC17 scores above and below the median, respectively. The 17 signature genes are depicted in the magnified view at right. Regression coefficients are provided in parentheses. In Panels B and D, white and black denote high and low microarray fluorescence intensity, respectively.

Panels A and B show KM estimates of OS with censoring at the time of allo-SCT, according to the LSC17 score, in the full PM AML cohort and CN-AML subset, respectively. Panels C and D show Simon and Makuch estimates of OS, according to LSC17 scores and whether or not patients received allo-SCT, in the full PM AML cohort and CN-AML subset, respectively. Panels E and F show a similar analysis applied to the TCGA AML dataset using KM estimates. Panels G and H show time from first complete remission (CR) to first relapse or death as competing risks, respectively, in the PM AML cohort as estimated by cumulative incidence analysis, with patient subsets defined based on LSC17 score and whether or not patients received allo-SCT. For all panels, high and low score curves show time-to-event of patients with scores above and below the median in each set, respectively. In Panels C-H, solid and dotted lines denote patients that did and did not receive allo-SCT, respectively.

FIG. 12 shows that LSC scores improve prediction of initial therapy response. Panels A and E show step-wise improvements in prediction of response to initial induction in the entire PM AML cohort and CN-AML subset, respectively, according to increases in AUROC, using multivariate logistic regression while accounting for age, WBC count, and de novo vs. secondary AML in a base model (lowest curve), then adding NPM1 and FLT3-ITD mutations (middle curve), and LSC17 score (top curve). Panel C is the same as Panel A but analysis was done using cytogenetic risk in place of molecular data. Panel G shows the same analysis as presented in panel C, but using the response sub-signature refined from the LSC17 score instead of the LSC17 score. Panels B, D, F, and H show covariate significance plots corresponding to the models used in Panels A, C, E, and G, respectively, according to the Wald Chi-squared statistic.

FIG. 13 shows KM estimates of OS in the subset of patients designated with "driver mutations but no detected class-defining lesions", "no detected driver mutations", and "meeting criteria for 2 or more subgroups" according to the LSC17 score as computed using microarray data. OS of patients with scores above and below the median in the patient group are shown by dotted and solid lines, respectively.

FIG. 14 a-c, KM estimates of OS, EFS, and RFS, respectively, for patients with high LSC17 scores treated with the addition of gemtuzumab ozogamicin (GO) (dotted curve) compared to no-GO (control, solid curve). d-f, same as a-c but for patients with low LSC17 scores.

FIG. 15, LSC13 sub-score prediction of CN-LMR patients across several microarray (Panels A-C), RNA-Seq (Panel D), and NanoString (Panels E and F) cohorts.

DESCRIPTION

In the following description, numerous specific details are set forth to provide a thorough understanding of the invention. However, it is understood that the invention may be practiced without these specific details.

In AML, most patients are initiated on standard chemotherapy and afterwards assigned to a post-remission strategy based on genetically-defined risk categories. However, outcomes remain heterogeneous, indicating the need for novel biomarker tests that can rapidly and accurately identify high-risk patients, allowing better stratification of both induction and post-remission therapy. As patient outcomes are linked to LSC properties that confer therapy resistance and drive relapse, LSC-based biomarkers may be highly informative.

We tested 227 CD34/CD38 cell fractions from 78 AML patients for LSC activity in xenotransplantation assays. Comparison of microarray-based GE profiles between 138 LSC+ and 89 LSC− fractions identified 104 differentially expressed (DE) LSC− specific genes. To obtain prognostic signatures, we performed statistical regression analysis of LSC GE against patient outcome using a training cohort of 495 AML patients treated with curative intent.

A score calculated as the weighted sum of expression of 17 LSC signature genes (LSC17) was strongly associated with survival in 4 independent datasets (716 AML cases) spanning all risk categories in multi-variate analysis; an optimized 3-gene sub-score (LSC3) was prognostic in favorable risk subsets. These scores were robust across GE technology platforms, including the clinically serviceable NanoString system (LSC17: HR=2.73, P<0.0001; LSC3: HR=6.3, P<0.02).

The LSC17 and LSC3 scores provide rapid and accurate identification of high-risk patients for whom conventional chemotherapy is non-curative. These scores will enable evaluation in clinical trials of whether such patients may benefit from novel and/or more intensified therapies during induction or in the post-remission setting.

In an aspect, there is provided a method of prognosing or classifying a subject with AML comprising: (a) determining the expression level of at least 3 genes in a test sample from the subject selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56; and (b) comparing expression of the at least 3 genes in the test sample with reference expression levels of the at least 3 genes from control samples from a cohort of patients; wherein a difference or similarity in the expression of the at least 3 genes in the test sample and the reference expression levels is used to prognose or classify the subject with AML into a low risk group or a high risk group for worse survival.

In various embodiments, the at least 3 genes is at least 4, 5, 6, 7, 8, 9, 10, 11, 12, 13, 14, 15, 16 or 17 genes.

The term "prognosis" as used herein refers to a clinical outcome group such as a worse survival group or a better survival group associated with a disease subtype which is reflected by a reference profile such as a biomarker reference expression profile or reflected by an expression level of the fifteen biomarkers disclosed herein. The prognosis provides an indication of disease progression and includes an indication of likelihood of death due to leukemia. In one embodiment the clinical outcome class includes a better survival group and a worse survival group.

The term "prognosing or classifying" as used herein means predicting or identifying the clinical outcome group that a subject belongs to according to the subject's similarity to a reference profile or biomarker expression level associated with the prognosis. For example, prognosing or classifying comprises a method or process of determining whether an individual with AML has a better or worse survival outcome, or grouping an individual with AML into a better survival group or a worse survival group, or predicting whether or not an individual with AML will respond to therapy.

The term "subject" as used herein refers to any member of the animal kingdom, preferably a human being and most preferably a human being that has AML or that is suspected of having AML.

The term "test sample" as used herein refers to any fluid, cell or tissue sample from a subject which can be assayed for biomarker expression products and/or a reference expression profile, e.g. genes differentially expressed in subjects with AML according to survival outcome. In an embodiment, the sample comprises WBCs obtained from peripheral blood (PB) or bone marrow (BM).

The phrase "determining the expression of biomarkers" as used herein refers to determining or quantifying RNA or proteins or protein activities or protein-related metabolites expressed by the biomarkers. The term "RNA" includes mRNA transcripts, and/or specific spliced or other alternative variants of mRNA, including anti-sense products. The term "RNA product of the biomarker" as used herein refers to RNA transcripts transcribed from the biomarkers and/or specific spliced or alternative variants. In the case of "protein", it refers to proteins translated from the RNA transcripts transcribed from the biomarkers. The term "protein product of the biomarker" refers to proteins translated from RNA products of the biomarkers.

The term "level of expression" or "expression level" as used herein refers to a measurable level of expression of the products of biomarkers, such as, without limitation, the level of micro-RNA, messenger RNA transcript expressed or of a specific exon or other portion of a transcript, the level of proteins or portions thereof expressed of the biomarkers, the number or presence of DNA polymorphisms of the biomarkers, the enzymatic or other activities of the biomarkers, and the level of specific metabolites.

As used herein, the term "control" refers to a specific value or dataset that can be used to prognose or classify the value e.g expression level or reference expression profile obtained from the test sample associated with an outcome class. In one embodiment, a dataset may be obtained from samples from a group of subjects known to have AML and better survival outcome or known to have AML and have worse survival outcome or known to have AML and have benefited from chemotherapy (or intensified chemotherapy) or known to have AML and not have benefited from chemotherapy (or intensified chemotherapy). The expression data of the biomarkers in the dataset can be used to create a control value that is used in testing samples from new patients. In such an embodiment, the "control" is a predetermined value for the set of at least 3 of the 17 biomarkers obtained from AML patients whose biomarker expression values and survival times are known. Alternatively, the "control" is a predetermined reference profile for the set of at least three of the seventeen biomarkers described herein obtained from patients whose survival times are known.

The term "differentially expressed" or "differential expression" as used herein refers to a difference in the level of expression of the biomarkers that can be assayed by measuring the level of expression of the products of the biomarkers, such as the difference in level of mRNA or a portion thereof expressed. In a preferred embodiment, the difference is statistically significant. The term "difference in the level of expression" refers to an increase or decrease in the measurable expression level of a given biomarker, for example as measured by the amount of mRNA as compared with the measurable expression level of a given biomarker in a control.

The term "better survival" as used herein refers to an increased chance of survival as compared to patients in the "worse survival" group. For example, the biomarkers of the application can prognose or classify patients into a "better survival group". These patients are at a lower risk of death from the disease.

The term "worse survival" as used herein refers to an increased risk of death as compared to patients in the "better survival" group. For example, biomarkers or genes of the application can prognose or classify patients into a "worse survival group". These patients are at greater risk of death or adverse reaction from disease, treatment for the disease or other causes.

Accordingly, in one embodiment, the biomarker reference expression profile comprises a worse survival group. In another embodiment, the biomarker reference expression profile comprises a better survival group.

In some embodiments, the method further comprises building a subject GE profile from the determined expression of the at least 3 genes. The method may optionally further comprise obtaining a reference GE profile associated with a prognosis, wherein the subject GE profile and the gene reference expression profile each have values representing the expression level of the at least 3 genes.

The term "reference expression profile" as used herein refers to the expression level of at least 3 of the 17 biomarkers selected from DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, and GPR56 associated with a clinical outcome in a AML patient. The reference expression profile comprises 17 values, each value representing the level of a biomarker, wherein each biomarker corresponds to one gene selected from DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, and GPR56. The reference expression profile is identified using one or more samples comprising tumor or adjacent or other-wise tumour-related stromal/blood based tissue or cells, wherein the expression is similar between related samples defining an outcome class or group such as worse survival or better survival and is different to unrelated samples defining a different outcome class such that the reference expression profile is associated with a particular clinical outcome. The reference expression profile is accordingly a reference profile or reference signature of the expression of at least 3 of the 17 biomarkers selected from DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, and GPR56, to which the subject expression levels of the corresponding genes in a patient sample are compared in methods for determining or predicting clinical outcome.

In preferable embodiments, the method further comprises calculating a LSC Score comprising the weighted sum expression of each of the at least 3 genes. In some embodiments, classification of the subject into a high-risk group is based on a high LSC Score in reference to the control cohort of AML patients. Therefore, in this embodiment the reference expression profile is the expression profile of a reference cohort of AML patients.

In an exemplary embodiment, determination of the LSC17 score is as follows. In a reference cohort of AML patients (e.g., n=300 from the signature validation cohort described in our paper), PB or BM samples are assessed for expression of the 17 signature genes on custom designed NanoString cartridges. As described herein, each cartridge can hold up to 12 samples to be analyzed. Briefly, we run 11 patient RNA samples+1 control sample comprising a pre-defined amount of 26 synthetically created oligonucleotides mixed in equal proportions. This includes 17 distinct synthetic oligonucleotides, one created for each of the 17 signature probes+9 others corresponding to specially selected reference genes that cover a large range of expression of the 17 signature genes. This control is used for reducing non-biological (technical) sources of GE variation that maybe introduced during different cartridge runs. The transcript counts of each control lane on each cartridge are normalized such that they and the RNA counts from the other 11 RNA lanes are comparable across all cartridges. In this way, additional cartridges containing new AML samples that are run at a later time point can be normalized in this way such that new transcript counts are comparable to that of the reference cohort. Ensuring that the expression of the 17 signature genes is comparable across cartridges (new and old) also ensures that LSC17 scores computed from the transcript count data are comparable as well. Establishing a threshold value in the reference cohort scores (e.g., median LSC17 score) below which, new scores are considered low and above which are considered high is one possible way to classify patients into low or high-risk categories respectively. The reference dataset and scores do not require much storage and can be distributed with ease in the case of multi-centre studies. Notably, the threshold between high and low score would be set based on the distribution of scores in this reference dataset, but future samples need only be run with the reference oligonucleotides in order to be "normalized" to the reference set, and the score calculated. As such, in preferred embodiments, the reference set does not need to be run again.

In an embodiment, the 9 reference genes are EIF4H, HNRNPK, HNRNPL, PSMA1, PSMD6, SF3B2, SLC25A3, UBE2I, and VPS4A. In another embodiment, there are an additional 3 reference genes (e.g. ABL1, TBP, and GAPDH).

In some embodiments, determining the GE level comprises use of quantitative PCR or an array.

In some embodiments, determining the GE level comprises use of nanostring.

A person skilled in the art will appreciate that a number of methods can be used to detect or quantify the level of RNA products of the biomarkers within a sample, including arrays, such as microarrays, RT-PCR (including quantitative RT-PCR), nuclease protection assays and Northern blot analyses. For example, biomarkers may be measured using one or more methods and/or tools, including for example, but not limited to, Taqman (Life Technologies, Carlsbad, Calif.), Light-Cycler (Roche Applied Science, Penzberg, Germany), ABI fluidic card (Life Technologies), NanoString® (NanoString Technologies, Seattle, Wash. and as described in U.S. Pat. No. 7,473,767), NANODROP® technology (Thermo Fisher Scientific (Wilmington, Del.), fluidic card, and the like. The person of skill in the art will recognize such other formats and tools, which can be commercially available or which can be developed specifically for such analysis. Regarding nanostring specifically, it is also known to use synthetic oligonucleotides as a control in each nanostring cartridge to minimize inter-cartridge batch effects between runs.

In some embodiments, the AML is CN-LMR and the at least 3 genes are DPYSL3, AKR1C3, and NYNRIN.

In a further aspect, there is provided a method of selecting a therapy for a subject with AML, comprising the steps: (a) classifying the subject with AML into a high risk group or a low risk group according to the methods described herein; and (b) selecting a more aggressive therapy, preferably intensified chemotherapy, for the high risk group or a less aggressive therapy, preferably standard chemotherapy, for the low risk group.

Regimens for standard vs. intensified chemotherapy are known in the art. Intensified chemotherapy may comprise any chemotherapy that is increased along at least one axis (e.g. dose, duration, frequency, . . . etc.) as compared to standard chemotherapy treatment for a particular cancer type and stage.

In a further aspect, there is provided a composition comprising a plurality of isolated nucleic acid sequences, wherein each isolated nucleic acid sequence hybridizes to: (a) the mRNA of at least 3 genes selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56; and/or (b) a nucleic acid complementary to a), wherein the composition is used to measure the level of expression of the at least 3 genes.

The term "nucleic acid" includes DNA and RNA and can be either double stranded or single stranded.

The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. For example, 6.0× sodium chloride/sodium citrate (SSC) at about 45° C., followed by a wash of 2.0×SSC at 50° C. may be employed.

The term "probe" as used herein refers to a nucleic acid sequence that will hybridize to a nucleic acid target sequence. In one example, the probe hybridizes to the RNA biomarker or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

In a further aspect, there is provided an array comprising, for each of at least 3 genes selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56, one or more polynucleotide probes complementary and hybridizable thereto.

In a further aspect, there is provided a computer program product for use in conjunction with a computer having a processor and a memory connected to the processor, the computer program product comprising a computer readable storage medium having a computer mechanism encoded thereon, wherein the computer program mechanism may be loaded into the memory of the computer and cause the computer to carry out the method described herein.

In a further aspect, there is provided a computer implemented product for predicting a prognosis or classifying a subject with AML comprising: (a) a means for receiving values corresponding to a subject expression profile in a subject sample; (b) a database comprising a reference expression profile representing a control, wherein the subject expression profile and the reference profile each have at least one value representing the expression level of at least 3 genes selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56; wherein the computer implemented product compares the reference expression profile to the subject biomarker expression profile, wherein a difference in the expression profiles is used to prognose or classify the subject with AML into a low risk group or a high risk group for poor survival.

In preferable embodiments, the computer implemented product calculates a LSC Score comprising the weighted sum expression of each of the at least 3 genes.

Optionally, classification of the subject into a low or high-risk group is based on a high LSC Score in reference to a control cohort of AML patients.

In a further aspect, there is provided the computer-implemented product described herein carrying out the method described herein.

In a further aspect, there is provided a computer implemented product for guiding therapy for a subject with AML comprising the computer implemented product described herein, wherein the computer implemented product further recommends differential levels of therapies based on whether the subject with AML has been classified into the low risk group or the high risk group.

In a further aspect, there is provided a computer readable medium having stored thereon a data structure for storing the computer-implemented product described herein.

In some embodiments, the data structure is capable of configuring a computer to respond to queries based on records belonging to the data structure, each of the records comprising: (a) a value that identifies a reference expression profile of at least 3 genes selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56 for a control cohort of patients; (b) a value that identifies the probability of a prognosis associated with the reference expression profile. Preferably, the value is a LSC Score comprising the weighted sum expression of each of the at least 3 genes.

In a further aspect, there is provided a computer system comprising (a) a database including records comprising a reference expression profile of at least 3 genes selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56 for a cohort of patients; (b) a user interface capable of receiving a selection of expression levels of the at least 3 genes for use in comparing to the reference expression profile in the database; (c) an output that displays a prediction of prognosis or therapy wherein a difference in the expression profiles is used to prognose or classify the subject with AML into a low risk group or a high risk group of poor survival.

In a further aspect, there is provided a kit comprising reagents for detecting the expression of at least 3 genes selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56 in a sample.

In a further aspect, there is provided, a method of predicting therapy resistance in a subject with AML comprising: (a) determining the expression level of at least 3 genes in a test sample from the subject selected from the group consisting of DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56; and (b) comparing expression of the at least 3 genes in the test sample with reference expression levels of the at least 3 genes from control samples from a cohort of patients; wherein a difference or similarity in the expression of the at least 3 genes in the test sample and the reference expression levels is used to predict therapy resistance. In a preferred embodiment, the at least 3 genes comprise at least 6 genes selected from the group consisting of MMRN1, KIAA0125, CD34, GPR56, LAPTM4B, and NYNRIN.

As used herein, "therapy resistance" may mean any instance where cancer cells are resisting the effects of the chemotherapy. For example, chemotherapy resistance may occur when cancers that have been responding to a therapy suddenly begin to grow. In other examples specifically described below, therapy resistance may be a failure to achieve CR after initial induction.

The advantages of the present invention are further illustrated by the following examples. The examples and their particular details set forth herein are presented for illustration only and should not be construed as a limitation on the claims of the present invention.

EXAMPLES

Methods and Materials

Functional Assessment of LSCs in Immunodeficient Mice 83 samples obtained from 78 AML patients were sorted into fractions based on CD34/CD38 expression prior to transplantation into sublethally irradiated (225 cGy) NSG mice (227 fractions tested). Mice were sacrificed 12 weeks post-transplant and human cell engraftment in the injected right femur (RF) was assessed by flow cytometry using human-specific antibodies: anti-CD3-FITC, anti-CD19-PE, anti-CD33-PE-Cy5, anti-CD45-APC, anti-CD38-PE-Cy7 (all BD Biosciences), and anti-CD34-APC-Cy7 (Beckman Coulter). AML grafts were defined as ≥0.1% human CD45+ CD3− cells, with ≥90% CD33 expression. Sorted fractions were defined as LSC+ if transplanted cells generated an AML graft in 1 or more mice; the remaining fractions were defined as LSC−.

Gene Expression Profiling

RNA extracted from 138 LSC+ and 89 LSC− fractions was subjected to GE analysis using Illumina human HT-12 v4 microarrays. RNA from bulk mononuclear cells from an independent cohort of 307 AML patients treated at the PM Cancer Centre was analyzed using a custom NanoString codeset. Details of GE profiling, data processing, and analysis are provided herein. All raw and normalized GE data have been deposited at the gene expression omnibus (GEO, accession code GSE76009, ncbi.nlm.nih.gov/geo/query/acc.cgi?token=kfqjyaeszjcdzgh&acc=GSE76009).

Patient Samples

All biological samples were collected after obtaining informed consent according to procedures approved by the Research Ethics Board of the University Health Network (REB#01-0573-C). Mononuclear cells were isolated and stored as previously described[S1]. For all clinical samples obtained at Princess Margaret Cancer Centre, cytogenetic data were analyzed using the revised MRC prognostic classification system[S2]. NPM1, FLT3-ITD and FLT3-TKD mutational status were assessed as previously described[S3]. For functional LSC assessment, 83 clinical samples (81 PB, 1 BM, 1 peritoneal fluid) obtained from 78 patients were sorted into subfractions based on CD34 and CD38 expression. The clinical characteristics of these patients are provided in Table S1. 62 samples were diagnostic (obtained at first presentation, prior to any chemotherapy other than hydroxyurea), 16 were obtained following relapse and 5 after unsuccessful induction treatment.

Microarray Data Processing and Analysis for the Identification of LSC Associated Genes RNA extraction was carried out using Qiagen RNeasy mini kits (cat. #74106). Illumina human HT-12 v4 microarrays investigate ~47,000 targets corresponding to ~30,000 genes. To reduce technical variation within Illumina generated data, the resultant fluorescence intensity profiles were subjected to variance stabilization and robust spline normalization using the lumi 2.16.0 R package[S4]. All data was put into the log base-2 scale. Differential GE analysis was performed using the limma 3.20.9 package[S5] in R. Specifically, Smyth's moderated t-test was used with Benjamini-Hochberg multiple testing correction to compare GE profiles of LSC+ versus LSC−-fractions.

Signature Training

We used published GE profiles derived from 537 diagnostic AML samples (accession code GSE6891) for signature training purposes. Clinical annotations for 521 cases were provided by the authors[S6]. Of these 521, we removed 23 cases of myelodysplastic syndrome refractory anemia with excess blasts (MDS-RAEB), 2 cases due to missing WBC count data, and 1 because there was no raw GE data available for download, leaving 495 cases for analysis (Table S2). The GE data from this study was generated using Affymetrix Human Genome (HG) U133 Plus 2.0 GeneChips. The probes available on this array capture 89 of the 104 LSC associated genes (43 of the 48 enriched in LSC+ cell fractions) (Table S8). Raw Affymetrix CEL files were imported using the affy 1.42.3 R package[S7] and processed with the gcrma 2.36.0 package[S8] in R, which implements the Robust Multiarray Average algorithm that converts background-adjusted probe fluorescence intensities to normalized values in the $\log_2$ scale. To ensure that the Affymetrix probe annotations are in agreement with the most up-to-date human genome and transcriptome at the time of analysis, version 17 (Released on Apr. 25, 2013) of the custom chip definition files (CDF)[S9] for the HGU133 Plus2 platform from the University of Michigan was used.

Figure 5:
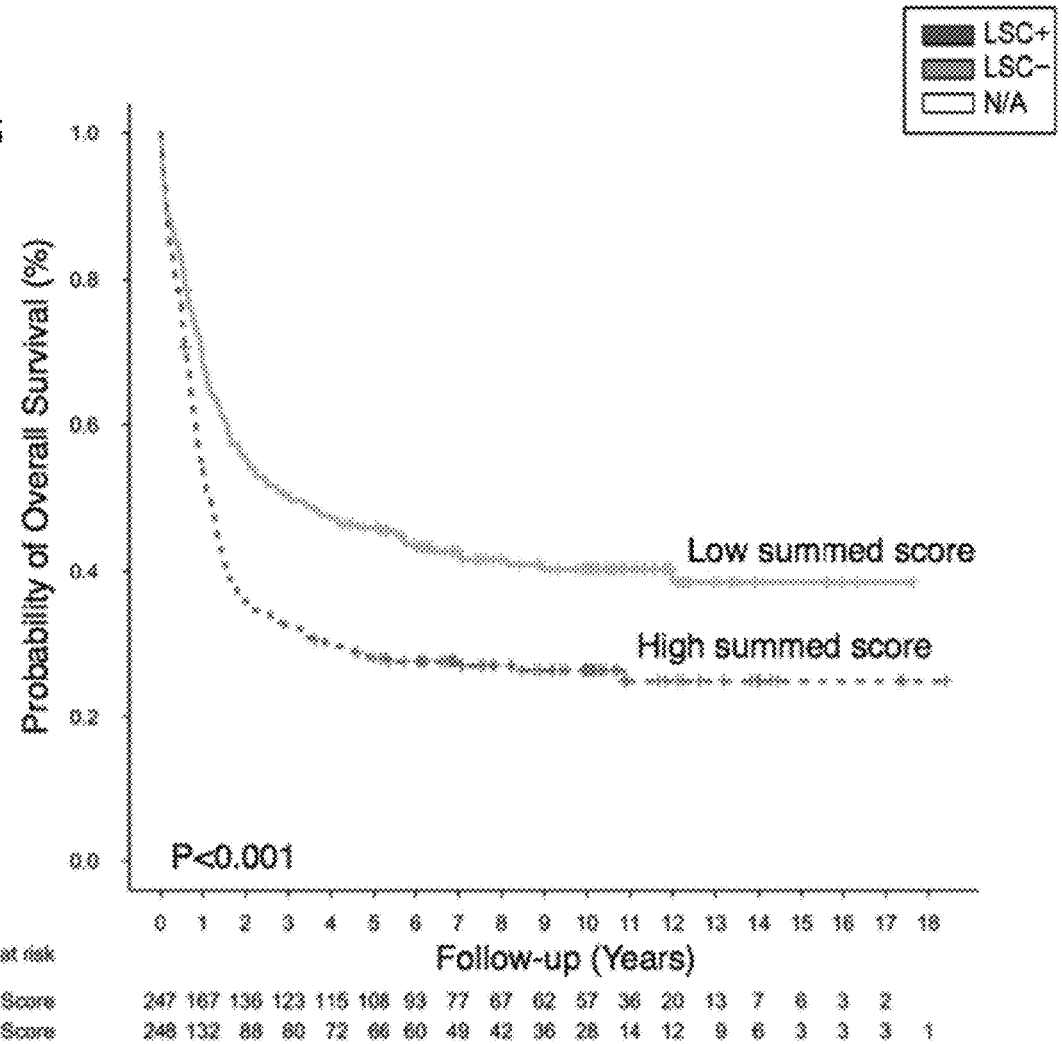
FIG. 5 shows Prognostic Value of an Un-Optimized Summed LSC Gene Expression Score. KM estimates of OS in the training cohort, according to scores calculated using microarray GE data as the sum of GE values of 43 LSC genes without regression-based optimization. OS of patients with scores above and below the median are shown by the dotted dotted and solid solid lines, respectively.

The association between LSC+ GE and survival was explored by computing per-patient risk scores based on the sum of $\log_2$ GE values of 43 probes corresponding to the genes that were higher expressed in LSC+ cell fractions for the signature training dataset (GSE6891). As several probesets existed for most genes on the array, the probeset with the highest average GE in the training data was selected to represent each gene. Although we found the summed scores to possess prognostic value (FIG. 5, median OS 13.5 months vs. 37 months for above- and below-median scores, respectively; HR=1.54; 95% CI=1.24-1.92; P<0.001), we hypothesized that not all 43 genes were required for explaining clinical outcomes in the training set and that they contributed differently to the overall scores. We suspected that removing less informative genes would de-noise the overall score and allow for a better fit to the survival data. To test this, we used a linear regression technique based on the least absolute shrinkage and selection operator (LASSO) algorithm as implemented in the glmnet 1.9-8 R package[S10;S11], while enabling leave one out cross validation to fit a Cox regression model and extract a minimal subset of genes (17 were chosen in our case) whose weighted combined GE would be highly correlated to the survival outcomes in the training cohort.

Figure 6A:
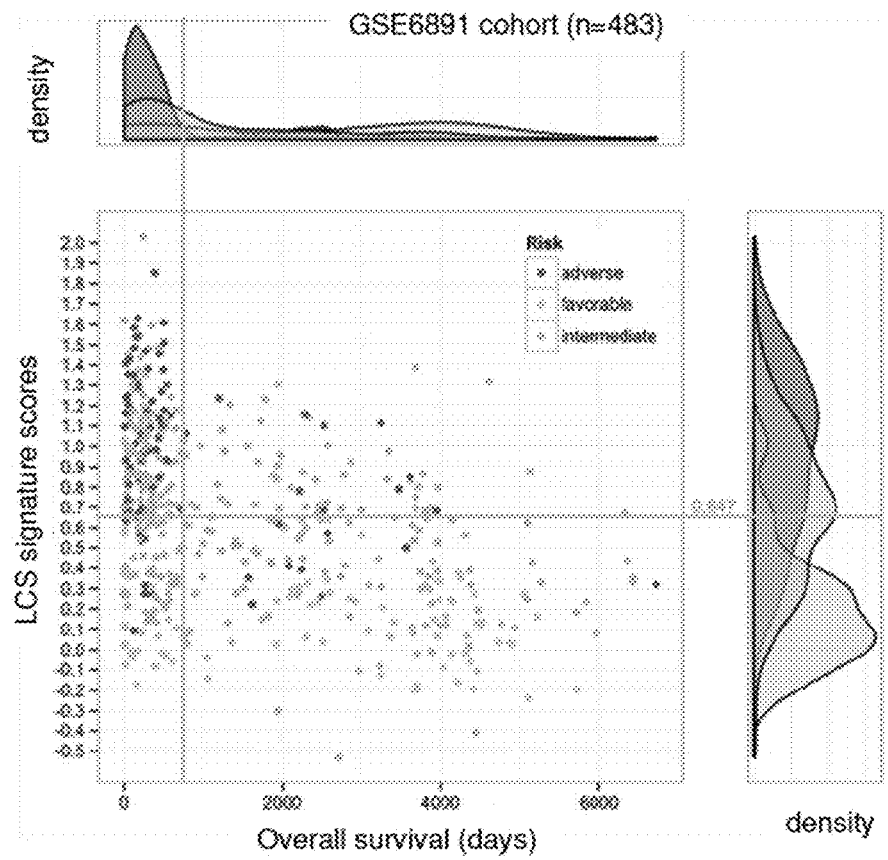
FIG. 6 shows the Median LSC17 Score Associates the Intermediate Risk Group With Either Favorable or Adverse Risk. Panel A shows all patients in the GSE6891 cohort organized into cytogenetic risk groups. Panel B shows CN-AML patients organized by molecular risk groups. In both cases, the median LSC17 score divided intermediate risk patients into subgroups with scores similar to those of the adverse and favorable risk groups. Risk categories were defined by GSE6891 investigators[S6;S27]
Figure 6B:
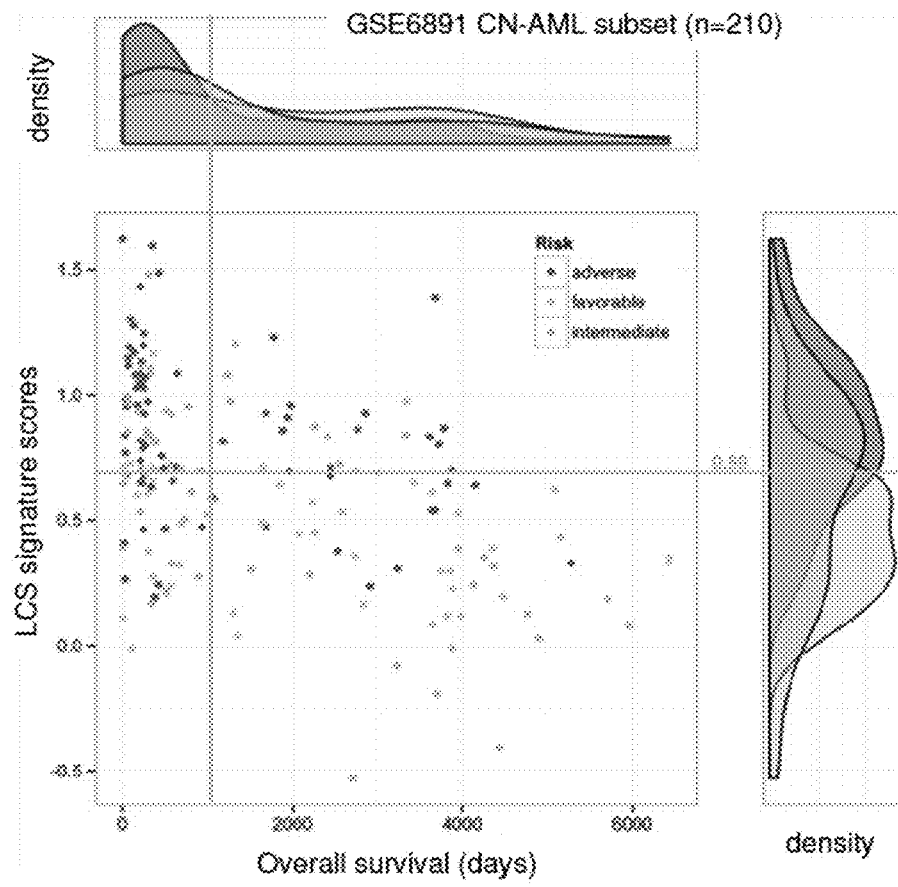
Figure 7A:
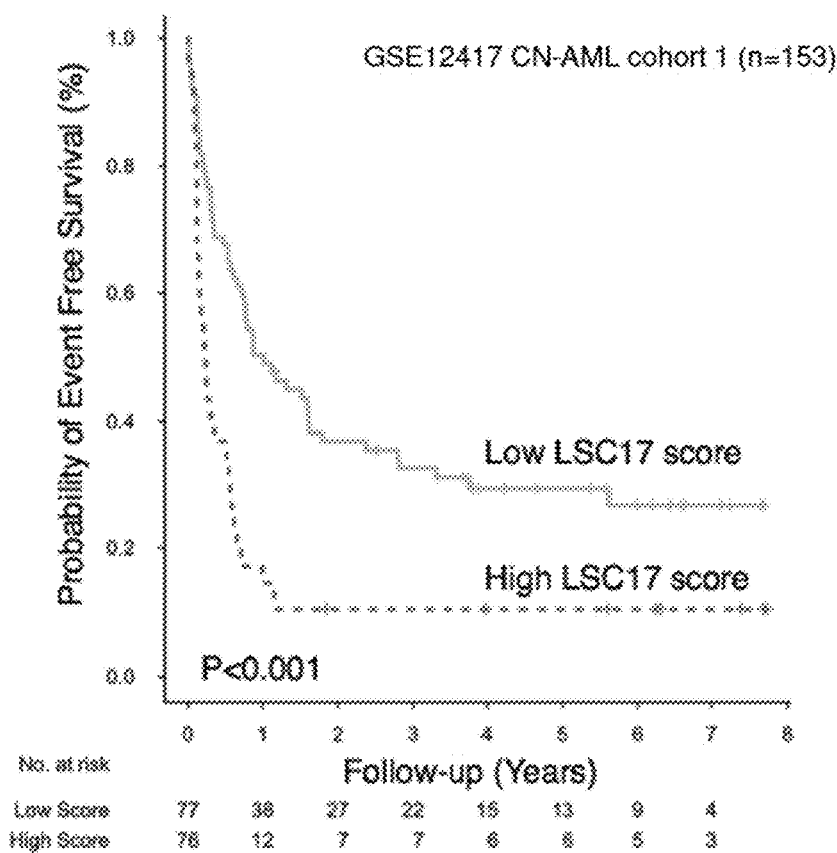
FIG. 7 shows High LSC17 Scores Are Associated With Shorter Event-Free Survival. Panels show KM estimates of event-free survival (EFS) in several independent AML cohorts, according to LSC17 scores calculated using microarray (Panels A and B) and NanoString (Panels C and D) GE datasets. For all panels, EFS of patients with scores above and below the median in each cohort are shown by the dotted and solid lines, respectively.
Figure 7B:
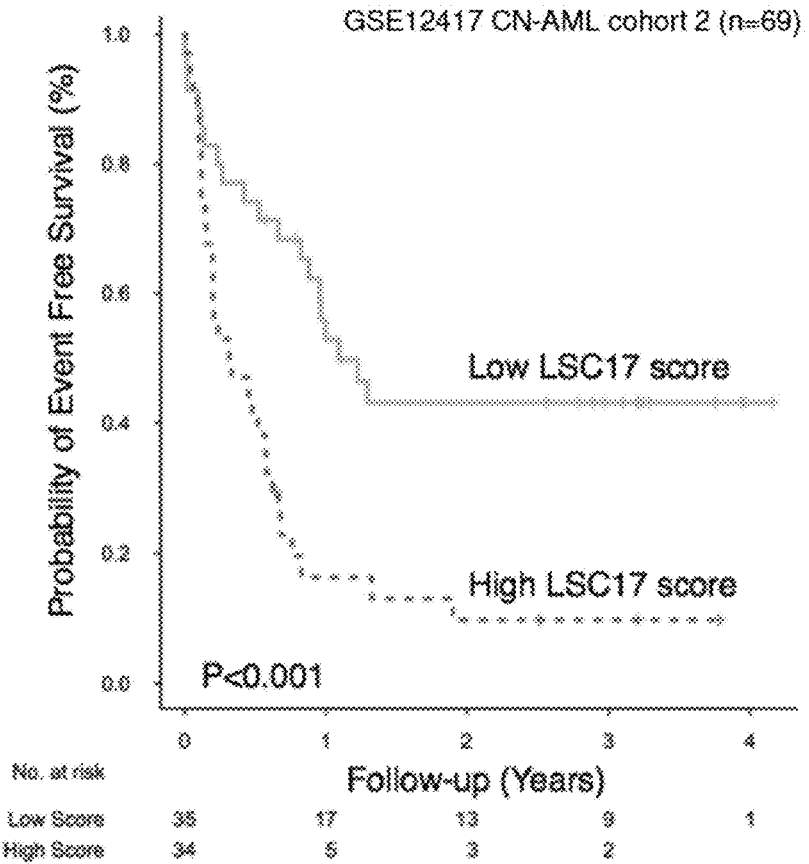
Figure 7C:
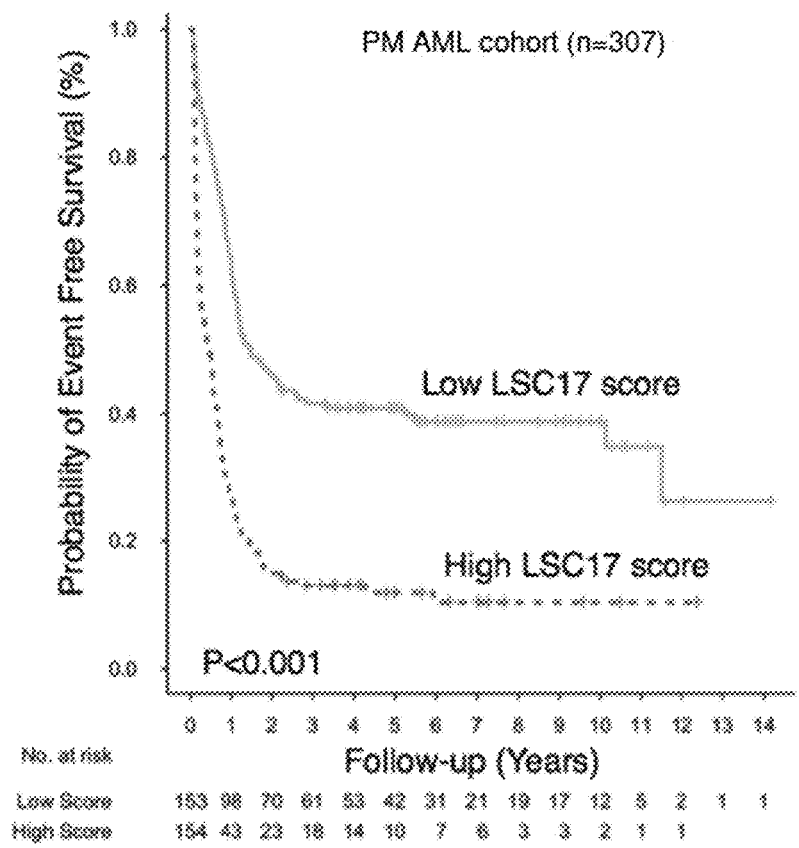
Figure 7D:
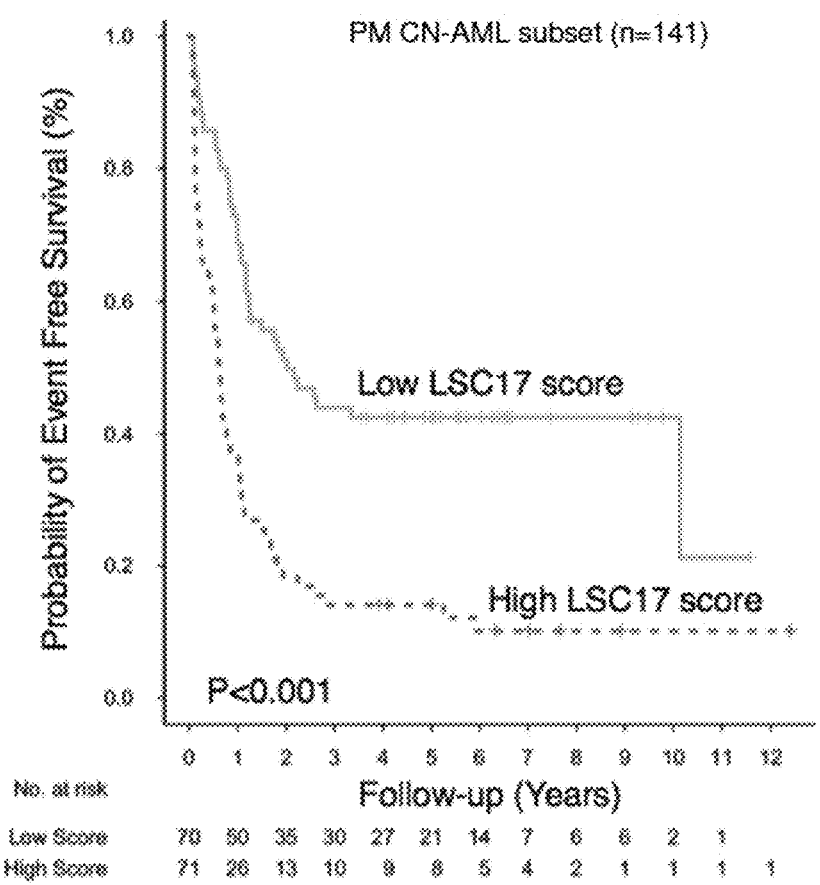
Figure 8A:
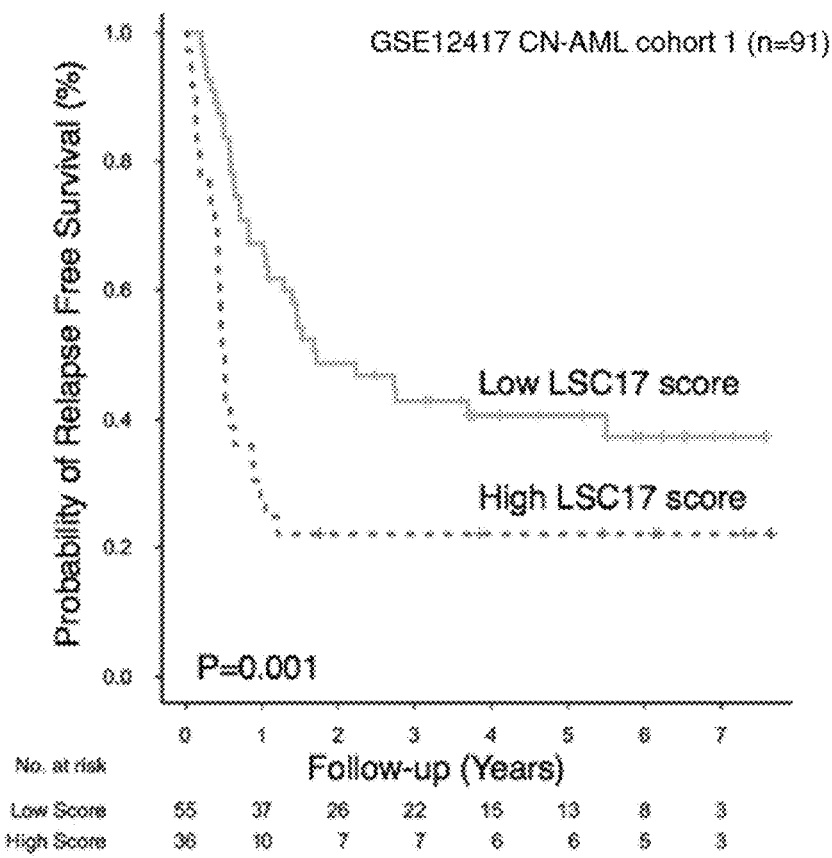
FIG. 8 shows High LSC17 Scores Are Associated With Shorter Relapse-Free Survival. Panels show KM estimates of relapse-free survival (RFS) in several independent AML cohorts, according to LSC17 scores calculated using microarray (Panels A and B) and NanoString (Panels C and D) GE datasets. For all panels, RFS of patients with scores above and below the median in each cohort are shown by the dotted and solid lines, respectively.
Figure 8B:
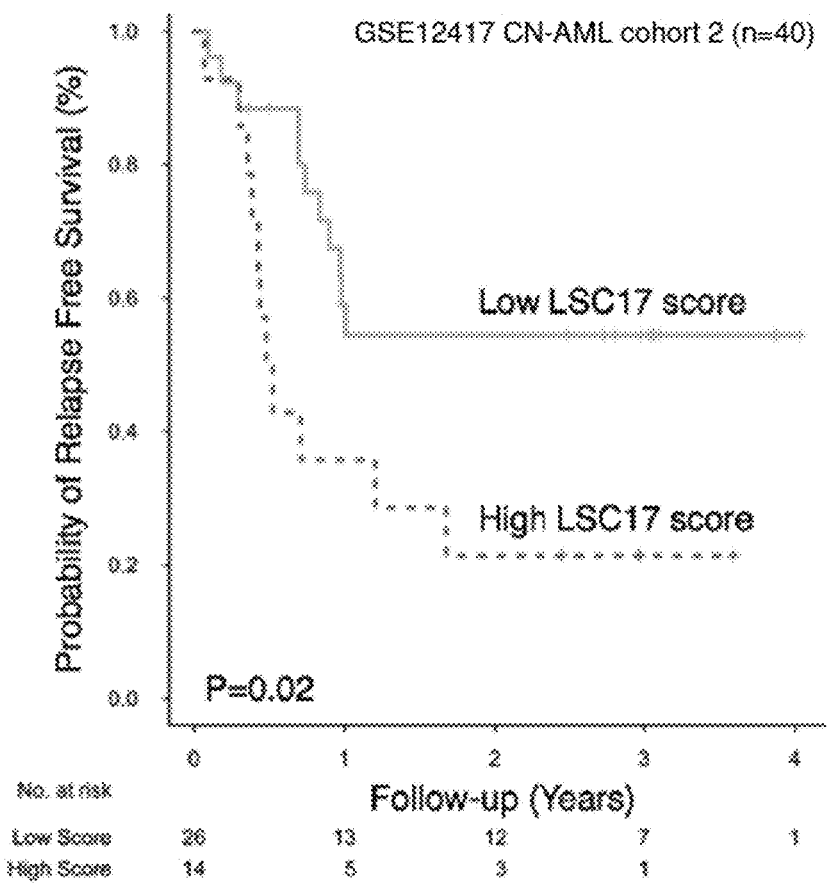
Figure 8C:
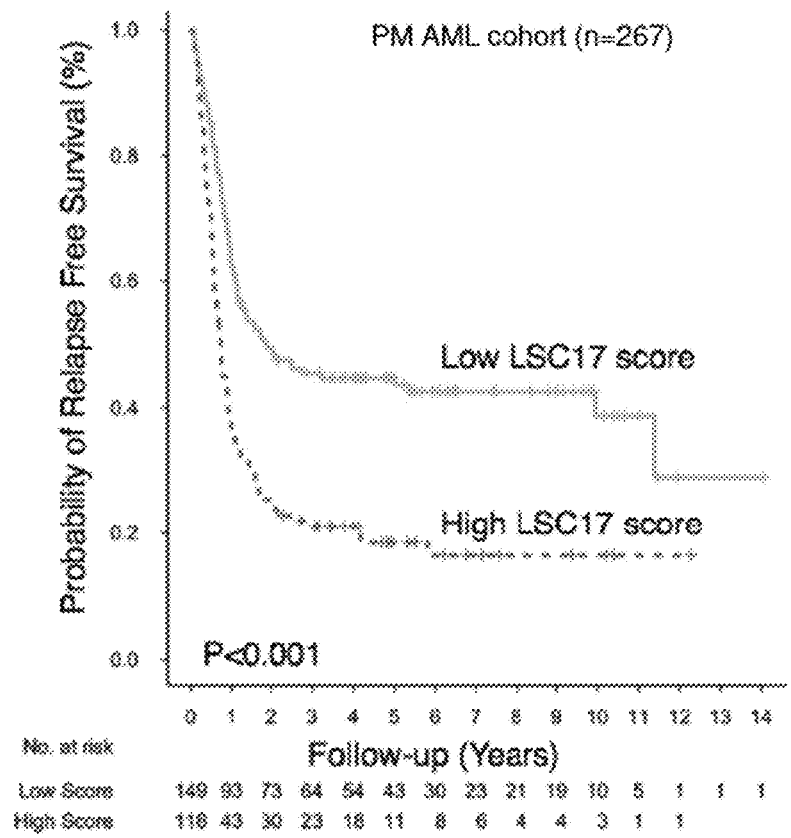
Figure 8D:
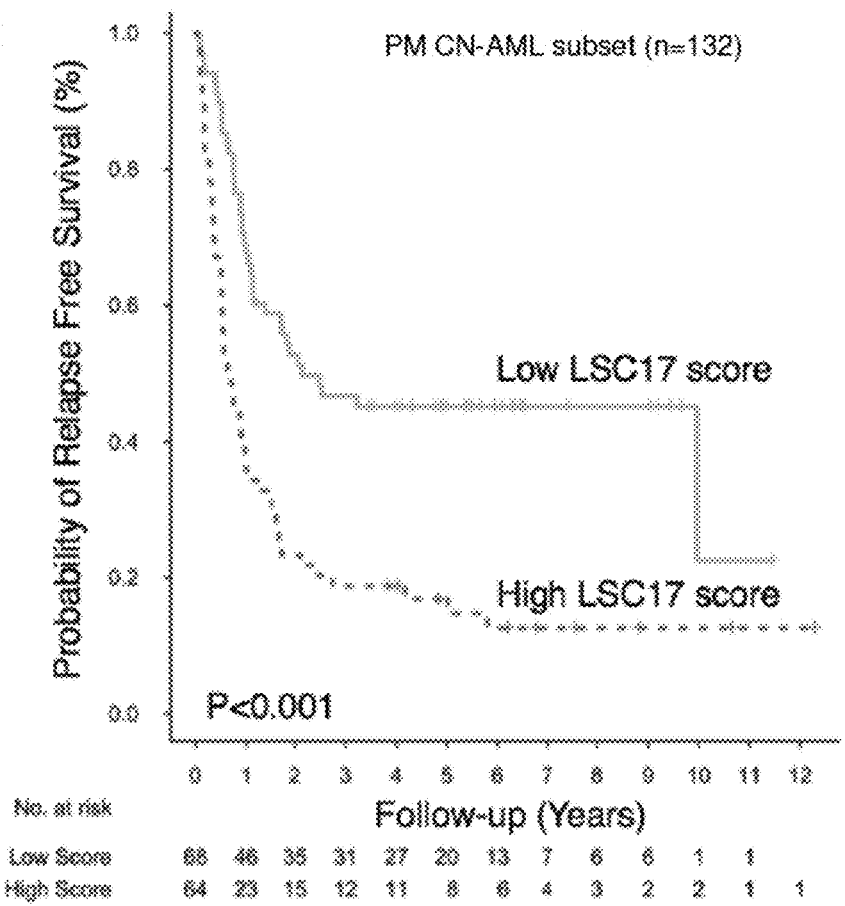

A signature score (LSC17) was calculated for each patient as a linear combination of GE weighted by regression coefficients that were estimated from the training data as follows: LSC17 score=(DNMT3B×0.0874)+(ZBTB46×−0.0347)+(NYNRIN×0.00865)+(ARHGAP22×−0.0138)+(LAPTM4B×0.00582)+(MMRN1×0.0258)+(DPYSL3×0.0284)+(KIAA0125×0.0196)+(CDK6×−0.0704)+(CPXM1×−0.0258)+(SOCS2×0.0271)+(SMIM24×−0.0226)+(EMP1×0.0146)+(NGFRAP1×0.0465)+(CD34×0.0338)+(AKR1C3×−0.0402)+(GPR56×0.0501). Above-median scores were associated with adverse cytogenetic and molecular risk, while sub-median scores were associated with favorable risk (FIG. 6). Thus, a median threshold was used to discretize scores into high and low groups.

An optimized sub-signature was identified by applying the above described regression procedure to CN-LMR cases (n=44, defined by presence of NPM1 mutation and no FLT3-ITD) with OS of at least 1 month from GSE6891, while restricting the analysis to the 17 signature genes. A new equation resulted for computing CN-LMR patient-specific risk scores (LSC3): LSC3 score=(DPYSL3×0.3)+(AKR1C3×−0.0477)+(NYNRIN×0.194).

Similarly, a retrained treatment response score was derived by applying the above described regression workflow to a randomly chosen half of the PM cohort. A score comprising 6 of the 17 signature genes resulted: −6.58+(MMRN1×0.04)+(KIAA0125×0.08)+(CD34×0.10)+(GPR56×0.20)+(LAPTM4B×0.16)+(NYNRIN×0.12).

Signature Testing: Microarray Data Processing and Analysis

The LSC17 score was validated against 3 published clinically annotated microarray cohorts with available GE data (2 from GSE12417[S12], 1 from TCGA[S13], Tables S3-S5), while the LSC3 score was tested on 1 independent CN-LMR cohort (GSE15434[S14], Table S6). Treatment protocols and the criteria used for cytogenetic/molecular risk classification for each cohort have been previously described[S12-14]. Raw Affymetrix CEL files (generated on the HG-U133 A, B, and Plus 2.0 arrays) containing GE data for 2 independent cohorts of CN-AML cases[S12] were downloaded from GEO with accession code GSE12417 and clinical annotations were provided by the authors. Of the 163 GE profiles in GSE12417 CN-AML cohort 1, we removed 2 PB samples, 1 MDS-RAEB case and 4 cases with missing clinical data, leaving 156 BM samples for analysis. For this cohort, the GE data generated on the U133A and B arrays were merged. The same inclusion criteria for analysis was applied to the 79-patient GSE12417 CN-AML cohort 2 of this dataset leading to the removal of 1 MDS case, 5 PB samples, and 3 cases due to missing clinical data, leaving 70 samples for analysis. Raw Affymetrix CEL files (generated on the HG-U133 Plus 2.0 array) containing GE data of a third independent cohort of de novo cytogenetically heterogeneous AML patients[S13] were downloaded from TCGA AML data portal (183 cases). An additional dataset of 70 CN-LMR HG-U133 Plus 2.0 array profiles was downloaded from accession GSE15434 to validate the LSC3 CN-LMR specific signature scores, with clinical data provided by the authors[S14.] All microarray data were processed as described for the training dataset GSE6891. Signature scores (either LSC17 or LSC3) were determined for each patient in the microarray validation cohorts using the signature gene importance weights derived during training and a median threshold. The scores were then subjected to survival analyses to assess their prognostic value in each cohort.

Signature Testing: RNA-Seq Data Processing and Analysis

179 GE profiles normalized to reads per kilobase of transcript per million mapped reads (RPKM) that were originally derived from the Illumina GA-IIX platform's raw data were downloaded from the TOGA AML data portal. Of these, 169 profiles also had microarray data that was used for signature validation. To test whether the LSC17 scores as computed using RNA-Seq data had prognostic value comparable with that of the corresponding microarray-data-derived scores for this cohort, these 169 profiles were considered for further analysis. To ensure comparability between the microarray GE levels used to train the signature and the RNA-Seq data used to test it, a value of 1 was added to the RPKM values before applying a log-transformation to the base-2 scale to ensure non-negative $\log_2$ expression levels. Additionally, where there was more than one entry per gene in the gene-summarized RPKM profiles, the entry with the maximum mean GE across the TOGA AML profiles was retained for computing per-patient LSC17 scores for use in survival analysis.

NanoString Assay Design and Expression Profiling

We submitted the 17 Affymetrix probeset identifiers making up our signature along with the identities of 9 reference genes to NanoString Technologies[S16] for custom codeset creation (Table S8). The reference genes were chosen to cover a wide range of expression levels in AML[S17]. The 100mer NanoString probes were fabricated to overlap or be proximal to the corresponding Affymetrix probe target regions. The National Center for Biotechnology Information nucleotide-nucleotide Basic Local Alignment Search Tool algorithm[S18] (and the HG19/GRCh37+ transcripts database) was used with default settings to confirm agreement between Affymetrix and NanoString probe targets.

We used a total of 32 NanoString cartridges implementing this codeset design, each of which comprised 12 lanes. The first 11 lanes of each cartridge were used to measure GE from 11 RNA samples, while the last lane was reserved as a control against which the GE across all cartridges were normalized, in order to minimize inter-cartridge variability as described by others[S19;S20.] An equal parts mixture of 26 synthetic 100 bp DNA oligonucleotides (Integrated DNA Technologies) at a concentration of 1.8 pM per oligonucleotide was placed in the control lane of each cartridge. The oligonucleotides were designed to resemble the target transcripts that the codeset was designed to hybridize with.

RNA extraction and quality assessment protocols used in this analysis are described elsewhere[S1]. Either 100 ng, 150 ng, or 250 ng of RNA per sample was used to determine the GE levels of the 17 signature and 9 reference genes using the custom NanoString codeset. Total RNA (5 μL) was incubated with 20 μL of reporter probe and 54 of capture probe mix (supplied by the manufacturer) at 65° C. for 16 to 24 hours for hybridization to take place. The reaction was processed on the nCounter Prep Station (Version 4.0.11.1), while excess probes were washed out using a 2-step magnetic bead-based purification strategy. First, magnetic beads with short nucleic acid sequences complementary to the capture probes are bound to the target/probe complexes in the hybridization mixture. Excess unbound reporter probes and non-target transcripts are then removed. Next, the capture probes and target/probe complexes are eluted off the beads and are re-bound to other magnetic beads with nucleic acid sequences that are complementary to reporter probes. Excess unbound capture probes are removed from the mixture before the purified target/probe complexes are eluted off the beads and immobilized on the NanoString cartridge for data collection. Transcript counts were determined using the nCounter Digital Analyzer (Version 2.1.2.3) at the high-resolution setting. Specifically, digital images were processed with final barcode counts tabulated in reporter code count (RCC) output files containing comma-separated values (CSV).

Signature Testing: NanoString Data Processing and Analysis

The NanoString assay was performed on 307 diagnostic AML samples from the PM Cancer Centre Tissue Bank collected from patients treated with curative intent between 1999 and 2012 (Table S7). Patients were excluded if they received any cytoreductive treatment other than hydroxyurea or died within one month of starting therapy. RCC files containing raw transcript counts from each cartridge were analyzed using the nSolver analysis software (version 2.0.72) for quality control (QC) and normalization purposes using default settings for GE analysis. Specifically, RCC files for each cartridge along with a reporter library file, which contains probe annotations for our codeset, were imported into nSolver. The software normalized the captured raw counts to the geometric mean of the 9 reference genes included in our assay and the codeset's internal positive controls, while checking for imaging, binding, positive spike-in, and normalization quality. The control lane of each cartridge, which held predefined quantities of synthetic oligonucleotides, were processed in the same manner as the RNA lanes using the nSolver software without normalization to reference genes.

The output files from nSolver were read into R for further QC, normalization, and data processing. An RNA input correction step was used to adjust the GE counts of each cartridge to the reference amount of 100 ng RNA. The control lanes for cartridges 1 to 3 were used as blank lanes to estimate per-probe background noise. We found that none of the 17 signature or 9 reference probes exhibited high background counts (i.e., the GE of each probe were not significantly above 3 standard deviations over the codeset's true background in the blank lanes, computed as the geometric mean of the codeset's 8 negative control probes) and thus no background subtraction was required for our codeset. In lanes where RNA was present, all signature and reference probe counts were expressed well above 3 standard deviations over background. The coefficient of variation (CV, standard deviation divided by mean GE) and maximum fold change (MFC, maximum divided by minimum GE) were the measures used to quantify GE variation. All reference genes had lower CV and MFC values compared to the signature genes and most control probes while spanning a sufficiently large range of signature probe GE, attesting to their suitability for use as control genes in this assay.

Since cartridges were processed on different days, we reserved 1 lane of each cartridge as a control as previously discussed. This strategy allowed us to minimize technical sources of variation between cartridge runs including differences in binding efficiency, and will be especially useful for ensuring that GE measurements in this study are comparable to data derived from cartridges used to assay additional independent AML samples in future studies. In this study, we prepared oligonucleotide control lanes for different cartridge subsets on separate days. We therefore needed to account for apparent batch effects observed in the control lanes of the cartridges before we could use them to batch-correct RNA counts. To batch-correct the oligonucleotide counts, multiplicative corrective constants were computed and applied to each batch of control lanes according to the oligonucleotide preparation schedule (i.e., cartridges 4, 5 to 11, 12 to 19, 20 to 27 and 28 to 32 represent the batches of oligonucleotides prepared on separate days). Specifically, the oligonucleotide counts of each batch of control lanes were scaled by a ratio of geometric means between the oligonucleotide counts in each batch and that of all control lanes. We next used the batch-corrected control lanes to minimize inter-cartridge technical variation in RNA counts. The geometric mean of the corrected oligonucleotide counts in the control lane of cartridge 5 (arbitrarily chosen) was divided by the same summary value corresponding to each of the other cartridges to produce per-cartridge scaling factors. The RNA and oligonucleotide counts of each cartridge were then adjusted using these factors by means of multiplication, thereby minimizing batch induced GE variation.

With inter-cartridge GE variability minimized, a final round of normalization to the reference genes for each cartridge was performed to maximize GE comparability across all 307 lanes in the dataset. This step applies the inter-cartridge normalization procedure to the reference genes and mitigated, at least in part, potential batch effects that could not be minimized in cartridges 1 to 3 since they used blank control lanes to estimate probe background levels. Similar to the earlier described batch correction strategy, the GE counts in the RNA lanes of each cartridge were adjusted using a ratio of geometric means between the reference gene counts in each cartridge and that of all 32 cartridges.

As with the treatment of RNA-Seq data, the fully normalized GE counts were $\log_2$-transformed after incrementing all counts by 1 to ensure non-negative expression values and compatibility with the LSC17 scores that were derived from $\log_2$ microarray GE data. Signature scores (either LSC17 or LSC3) were computed for each patient using the scaled data and submitted for survival analysis.

PM Cohort Treatment Details

All patients received induction chemotherapy with a 3+7 backbone (daunorubicin 60 mg/m$^2$ IV daily×3 days with cytarabine (ara-C) 200 mg/m$^2$ via continuous IV infusion daily×7 days (dose reduced to 100 mg/m$^2$ for patients ≥60 years of age)). A minority of patients were enrolled in clinical trials employing 3+7 with gemtuzumab ozogamicin (n=7) or midostaurin (n=3). CR was defined as achievement of a morphological leukemia-free state (BM blasts <5% and absence of extramedullary disease) and recovery of PB counts (absolute neutrophil count ≥1.0×10$^9$/L and platelet count ≥100×10$^9$/L)[S24.] Barring contraindications, patients in CR went on to receive 2 cycles of consolidation chemotherapy (daunorubicin 45 mg/m$^2$ IV bolus daily×days 1 & 2 with ara-C 3 g/m$^2$ q12h days 1, 3 & 5, dose was reduced to 1.5 g/m$^2$ for patients ≥60 years of age). Patients with core binding factor leukemia received 1 cycle of this consolidation followed by 2 cycles of ara-C (3 g/m$^2$ q12h days 1, 3 & 5). For APL patients, induction and the first consolidation cycle included all-trans-retinoic acid (ATRA) 45 mg/m$^2$ daily in 2 divided doses×28 days, daunorubicin 60 mg/m$^2$ IV bolus daily×3 days and ara-C 100 mg/m$^2$ via continuous IV infusion daily×7 days. The second consolidation cycle included ATRA×28 days, daunorubicin 45 mg/m$^2$ IV bolus daily for days 1-3 and ara-C 1.5 g/m$^2$ q12h on days 1, 3 & 5. For patients ≥60 years of age with WBC count <10, ara-C was omitted from induction and consolidation. For APL patients with initial WBC count <10, maintenance therapy consisted of ATRA 45 mg/m²/d×7 days on alternating weeks×9 months. For all others, maintenance involved 21 monthly cycles of 6-mercaptopurine 75 mg/m²/day orally daily for 21 days and methotrexate 20 mg/m²/day orally once weekly; every other cycle included ATRA 45 mg/m²/d×14 days. allo-SCT was performed in CR1 for high-risk patients, typically those with secondary AML, adverse cytogenetics, or normal karyotype with poor prognostic molecular features (FLT3-ITD positive; NPM1 mutation positive/FLT3-ITD negative). Prerequisites for allo-SCT included disease remission, age less than 71, a lack of significant comorbidities and good performance status.

Statistical Analysis

LSC signatures were trained by regression analysis using microarray data from a published cohort of 495 subjects with de novo AML comprising all cytogenetic risk groups, treated with curative intent (GSE6891[25]). For signature validation we used microarray and RNA-seq data from independent AML cohorts (GSE12417[26], TCGA[27], and GSE15434[28]) and NanoString data from the PM cohort.

Each LSC signature gene was assigned a regression coefficient, and a score was calculated for each patient in the validation cohorts as the weighted sum of GE of signature genes. The 17-gene signature (LSC17) was re-trained for CN-LMR patients in the GSE6891 cohort to obtain an optimized re-weighted sub-signature comprising 3 of the LSC genes (LSC3). Scores above or below the median of each validation cohort were classified as high or low, respectively. Survival differences between these high- and low-score groups were estimated using uni- and multi-variate survival analyses based on KM and Cox proportional Hazards (CPH) models.

Predictive-ness of the LSC17 score for therapy resistance was quantified by logistic regression analysis using bootstrap-adjusted AUROC.

AML GE profiles were compared to those of stem and progenitor cell types purified from human umbilical cord blood (hUCB) (GSE24759[29] and GSE42414[30]) using the Perturbation model[31], which estimates the relative proportions of global GE patterns corresponding to multiple blood cell types composing a heterogeneous mixture.

Supplemental—Statistical Analysis

All statistical analyses were performed in R 3.1.0, where a P value of less than 0.05 indicated statistical significance. The Spearman rank method of correlation was used unless specified otherwise. Various two-tailed tests were used to evaluate the differences in baseline clinical characteristics between patients with high versus low LSC17 scores as indicated. OS was defined as the time from AML diagnosis until death from any cause or last clinical follow-up. EFS was defined as the time from AML diagnosis until an event (defined as induction failure, relapse or death from any cause) or last follow-up. RFS was defined as the time from the date of achievement of first remission until relapse or death (regardless of cause) or last clinical follow-up[S24]. Univariate survival analysis was performed using the KM and CPH models with comparisons performed using Mantel-Cox log-rank tests. For multivariate analyses, covariates for the CPH model included signature scores (either LSC17 or LSC3) as well as established clinical risk factors (i.e., age, WBC count at diagnosis, de novo vs. secondary AML onset, MRC cytogenetic risk group, and NPM1 and FLT3-ITD mutational status). Wald's test was used to evaluate the significance of hazard ratios (HR) and violation of the proportional hazards assumption was detected by examining Schoenfeld residuals, and eliminated by setting offending parameters as stratifying variables in the model as described by others[S12;S13]. TTR was assessed by cumulative incidence analysis with death as a competing risk, and used Gray's test for subgroup comparisons[S25]. All survival analyses were performed using the survival 2.38-1 R package[S26]. In the comparison to phenotypic signatures, custom CDFs (described previously) were used to summarize microarray probe expression for each gene, since higher HRs resulted compared to scores computed using array probes per gene with maximum average GE in GSE6891.

In analyses assessing prediction of treatment response, uni- and multi-variate logistic regression models were used with the bootstrap-adjusted AUROC metric to determine the ability of various clinical parameters and GE scores to predict initial induction response. The rms 4.4-1 R package was used for logistic regression analysis, while the pROC 1.8 and PredictABEL 1.2-2 R packages[S21;S22] were used for ROC curve analyses. Relative importance of individual covariates in multivariate logistic regression models was estimated by examining the partial Wald Chi-squared statistic[S23].

Results and Discussion

Figure 4A:
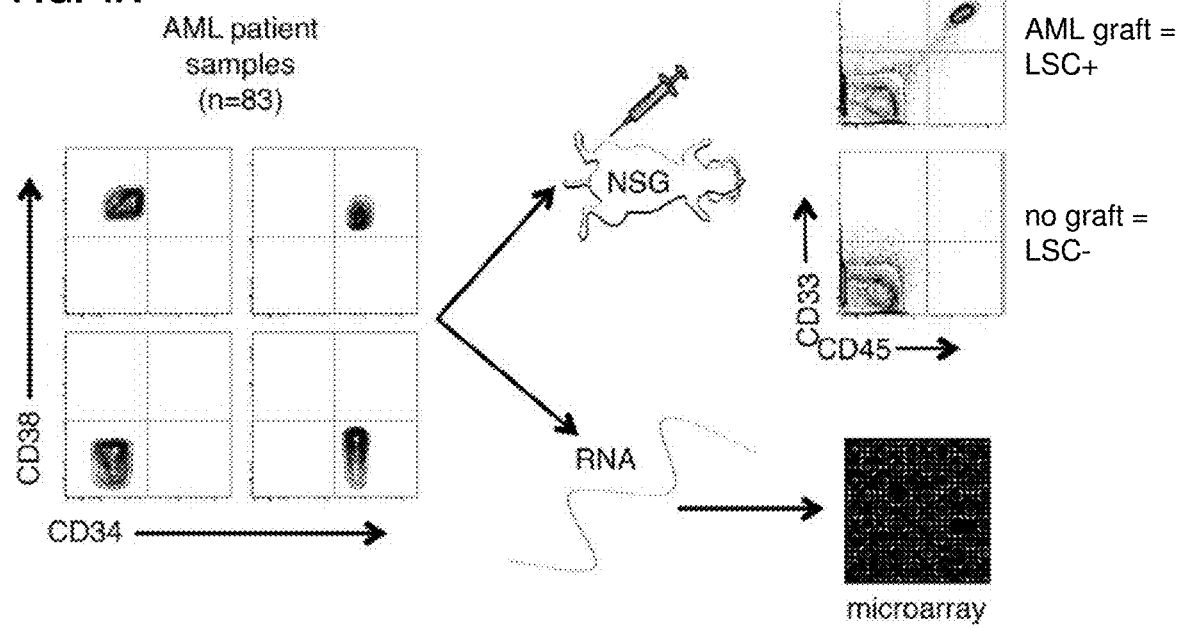
FIG. 4 shows Determination of Leukemic Engraftment Ability in Cell Fractions From AML Patient Samples. Panel A shows a schematic of the experimental protocol. Patient samples were fractionated based on surface expression of CD34 and CD38. Each cell fraction was transplanted into NOD.SCID.IL2R$\gamma^{null}$ (NSG) mice to determine ability to generate leukemic grafts. In parallel, RNA was extracted from each cell fraction for GE measurement by microarray. Panel B shows the number of functionally-defined LSC+ and LSC− fractions in each sorted cell population that were used for analysis. Panel C shows a summary of the fractions that were included in the analysis. Each line represents fractions sorted from one patient sample. Fractions labeled as N/A (white) were not included in the analysis due to insufficient cell numbers for xenotransplantation and/or insufficient RNA.
Figure 4B:
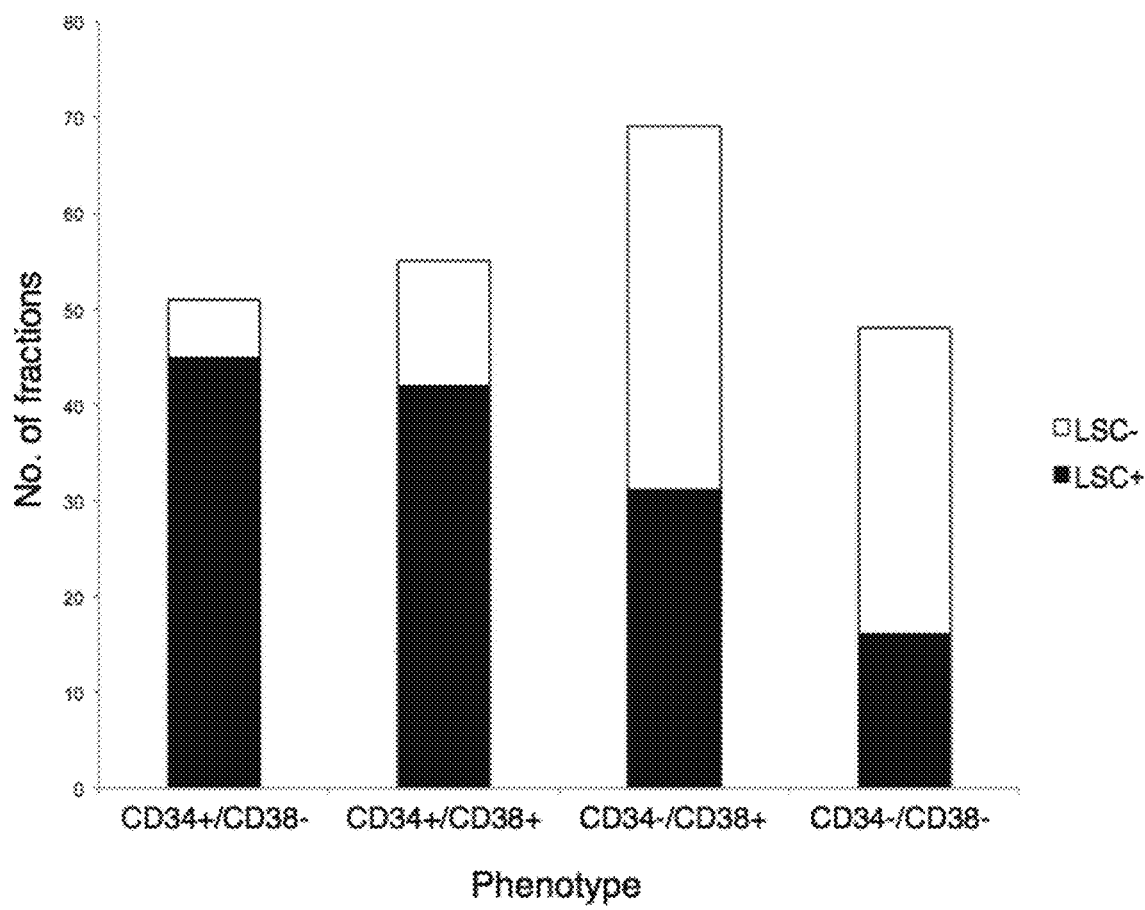
Figure 4C:
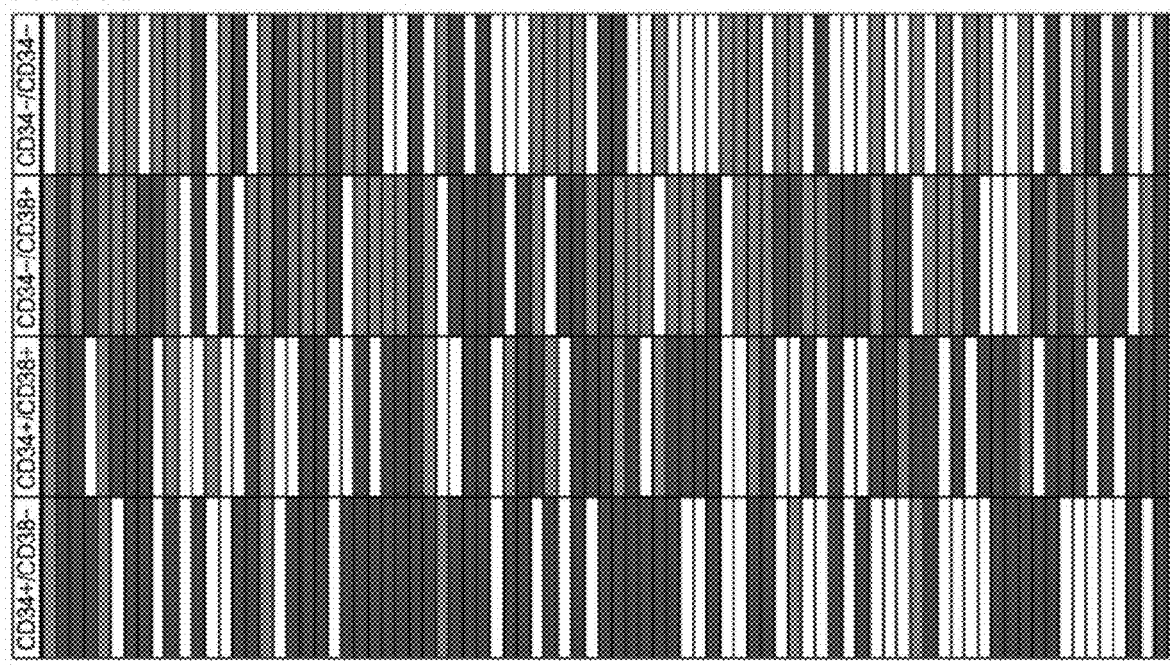

Characterization of LSC-Specific Gene Expression Patterns 83 samples obtained from 78 AML patients were sorted into fractions and tested for LSC activity by xenotransplantation (FIG. 4A). Consistent with previous reports, the majority of CD34+ and a minority of CD34− fractions contained LSCs[17;18]. Furthermore, LSCs were detected in fractions of all CD34/CD38 phenotypes (FIG. 4B-C), underscoring the importance of performing functional assays to define LSC activity.

Figure 1B:
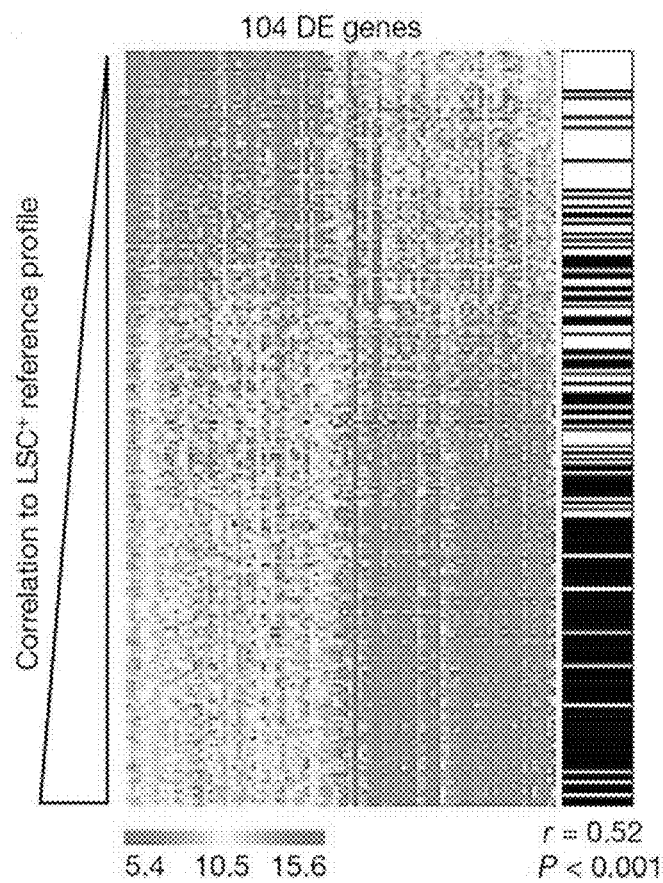
Figure 1C:
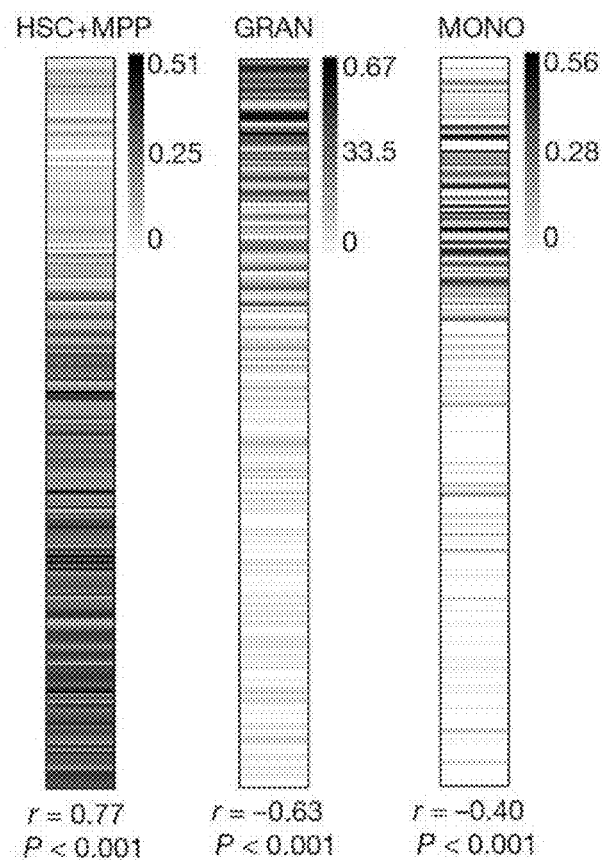

Each of the functionally-defined 138 LSC+ and 89 LSC− fractions was subjected to Illumina microarray GE analysis. GE values were compared between the LSC+ and LSC− fractions to obtain a list of DE genes. 104 genes exhibited at least a 2-fold expression level difference between the 2 groups with an adjusted P value of <0.01 (FIG. 1A, Table S8). We defined an LSC+ reference profile as the average expression levels of these 104 genes in the LSC+ fractions. There was a strong correlation between engraftment ability of individual cell fractions and their GE similarity to the LSC+ reference profile, as well as to the global GE profiles of normal hematopoietic stem cells (HSC) and multi-potent progenitors (MPP) from hUCB[30] (FIGS. 1B and C). Conversely, GE similarity to the LSC+ reference profile was anti-correlated with the global GE patterns of mature myeloid cell-types including granulocytes and monocytes[29] (FIG. 1C). These findings suggest that the 104 most DE genes between LSC+ and LSC− cell populations are associated with stem cell transcriptional programs that are shared between LSC and normal HSC/MPP.

Derivation of a 17-Gene LSC Signature Score

Figure 1D:
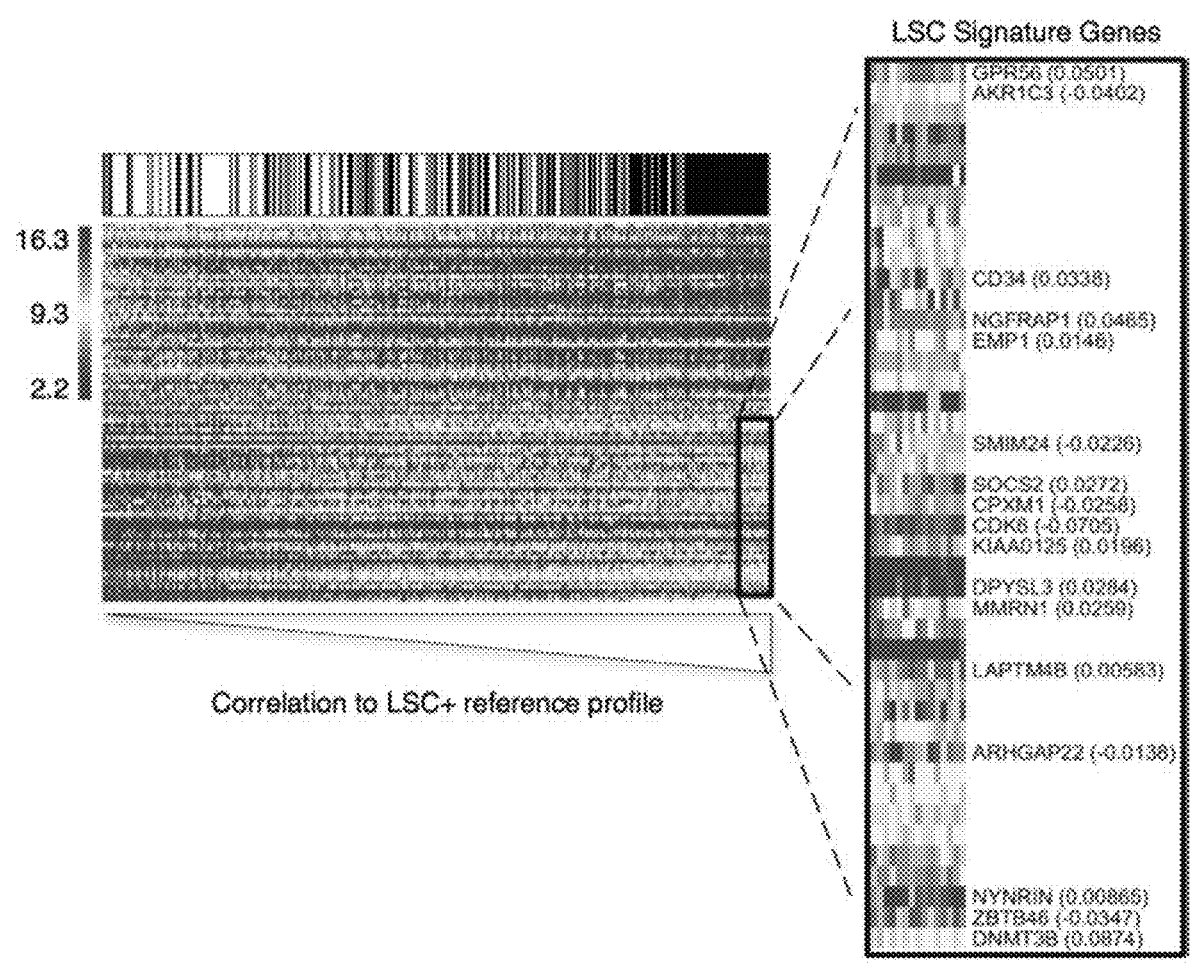

To identify a core transcriptional program regulating functional LSCs that is correlated to survival outcome in AML, we interrogated a published dataset of 495 AML patients[25] (GSE6891) in which 89 of the 104 DE LSC genes were captured (FIG. 1A). Expression of the 89 genes in these unfractionated patient samples was variable and showed a similar pattern of correlation to the LSC+ reference profile as did the sorted LSC+ and LSC− fractions, suggesting that LSC-associated GE programs are detectable at the bulk cell level (FIG. 1D). We applied a sparse statistical regression algorithm[32;33] to relate GE to patient survival in this training cohort using either the full list of 89 LSC genes, or the subset of 43 genes that were more highly expressed in LSC+ fractions; analysis of the latter subset yielded an optimal 17-gene signature. A score, which we term the LSC17 score, could be calculated for each patient as the weighted sum of expression of the 17 signature genes (FIG. 1D, Table S8). High LSC17 scores were strongly associated with poor OS and EFS (Table S2). In addition, patients with high LSC17 scores had significantly higher percentages of BM blasts at diagnosis, higher incidence of FLT3-ITD and adverse cytogenetics, higher rates of relapse, and lower response rates to standard induction treatment, reflecting an association between LSC properties and outcome.

Validation of the LSC17 Score in Independent AML Datasets

Figure 2A:
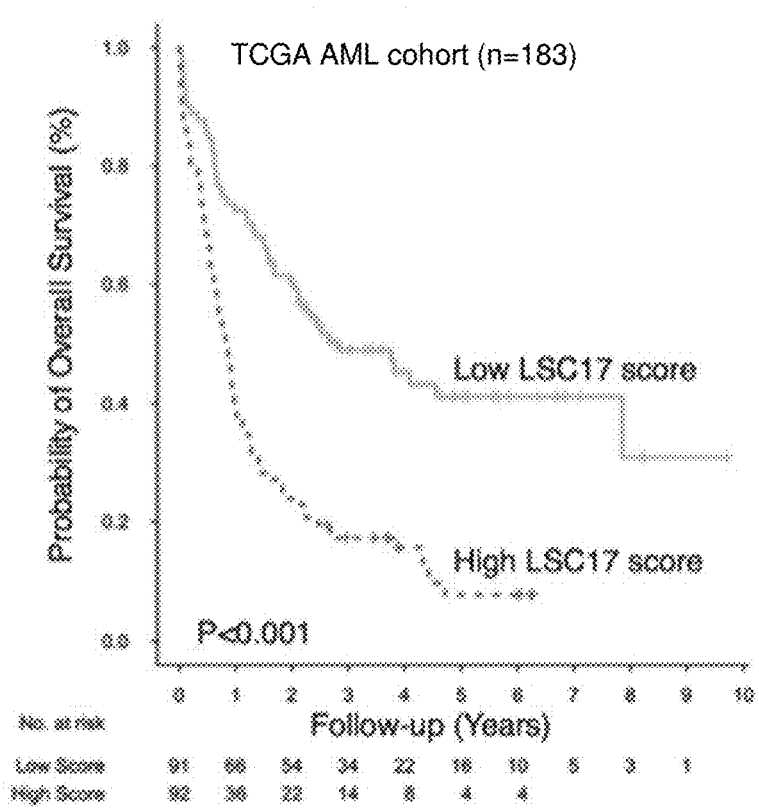
FIG. 2 shows LSC Signature Scores are Associated With Survival in Multiple Independent AML Cohorts Across GE Measurement Platforms. Panels A-D show Kaplan-Meier (KM) estimates of overall survival (OS) in several independent AML cohorts, according to LSC17 scores calculated using microarray GE datasets. Panels E and F show KM estimates of OS of total (Panel E) and CN-AML (Panel F) patients in The Cancer Genome Atlas (TCGA) AML cohort according to LSC17 scores calculated using RNA-Sequencing (RNA-Seq) data. Panel G shows KM estimates of OS of CN patients with low molecular risk features (CN-LMR, NPM1 mutations without FLT3-ITD) from GSE15434, according to LSC3 scores calculated using microarray GE data. For all panels, OS of patients with scores above and below the median in each cohort are shown by dotted and solid lines, respectively.
Figure 2B:
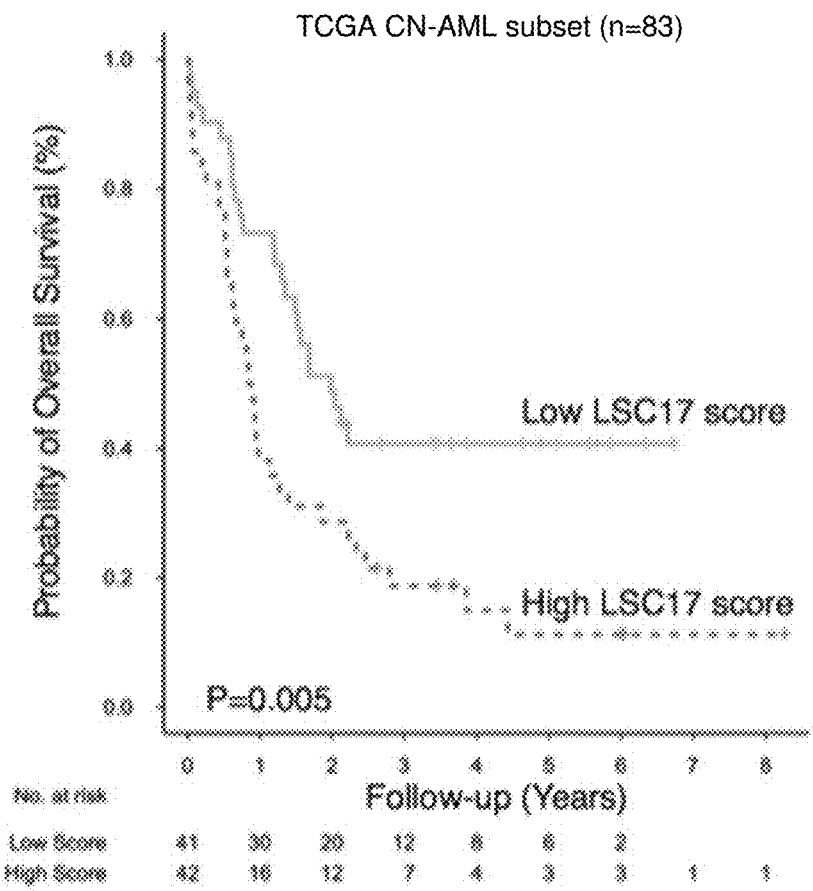
Figure 2C:
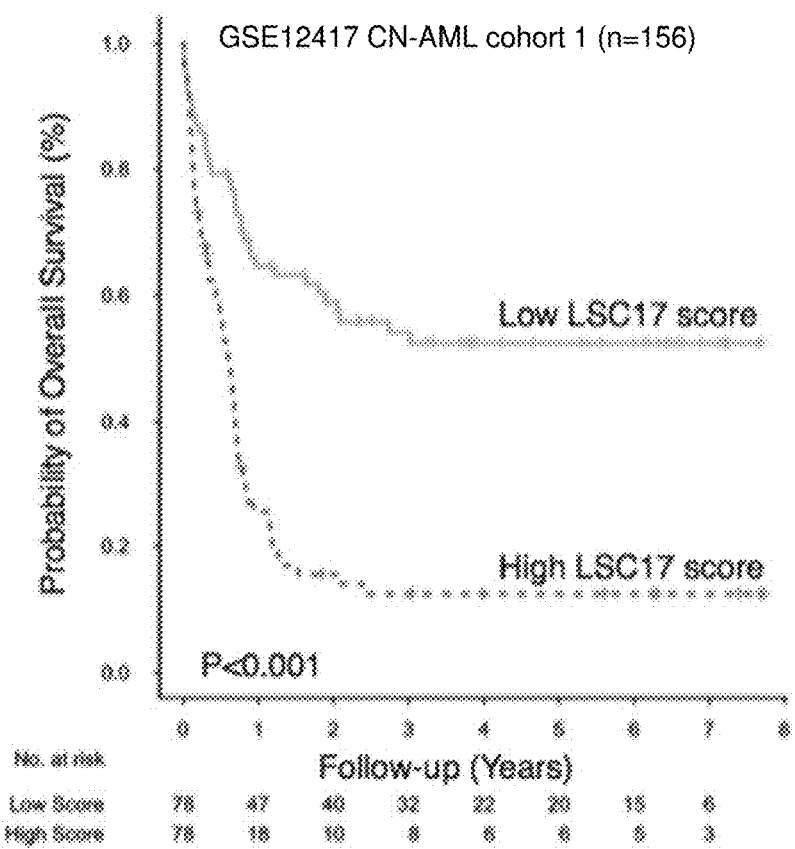
Figure 2D:
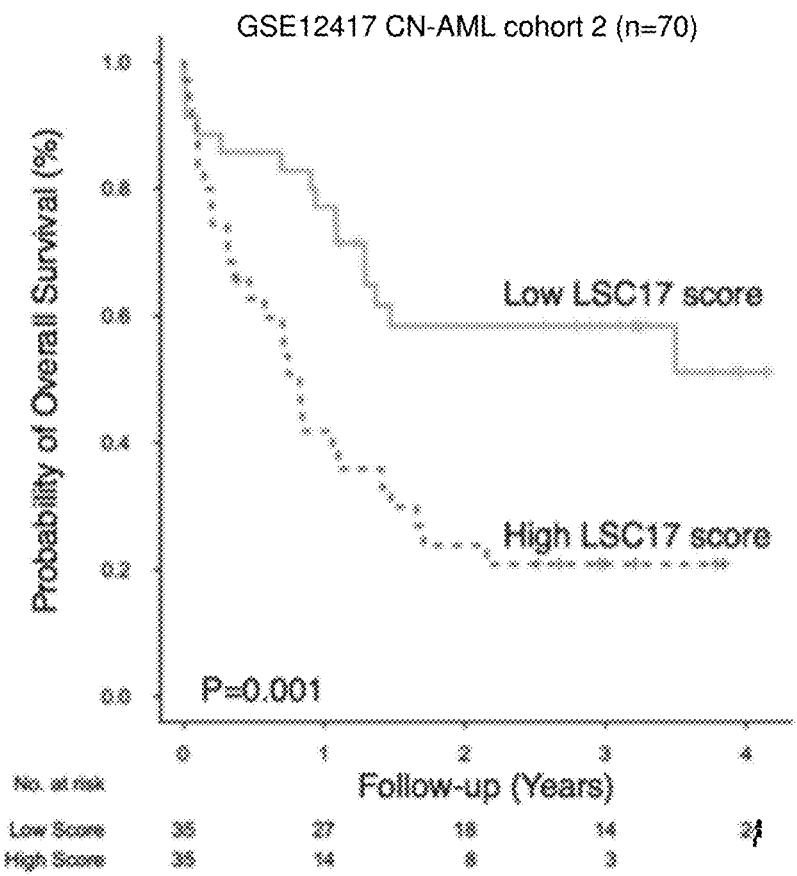
Figure 10:
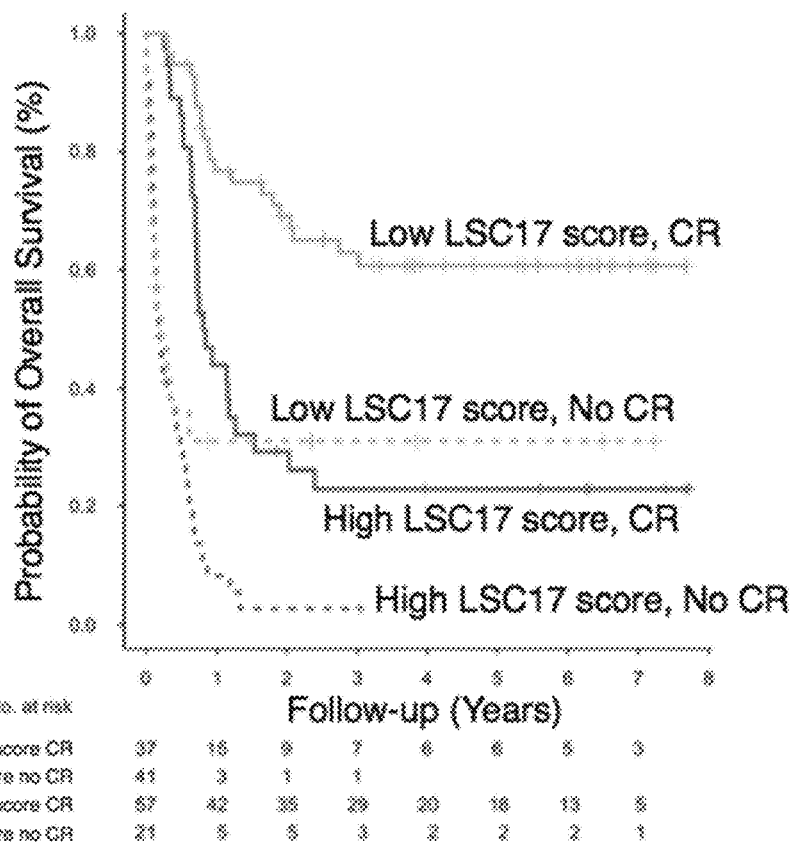
FIG. 10 shows High LSC17 Scores Are Associated With Poorer Treatment Response. KM estimates of OS in GSE12417 CN-AML cohort 1, according to LSC17 scores calculated using microarray GE data. OS of patients with scores above and below the median in the cohort are shown by the high and low score curves as labeled, respectively. Dotted and solid lines denote no remission and remission achieved after first induction treatment, respectively.

We evaluated the association of the LSC17 score with survival in 3 independent published AML cohorts for which microarray GE and outcome data were obtainable (2 from GSE12417[26], 1 from TCGA[27], Tables S3 to S5). In the TCGA AML cohort (n=183), patients with a high LSC17 score had significantly shorter OS than patients with a low score (FIG. 2A, Table S5, hazard ratio (HR)=2.62; P<0.001). This survival difference was also observed in CN-AML patients (n=83) (FIG. 2B, median OS 10.4 vs. 24.1 months; HR=2.06; P=0.006). Similar results were observed in two other CN-AML cohorts (GSE12417 cohort 1, FIG. 2C, Table S3, HR=3.16, P<0.001; GSE12417 cohort 2, FIG. 2D, Table S4, HR=2.66, P=0.002); in GSE12417 cohort 1, a high LSC17 score was associated with shorter OS regardless of whether or not remission was achieved (FIG. 10). Similar results were also found in a subset of patients, wherein said patients were less than 60 years of age at diagnosis (Data not shown).

Figure 2E:
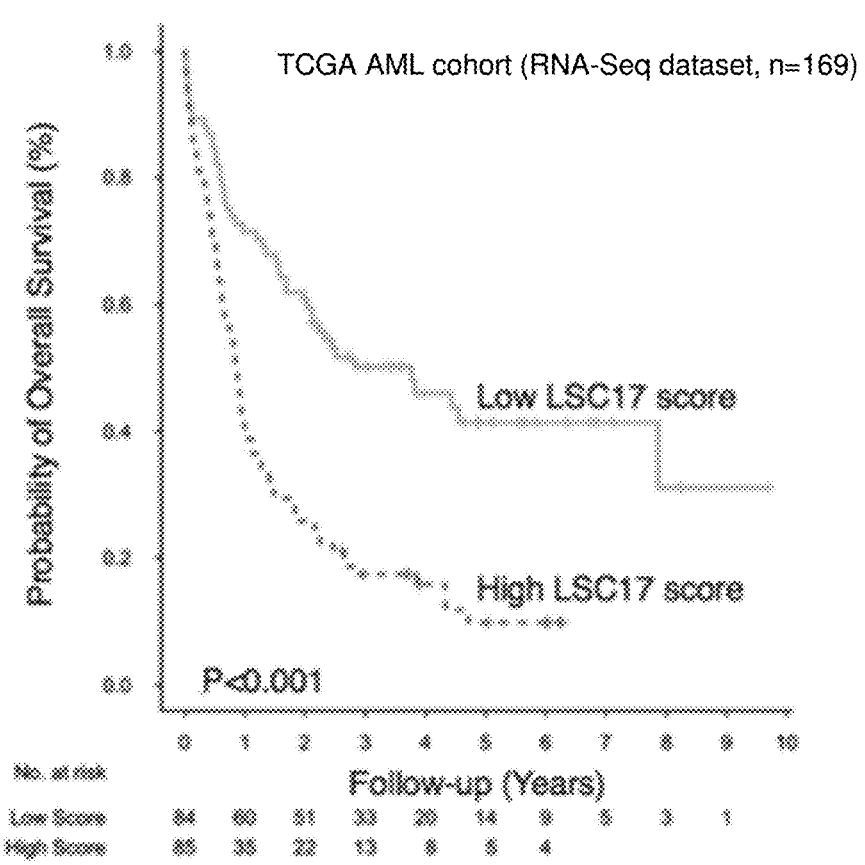
Figure 2F:
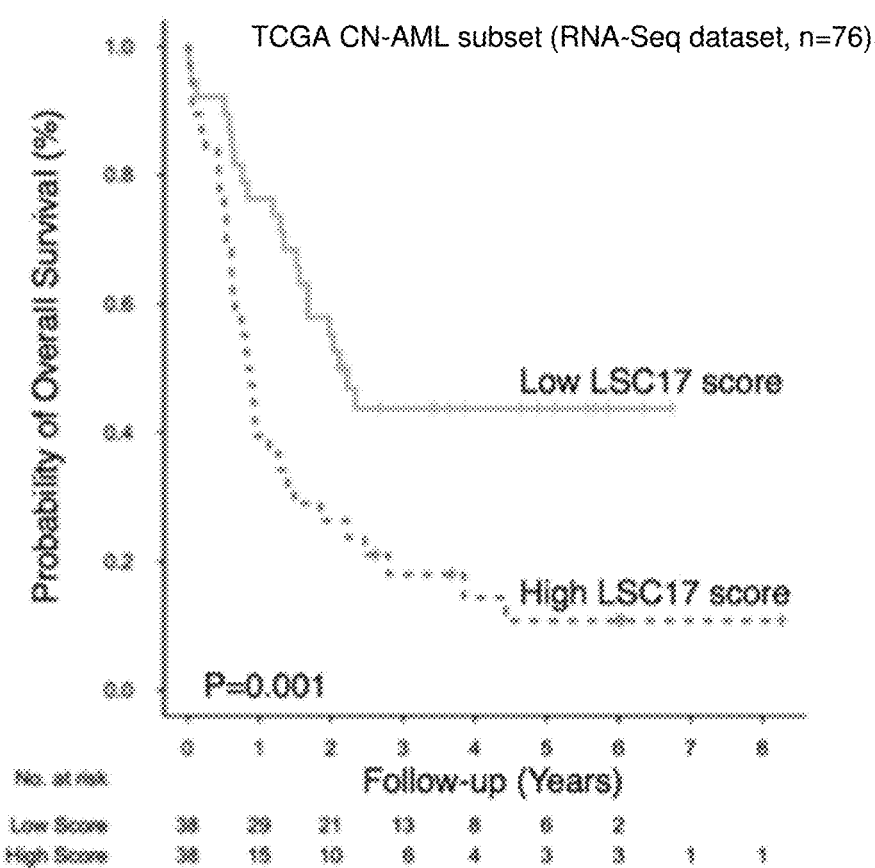

As in the training cohort, high LSC17 scores were significantly associated with adverse cytogenetic and molecular features, failure to achieve CR, and shorter EFS and RFS (FIGS. 7 and 8, Tables S3 to S5). When applied to RNA-Seq data for the TCGA cohort, the LSC17 score remained highly associated with outcome (All patients: FIG. 2E, HR=2.62, P=0.001; CN-AML subset: FIG. 2F, HR=2.06, P<0.006), demonstrating robustness across technology platforms.

In multivariate survival analysis using CPH models, the LSC17 score retained significant prognostic value in all tested cohorts independent of known predictors of outcome including patient age, WBC count, cytogenetic risk group, type of AML (de novo vs. secondary), and the presence of FLT3-ITD and NPM1 mutations (Tables 1, 2, and S9). The LSC17 score displayed superior prognostic accuracy over other published AML signatures that were derived from GE analysis of cell populations defined phenotypically or by multidimensional mass cytometry[34], demonstrating the power of approaches using cell fractions validated in stem cell assays[18] (Tables S10 and S11). Overall, the LSC17 score is strongly associated with survival post-treatment in multiple unrelated AML cohorts that include patients from the spectrum of currently employed risk categories.

Translation of the LSC17 Score to a Digital Counting Platform

To be applied clinically, a GE-based diagnostic test requires a technology that is reproducible, cost-effective, and has rapid turnaround time. The NanoString platform, on which an FDA-approved, commercially available prognostic gene signature assay for breast cancer has been implemented[35], fulfills these criteria and has a large dynamic range for GE measurement[36]. We therefore generated GE data using a custom NanoString assay for 307 AML patients treated at PM, and tested the ability of the LSC17 score to identify high-risk patients in this cohort.

Figure 3A:
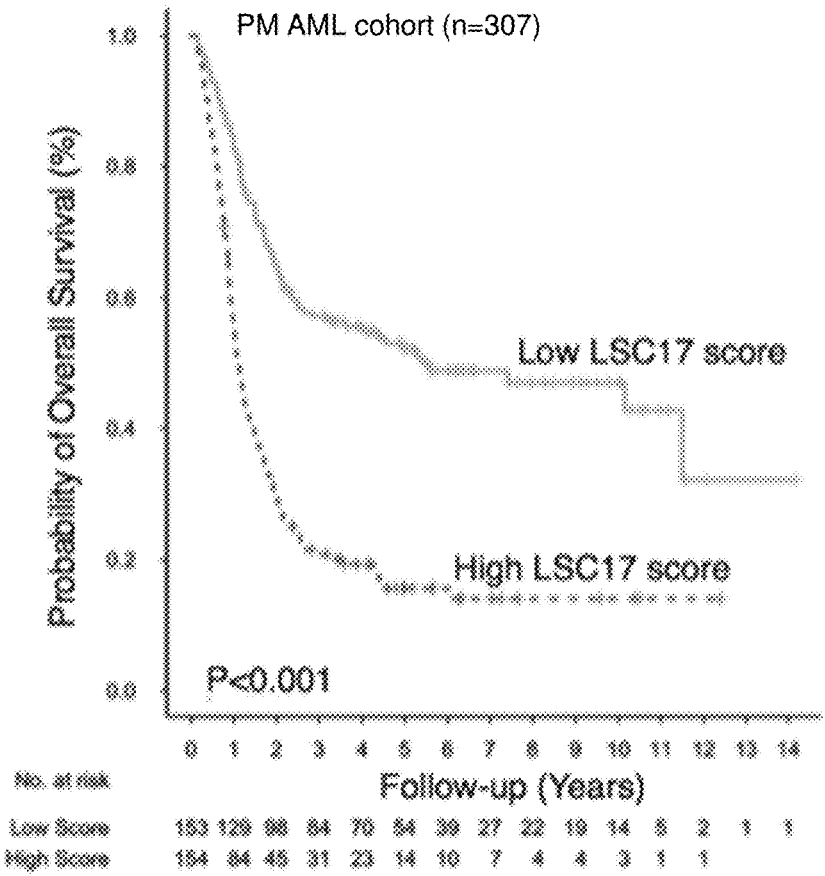
FIG. 3 shows LSC Signature Scores Measured by Digital Counting (NanoString) are Associated With Survival and Predict Therapy Resistance. KM estimates of OS in the Princess Margaret (PM) cohort according to LSC signature scores calculated using NanoString GE data. Panel A, entire cohort by LSC17 score; Panel B, entire cohort with one patient removed from analysis due to induction-related death, according to LSC17 score (high and low score as labeled) and whether or not remission was achieved after initial therapy (no remission, dotted lines; remission achieved, solid lines); Panel C, CN-AML cases according to LSC17 score; Panel D, CN-LMR cases according to LSC3 score. For Panels A-D, OS of patients with scores above and below the median in each cohort are shown by high and low scores as labeled, respectively. Panel E shows area under the receiver-operating characteristic curves (AUROC) curves for prediction of therapy resistance, using logistic regression models that include age, white blood cell (WBC) count, cytogenetic risk, and de novo vs. secondary AML as covariates, with (bottom line) or without (top line) LSC score. Panel F shows the predictive value (Chi-squared statistic) of each covariate for therapy resistance in the multivariate model. Panel G shows the AUROC curves for models that include age, WBC count, and de novo vs. secondary AML, plus either cytogenetic risk (bottom line) or LSC17 score (top line) as covariates.
Figure 3B:
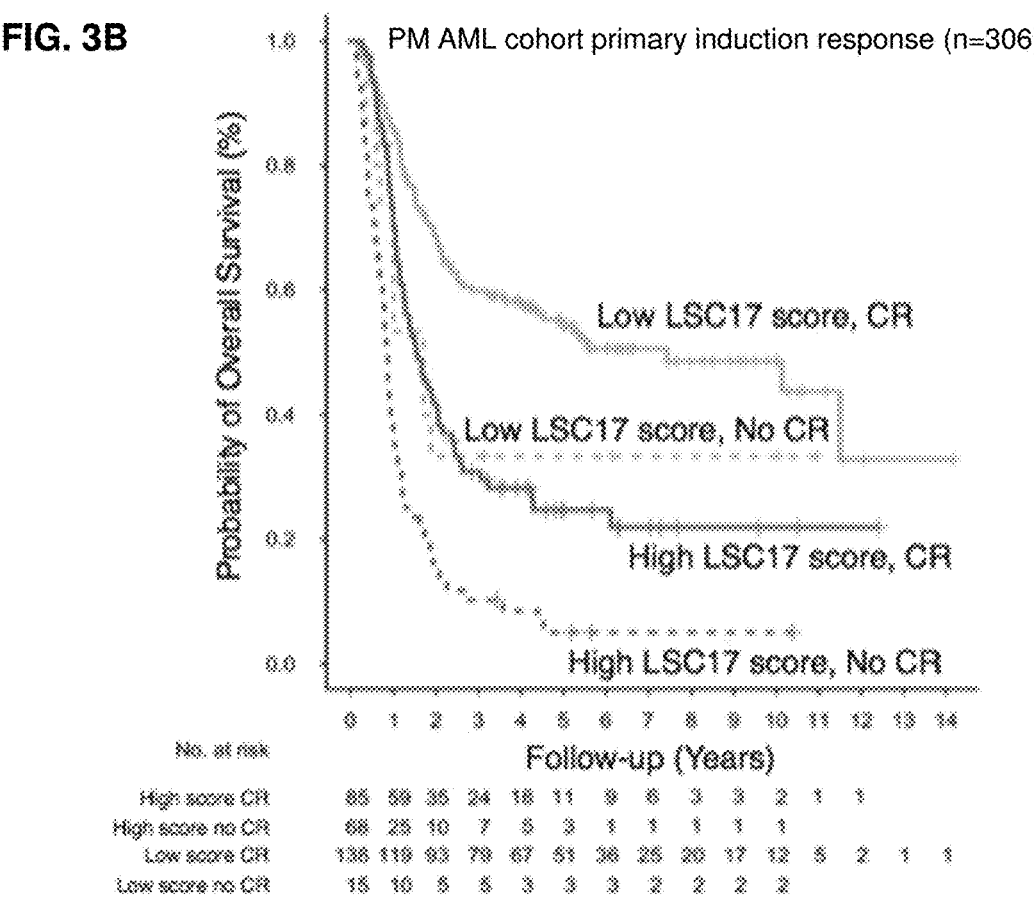
Figure 3C:
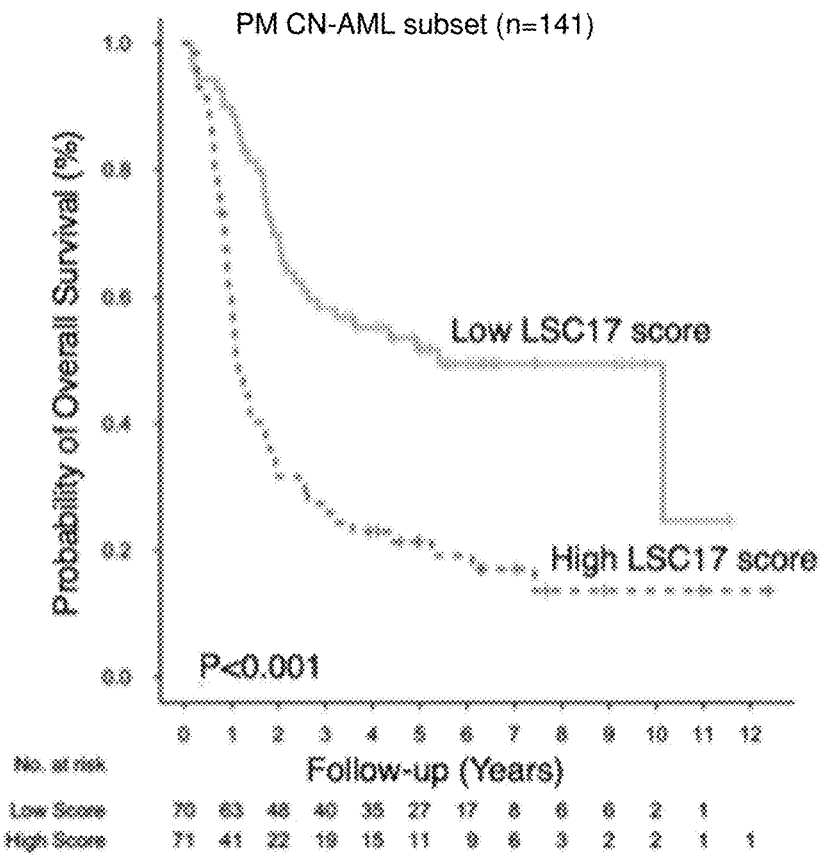
Figure 9A:
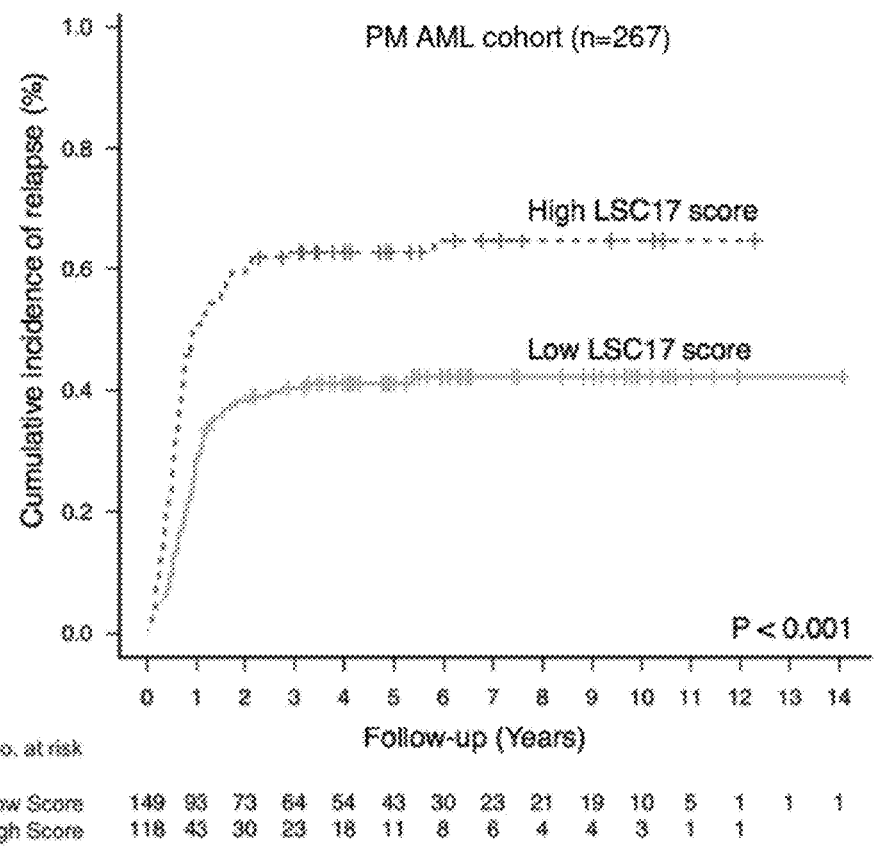
FIG. 9 shows High LSC17 Scores Are Associated With Shorter Time to Relapse. Panels A and B show estimates of TTR, according to LSC17 scores calculated using the NanoString GE dataset. For all panels, time to relapse (TTR) of patients with scores above and below the median in the cohort are shown by the dotted and solid lines, respectively.
Figure 9B:
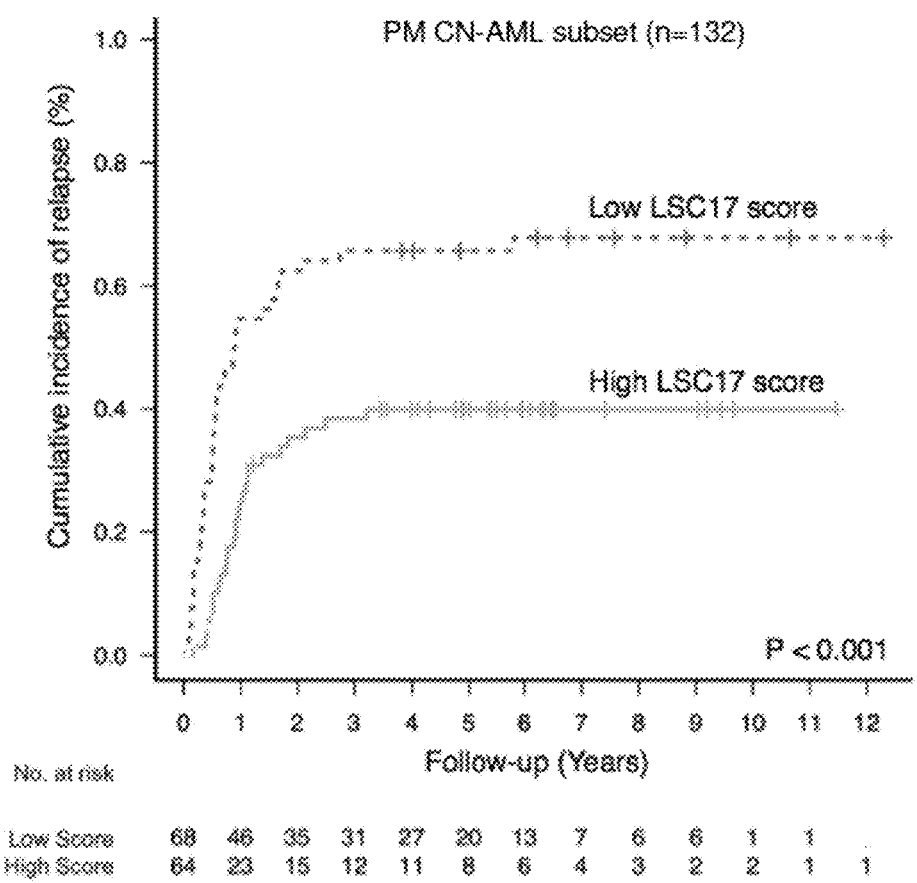

A high LSC17 score was associated with known adverse prognostic features including older age, high WBC count at diagnosis, and unfavorable cytogenetics (Table S7). As seen with all other cohorts tested in this study, patients with high LSC17 scores had significantly shorter OS than patients with low scores (FIG. 3A and Table S7, HR=2.73; P<0.001); this was true regardless of whether or not remission was achieved after primary induction therapy (FIG. 3B, CR: median OS 18.9 vs. 90.3 months; HR=2.18; P<0.001; no CR: median OS 10.5 vs. 20.7 months; HR=2.16; P=0.02). Similarly, a high LSC17 score was associated with shorter EFS, RFS, and TTR (Table S7, FIGS. 7 to 9). The association between a high LSC17 score and shorter OS was also observed in the subset of patients with CN-AML (FIG. 3C, median OS 13.7 vs. 65.7 months; HR=2.64; P<0.001). Importantly, in multivariate survival analysis including established risk factors, the LSC17 score retained independent prognostic value in both the full cohort as well as in the CN-AML subset (Table 1). Together, these results demonstrate the broad applicability and strong prognostic value of the LSC17 score on the clinically serviceable NanoString platform.

Optimization of the LSC17 Score for Patient Subsets: LSC3 Score for CN-LMR

Figure 2G:
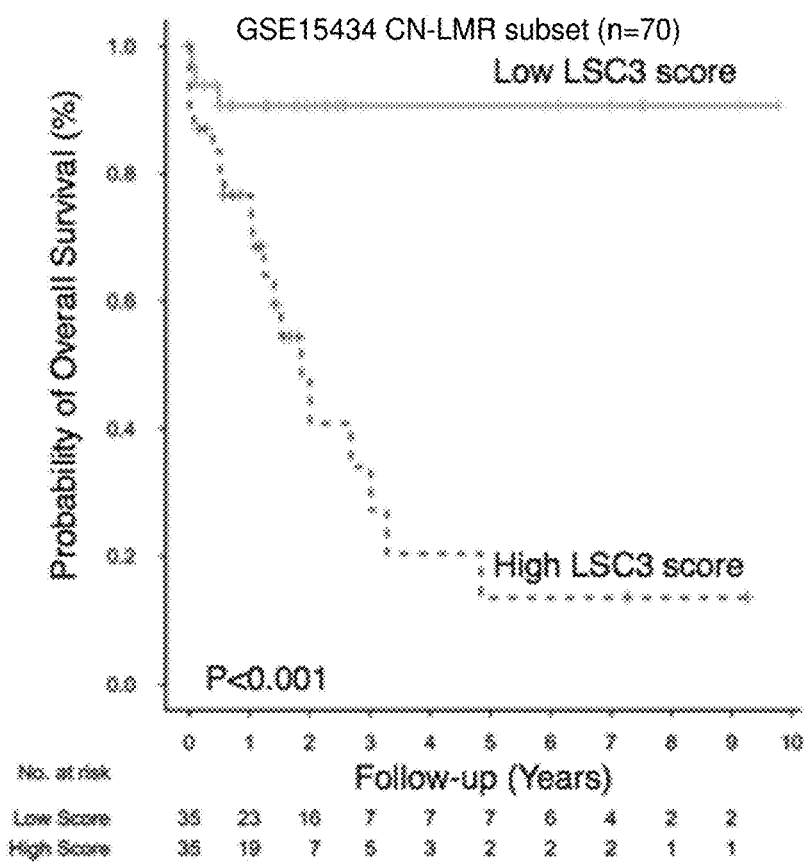
Figure 3D:
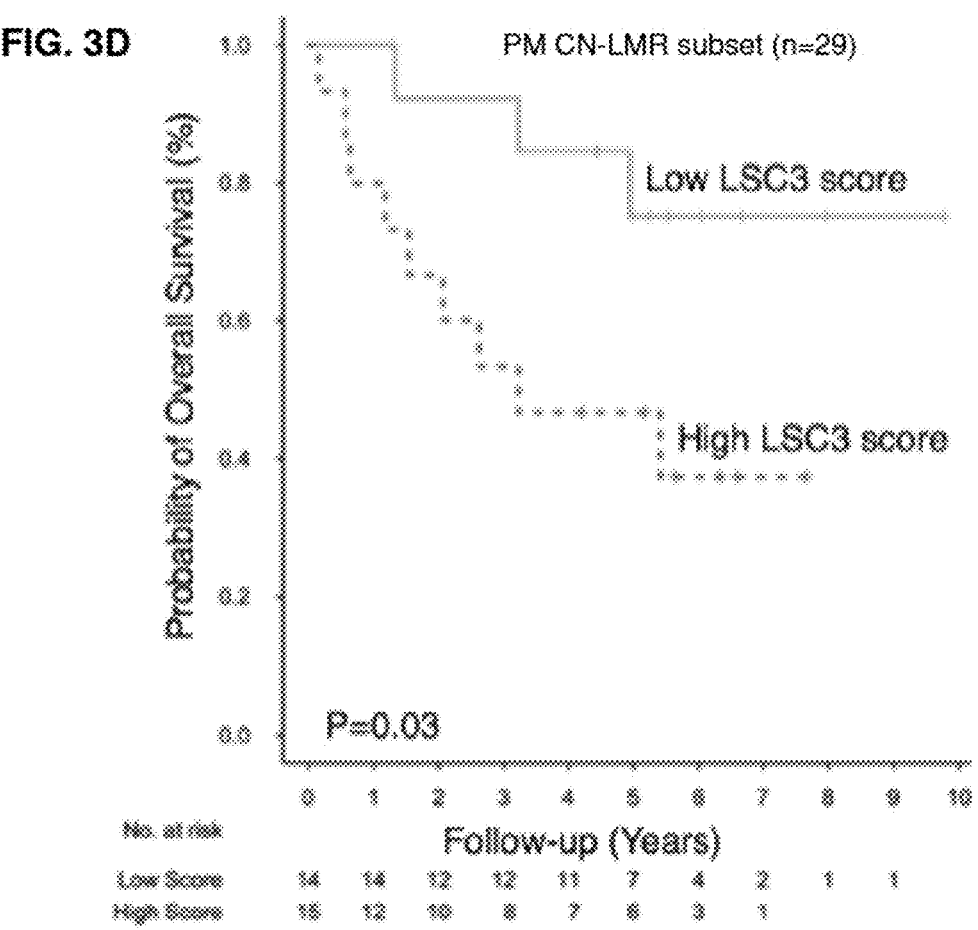

The LSC17 score was initially trained on GSE6891, which included only a small minority (n=44/495, 9%) of CN-LMR patients; as such, the score was not optimized for survival association when tested in the CN-LMR subset of GSE15434[28]. We therefore retrained the 17 LSC signature genes against OS of only the CN-LMR cases in GSE6891 and identified an optimized, re-weighted sub-signature in which only 3 of the 17 genes contributed to the calculated score (LSC3). A high LSC3 score was able to identify CN-LMR patients from GSE15434 with poor outcome (FIG. 2G, Table S6, HR=8.41; P<0.001), and was strongly associated with shorter survival in the subset of 29 CN-LMR cases in the PM cohort analyzed by NanoString methodology (FIG. 3D median OS 39.2 months vs. not reached, HR=3.65, P=0.05), retaining independent prognostic value in multivariate analysis (Table 2). These findings demonstrate the feasibility of optimizing the LSC17 score for selected patient subsets.

Predictive Value of the LSC17 Score for Determining Response to Therapy

Figure 3E:
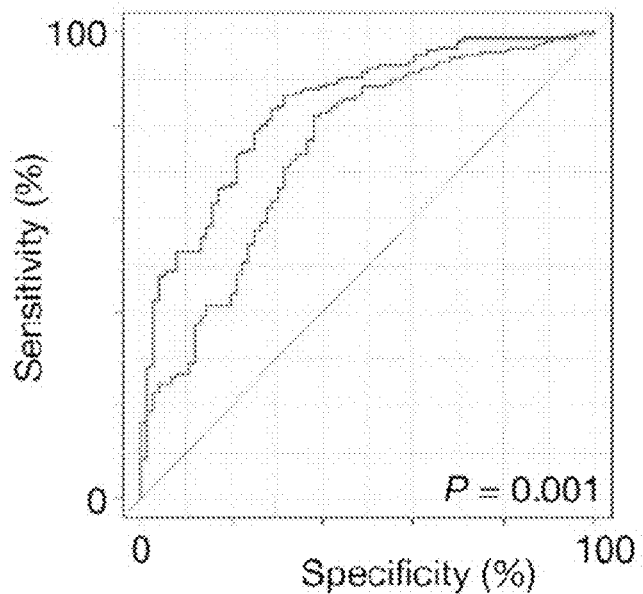
Figure 3F:
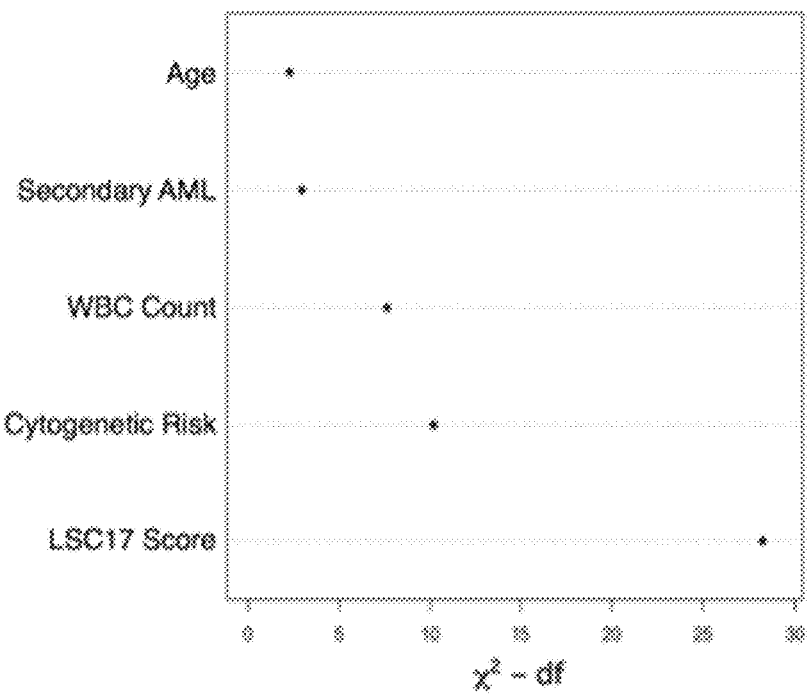
Figure 3G:
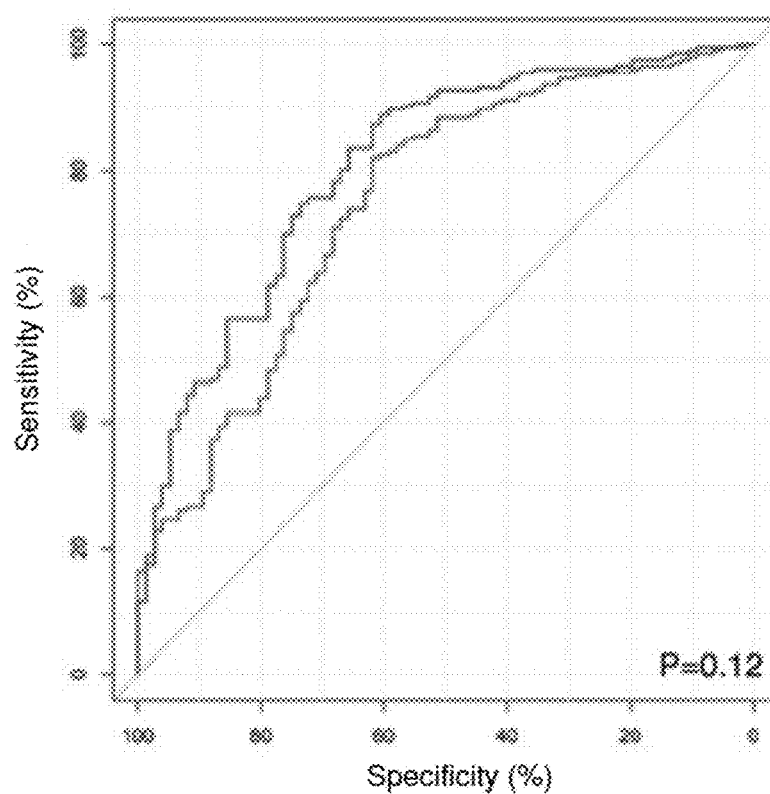

Having demonstrated a strong association between LSC17 score and survival outcomes, we tested the ability of the score to predict therapy resistance (defined as failure to achieve CR after initial induction)[9] for purposes of helping to determine appropriate course of therapy. In the PM cohort, LSC17 score as a single continuous variable was more predictive of therapy resistance than cytogenetic risk (AUROC=0.78 vs. 0.70) (data not shown). In multivariate logistic regression models that also considered age, WBC count, cytogenetic risk and de novo vs. secondary AML, inclusion of LSC17 score markedly improved predictive ability (FIG. 3E, Table S12, AUROC 0.73 vs. 0.82, P=0.001, increased sensitivity=3.38%, increased specificity=9.20%), and LSC17 score was the most predictive covariate as measured by the Chi-squared statistic (FIG. 3F). Multivariate models that included either cytogenetic risk or continuous LSC17 score had comparable predictive-ness for therapy resistance, with the latter trending towards improved prediction (FIG. 3G, AUROC 0.73 vs. 0.79, P=0.12, increased sensitivity=2.10%, increased specificity=5.71%). Similar results were obtained when therapy resistance was defined as failure to achieve initial CR or TTR<3 months (data not shown). As the LSC17 score was trained to associate with OS, we tested whether reweighting the 17 genes to predict treatment response directly would result in even stronger predictive ability, using a random 50:50 split of the PM cohort for training and testing. Indeed, the retrained response score had better predictive value as a single factor than the unadjusted LSC17 score (AUC=0.81). These results demonstrate that the LSC17 score improves the ability to predict therapy resistance in newly diagnosed AML patients.

We excluded patients who died within 1 month of treatment start in our analyses to avoid confoundment by cases of early death due to overwhelming disease and treatment related mortality. For purposes of this analysis, we defined therapy resistance as failure to achieve CR after initial induction. We and others have shown that patients who do not have a beneficial response to first induction have a poor outcome, regardless of post-induction therapy including allo-SCT (Brandwein et al, *Am J Hematol* 2008; Walter et al, *Biol Bone Marrow Transplant* 2015). Our local experience is that almost all patients who achieve a remission after 2 rounds of chemotherapy suffer a relapse without stem cell transplant. We therefore focused this analysis on achievement of CR after the initial induction. Our data indicate that patients with high LSC17 score are not cured with standard induction chemotherapy, even if they achieve CR, strongly supporting their enrollment into clinical trials to evaluate investigational induction therapies and post induction maintenance/continuation therapies.

Comparative Studies

Our earlier proof-of-principle study (Eppert et al, Nature Medicine 2011) established the biological concept that stemness properties of LSC assayed by xenotransplantation are linked to clinical outcomes. The validity of the approach we took in our earlier study was supported by the fact that even though only a small number of patient samples (n=16) was studied, and the LSC signature reported was in essence the unedited short list of genes that were more highly expressed in functionally validated LSC+ vs LSC− cell fractions, the signature was associated with survival outcomes in an independent cohort of CN-AML patients. However, our prior study was not conceived nor designed for clinical translation, and we anticipated that development of a robust clinical tool would require a study of much larger scope. Indeed, our initial LSC signature was not prognostic in more recently published AML cohorts, and could not be validated for all AML subtypes. The current study, carried out on a much larger scale (n=83 patient samples), represents the crucial next step, and is equally if not more important because it builds on our initial biologic observations to provide a novel tool for clinical translation. Regression analysis of a deep LSC-associated gene list against a large training cohort comprising AML patients of all risk groups enabled extraction of the essential stemness features that drive clinically important outcomes. The resulting LSC17 score robustly predicts survival in multiple independent AML cohorts, including the CN-AML subgroup, and across several GE measurement technologies including microarrays, RNA-sequencing, and NanoString. The LSC17 score not only highlights current unmet needs in the treatment of high-risk AML patients, but also provides a rapid and reliable tool to address these needs that is easily implemented on the NanoString platform and can bring about a change in clinical practice. The LSC17 score is the most powerful predictive and prognostic biomarker currently available for AML, and is the first stem cell-based biomarker developed in this way for any human cancer.

We assessed the strength of association of LSC17 scores and patient outcome relative to other published LSC GE signatures:
  1. Levine J H, Simonds E F, Bendall S C, et al. Data-Driven Phenotypic Dissection of AML Reveals Progenitor-like Cells that Correlate with Prognosis. Cell 2015:1-15.
     Summary of comparison: This study describes 2 signatures: 1 phenotypic and 1 mass cytometry derived. Levine signature scores were computed for 2 AML cohorts (GSE12417 CN-AML cohort 1, n=156; TCGA AML cohort, n=183). Multivariate CPH models were constructed to assess the prognostic value of the Levine signatures when common clinical factors such as patient Age, WBC, de novo vs. secondary AML, cytogenetic risk category, and finally the LSC17 scores were accounted for in the analysis. As a single explanatory variable, the Levine signatures were robustly associated with patient OS. However, upon inclusion of clinical factors, the Levine signatures became barely significant (p~0.05). When LSC17 scores were further added to the models, the Levine signatures became clearly non-significant, while LSC17 scores remained highly prognostic.
  2. Jung N, Dai B, Gentles A J, Majeti R, Feinberg A P. An LSC epigenetic signature is largely mutation independent and implicates the HOXA cluster in AML pathogenesis. Nat Comms 2015; 6:8489.
     Summary of comparison: This study reports a functionally derived GE signature identified from differentially methylated regions between LSC+ and LSC− samples. The analysis applied to the Levine signatures was applied here with similar results observed.
  3. Gentles A J, Plevritis S K, Majeti R, Alizadeh A A. Association of a leukemic stem cell gene expression signature with clinical outcomes in acute myeloid leukemia. JAMA 2010; 304(24):2706-15.
     Summary of comparison: This study reports a phenotypically defined GE signature. The analysis applied to the Levine signatures was applied here with similar results observed.

When tested in 2 independent cohorts (GSE12417 CN-AML cohort 1 and TCGA AML cohort), these signatures 2 and 3 above were significantly prognostic as single factors or when controlling for common clinical covariates, however these were no longer significantly associated with survival when adjusted for our LSC17 score in multivariate analysis, whereas the LSC17 score remains strongly prognostic (Tables R1 and R2)

Recently, a comprehensive genomic classification scheme was reported and was shown to be more accurate for patient risk stratification than the previously described ELN risk group definitions (Dohner, H. et al., Blood, 2010; Papaemmanuil, E. et al., *N. Engl. J. Med.*, 2016). When this new scheme as outlined by Dohner was applied to the TCGA AML cohort, inclusion of the LSC17 score in multivariate CPH models significantly improved the overall strength of association of the model with patient OS (Table N1, P<0.001, LRT), and the LSC17 score itself remained statistically significant. Three of the fourteen subgroups in the new genomic classification scheme are less well characterized ("driver mutations but not class-defining", "no detected driver mutations", and "meeting criteria for 2 or more subgroups"); patients in these groups had similar survival. The LSC17 score was able to discriminate between shorter and longer OS in the combined subset of patients falling into these 3 subgroups, and thus refines this state-of-the-art genomics classification scheme (FIG. 13, Table N2). As a result, we anticipate that our LSC17 signature will be useful to differentiate each of the fourteen subgroups previously identified by Dohner.

Optimization

We also assessed the optimality of LSC17 (within the context of the data that we had for analysis) by generating 837,106 unique signatures that we could have derived from our dataset, mostly from 89 genes that were differentially expressed between LSC+ vs. LSC− cell populations (that we had full data for). We found that LSC17 ranked within the top 2.25% in terms of strength of association with patient OS in the training dataset as estimated using the hazard ratio (HR) from univariate and multivariate CPH models. We defined an optimal signature to have 3 key characteristics: (1) a good signature should not be composed of too many genes to reduce the chance of statistical overfitting, (2) a good signature should have a high HR in the training dataset, and (3) a good signature should be derived with a minimal number of training cycles to minimize the chance of generating a signature with spurious associations with patient outcome. LSC17 was derived using one training cycle.

Additional Validation

Additionally, we have carried out an analysis of allo-SCT data and showed in 2 independent AML cohorts (PM and TCGA) that a high LSC17 score remains strongly associated with shorter survival regardless of whether patients underwent allo-SCT or not (FIG. 11C-F). These data demonstrate that patients with a high LSC17 score are not cured by conventional induction chemotherapy, and moreover are not adequately rescued by allo-SCT, which is the most intensive post-induction therapy currently available. Overall, these findings highlight the fact that better upfront therapies are needed for high-risk patients. Our study not only demonstrates this need, but also provides the necessary tool—a rapid NanoString-based LSC17 score—to identify high-risk patients (independently of other adverse risk factors) for enrollment into clinical trials evaluating investigational induction therapies. At the same time, low LSC17 score patients, who have a better chance of cure with standard therapy, can be spared unnecessary added toxicity, including the morbidity of allo-SCT in first CR, which does not appear to confer a significant survival benefit for these patients.

We also tested the ability of the LSC17 score to predict response to GO, a drug-antibody conjugate that has been shown to improve survival in de novo AML patients when added to standard induction chemotherapy (Castaigne, S. et al., Lancet, 2012; Hills, R. K. et al., Lancet Oncol., 2014). In a subset of patients from the ALFA-0701 trial with available GE data, patients with low but not high LSC17 scores benefited from addition of GO to standard chemotherapy, with longer OS, EFS and RFS (OS FIG. 14A,D, median not reached vs. 34.3 months, HR=0.60, P=0.11; EFS FIG. 14B,E, Table N3, median 35.4 vs. 11.7 months, HR=0.42, P=0.001; RFS FIG. 14C,F, Table N3, median not reached vs. 16.4 months, HR=0.53, P=0.03). These data support the use of the LSC17 score to facilitate more rational use of experimental treatments, such as GO, in patients most likely to benefit from novel treatments, while sparing high-risk patients who do not derive benefit any potential toxicities.

Relapse after achievement of remission is another major barrier to cure in AML. Ivey et al (*NEJM Jan.* 20, 2016) recently showed that persistence of NPM1-mutated transcripts during remission was independently prognostic for relapse and death in this molecular subtype of AML. However, minimal residual disease (MRD) analysis is carried out after the patient has received induction chemotherapy. Incorporation of the LSC17 score, which is applicable to all molecular and cytogenetic risk groups, into upfront treatment algorithms has the potential to impact and even reduce the incidence of MRD, by allowing stratification of newly diagnosed patients with high scores into clinical trials of investigational induction therapies that may better eradicate disease.

We also generated additional data showing AUROC values with sequential incorporation of baseline clinical data (age, WBC count, secondary vs. de novo AML), cytogenetic risk, molecular data (NPM1 and FLT3-ITD) and LSC17 score into the regression models (FIG. 12 and Table R3), for both the entire PM AML cohort as well as the CN-AML subset. Due to an insufficient number of cases with both cytogenetic and molecular data, these variables had to be included in separate models. Additionally, we have found that discretizing scores into deciles results in very similar predictive value compared to raw continuous scores, but with more precise estimates of model coefficients (Table R3). In both patient sets, the LSC17 score substantially increased predictive accuracy in each model, increasing sensitivity and specificity by more than 8% and 1%, respectively (P<0.01) and the AUROC to a range of 81.0-83.9. When molecular data was included in the models, LSC17 score and WBC count were the most predictive covariates as measured by the Wald Chi-squared statistic; however, in the absence of molecular data (which is often not available prior to therapy initiation), the LSC17 score was by far the most predictive covariate. Similar results were seen with the reweighted treatment response score, although there was insufficient molecular data in the testing half of the PM AML cohort for its inclusion in the model. The predictive value of the LSC3 score could not be assessed due to insufficient data-points in the CN-LMR subset. Overall, these data further strengthen the clinical value of the LSC17 score as a tool to predict therapy resistance in newly diagnosed AML patients.

Figure 11A:
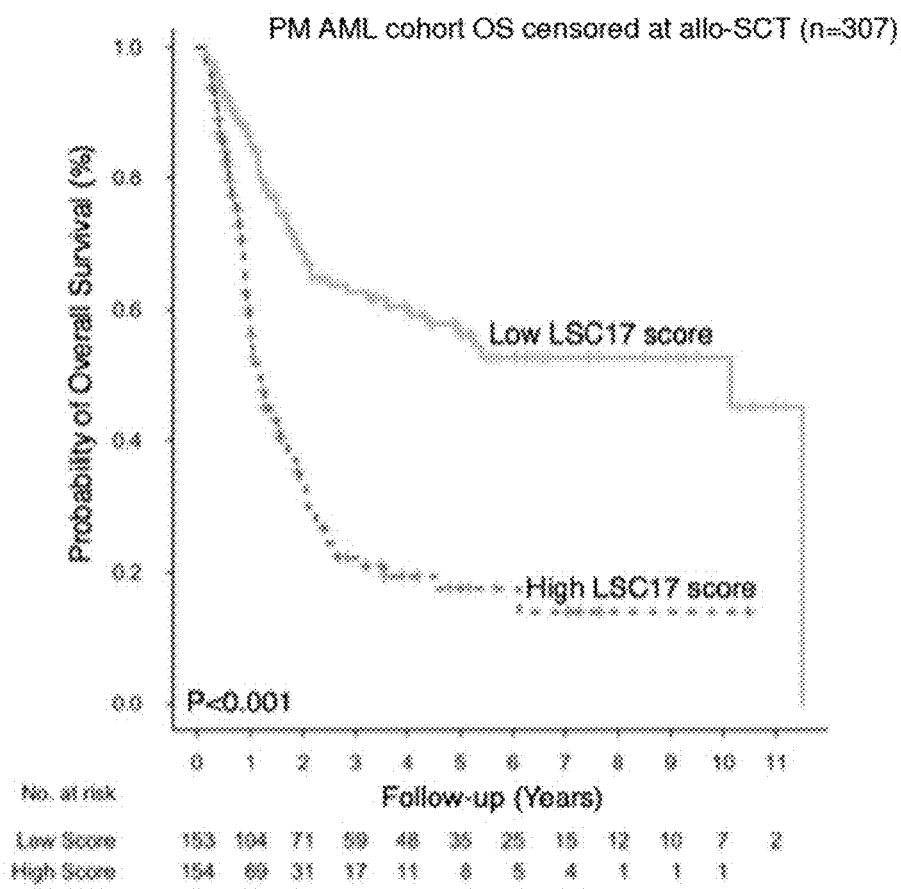
FIG. 11 shows a high LSC17 score is associated with shorter survival and early relapse regardless of allo-SCT.
Figure 11B:
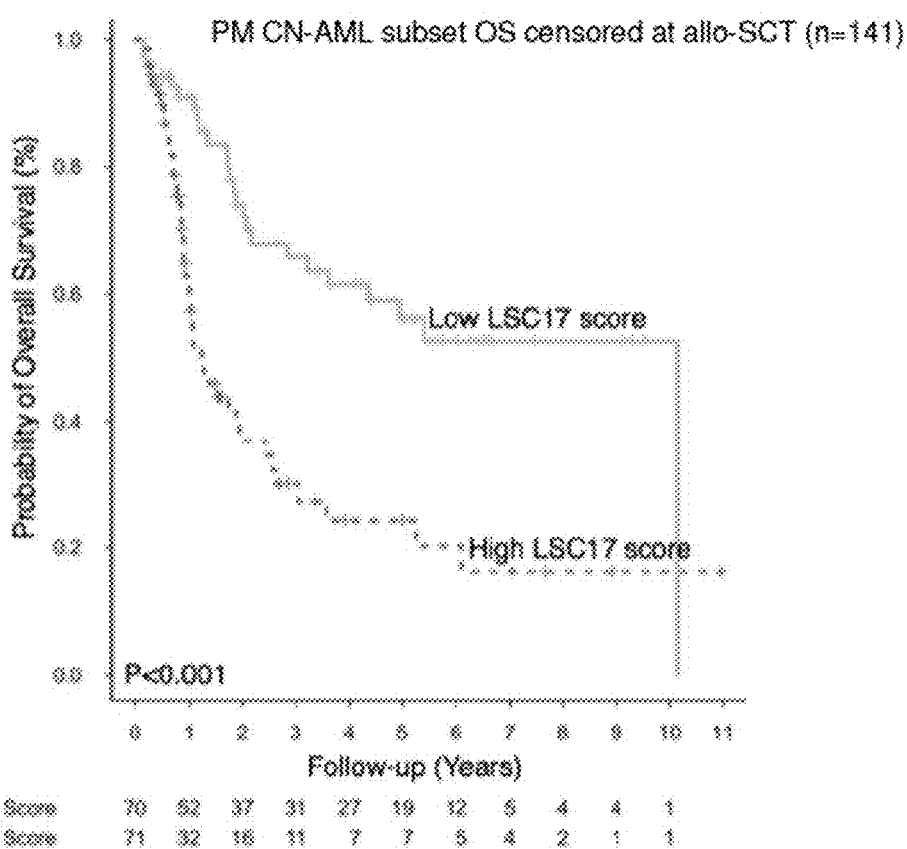
Figure 11C:
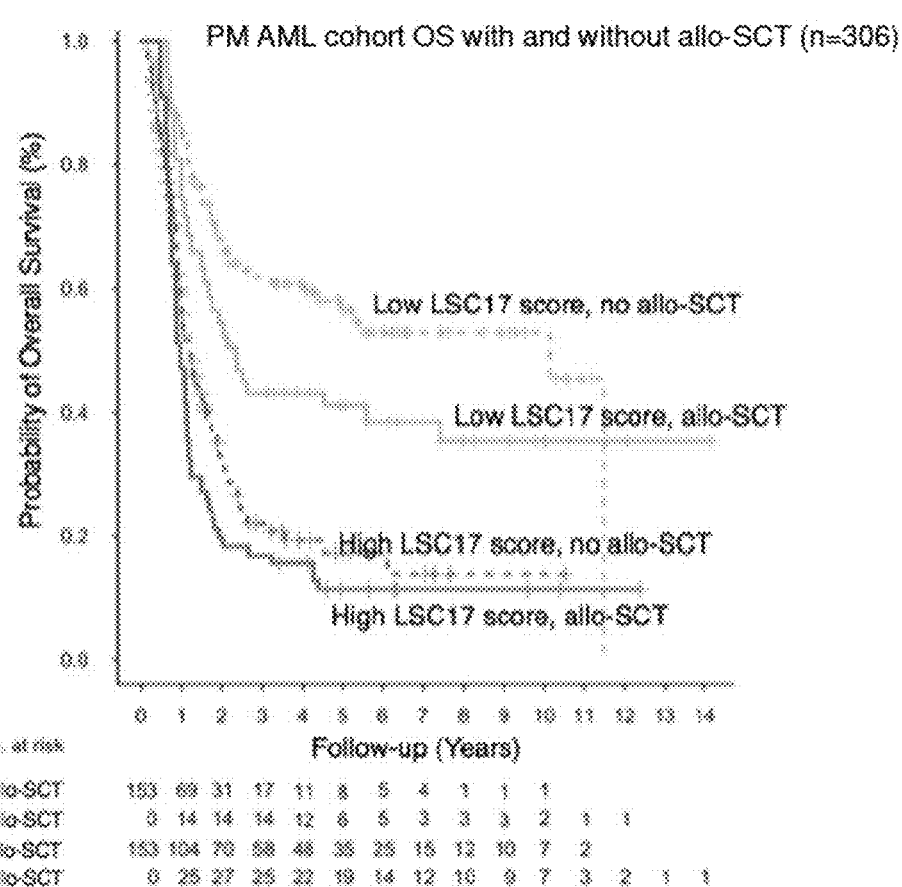

We presented dichotomized LSC17 scores based on the observation that the median LSC17 score divided intermediate cytogenetic risk patients in our training cohort (GSE6891) into subgroups with scores similar to those of adverse (above median) and favorable (below median) risk cases (FIG. 6). Raw LSC17 scores were also significantly associated with patient outcome in all time-to-event analyses (e.g. Table R4), however we opted to present dichotomized LSC scores in order to allow consistent visualization of time-to-event differences between high and low score patient subsets in univariate plots (e.g. FIG. 2). In contrast, in the manuscript we used raw continuous scores in all analyses of CR prediction, as they provided more information for AUROC estimation than dichotomized scores (data not shown). We have found that discretizing scores into deciles results in similar predictive value compared to raw continuous scores but provides more precise estimates of model coefficients (Table R3). We carried out further analyses to examine the potential effects of stem cell transplantation (SCT). First, a high LSC17 score remained strongly associated with shorter OS when censoring at the time of allo-SCT was applied to both the full PM AML cohort and the CN-AML subset (FIG. 11A-B; full cohort median OS 14.5 vs. 123.3 months; HR=3.02; P<0.001; CN-AML subset median OS 14.5 vs. 123.3 months; HR=2.85; P<0.001). The LSC17 score retained independent prognostic value in multivariate CPH models including common clinical factors (data not shown). Additionally, a high LSC17 score was significantly associated with shorter survival regardless of whether patients underwent allo-SCT in both the PM (OS, EFS, RFS) and TCGA (OS) AML cohorts as well as their respective CN-AML subsets (data not shown), with a statistically insignificant interaction term between LSC17 score and allo-SCT in CPH models.

Figure 11D:
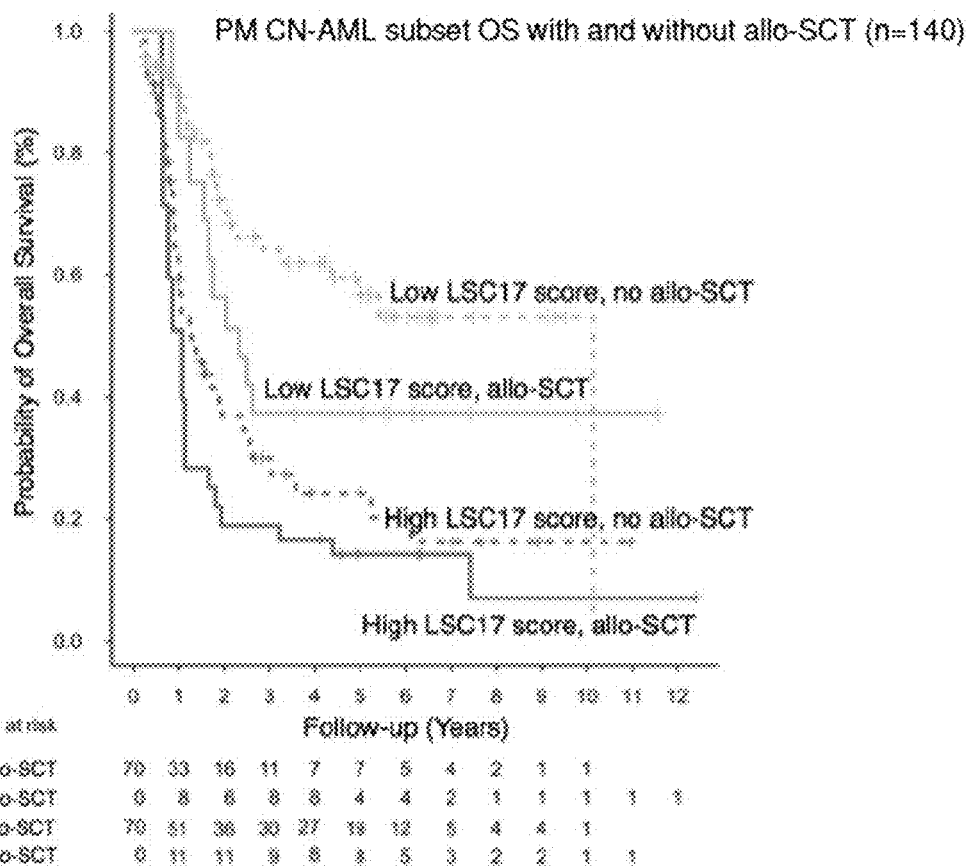
Figure 11E:
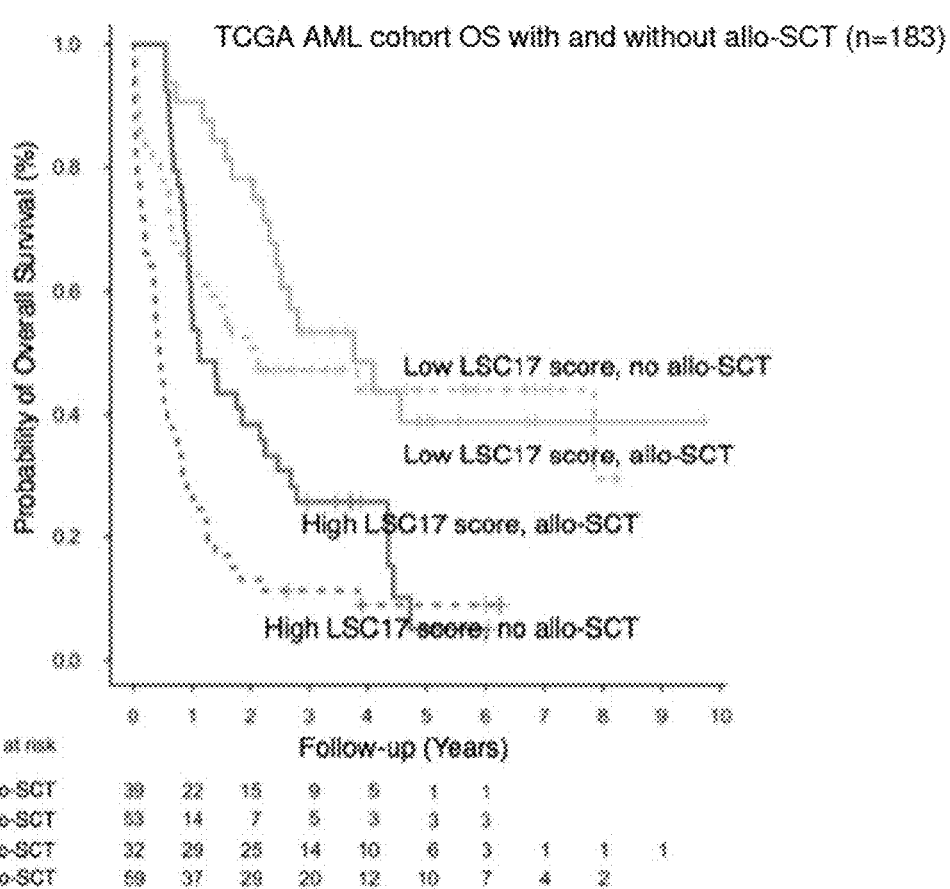
Figure 11F:
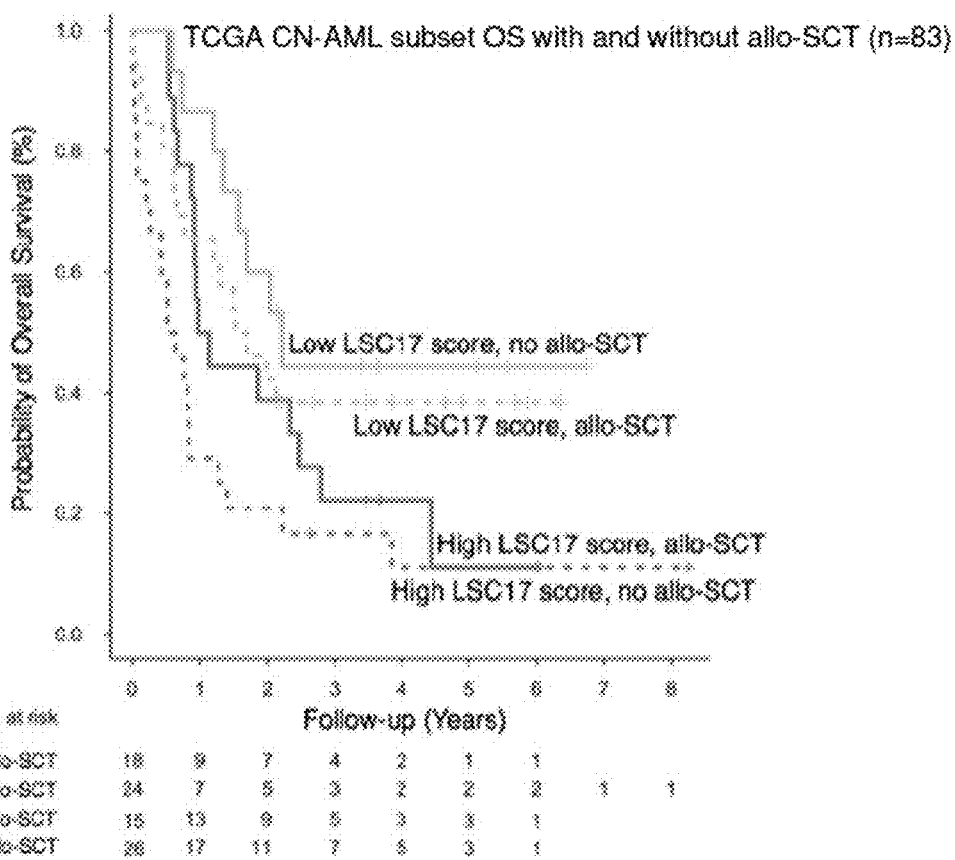

Inclusion of allo-SCT as a time-dependent covariate in the PM AML cohort (univariate Mantel-Byar analysis, FIG. 11C) did not demonstrate a significant impact of transplant on survival (low LSC17 score, P=0.06; high LSC17 score, P=0.20); a high LSC17 score was associated with shorter OS irrespective of whether or not patients underwent allo-SCT (allo-SCT: median OS 11.7 vs. 28.4 months for high and low LSC17 score respectively; HR=2.14; P=0.005; no allo-SCT: median OS 14.7 vs. 123.3 months; HR=2.99; P<0.001). The LSC17 score retained prognostic value when adjusted for common clinical factors in multivariate Andersen-Gill models (Table R5), with similar trends observed in the subset of CN-AML cases (FIG. 11D). These findings extend to the analysis of EFS and RFS, as well as to LSC3 scores applied to the small CN-LMR subset (NPM1mut, FLT3-ITD negative) (data not shown). We could not perform the same analyses on the TCGA AML cohort due to lack of available time-to-transplant data, but a similar pattern can be observed overall and in CN-AML cases with subset analysis of LSC17 score vs. allo-SCT (FIGS. 11E-F).

Figure 11G:
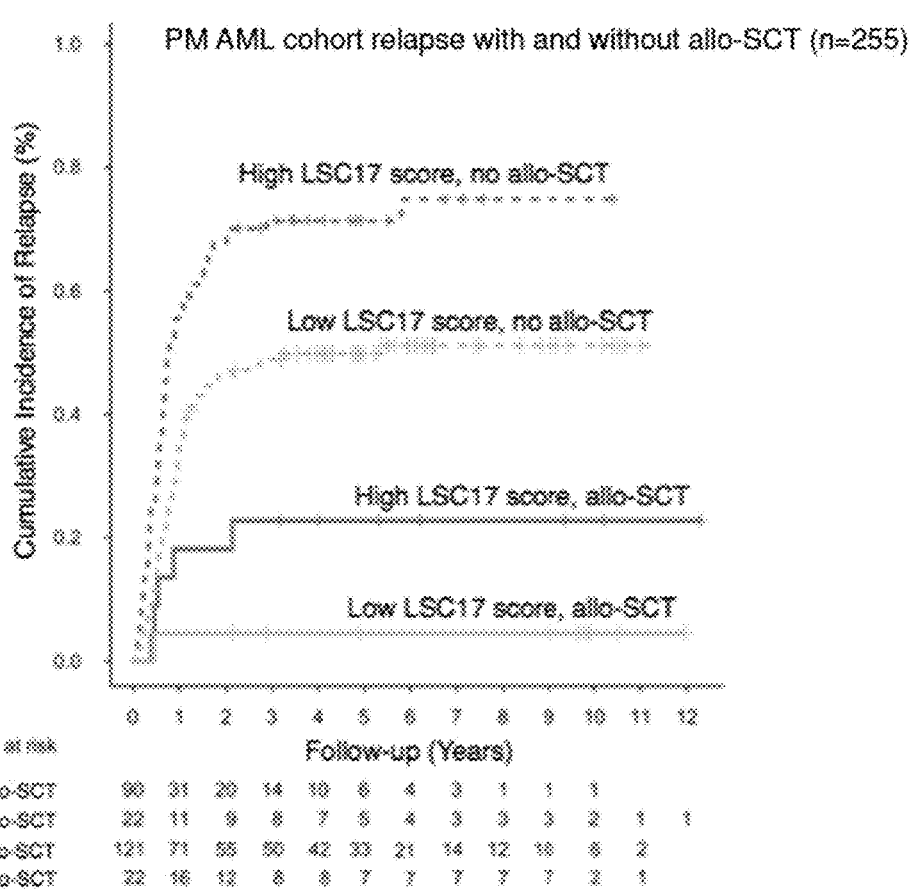
Figure 11H:
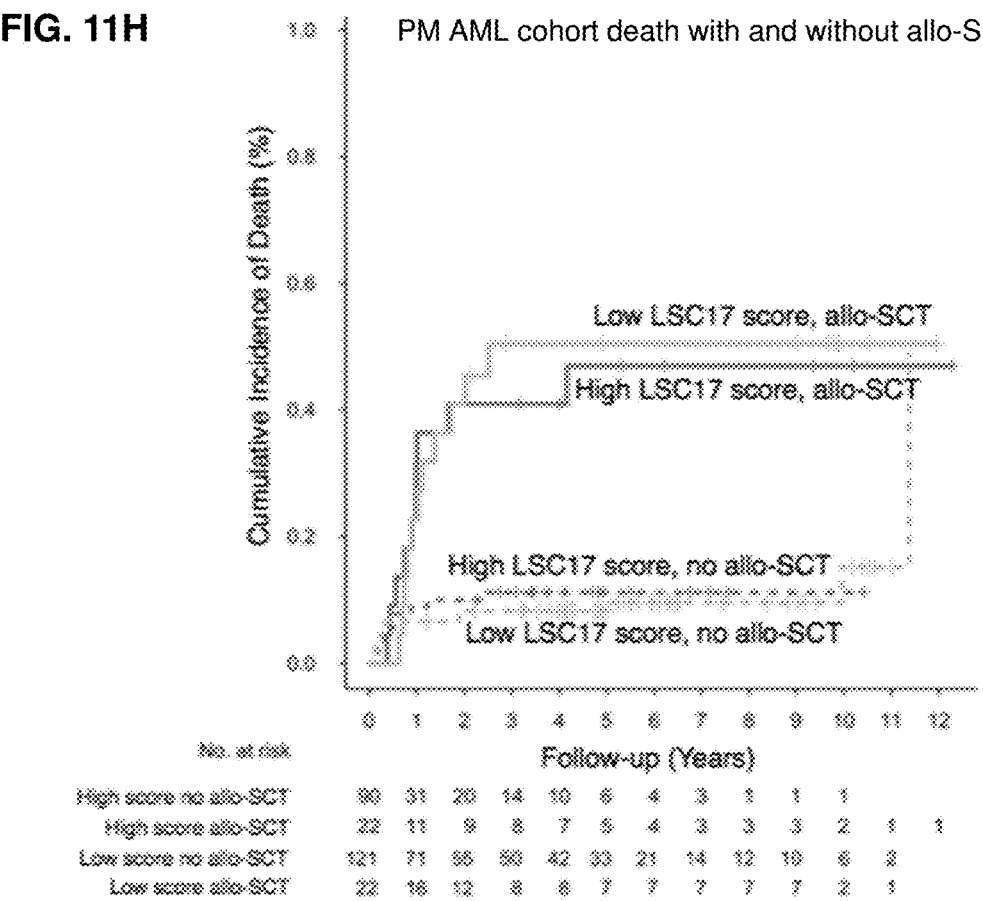
Figure 12A:
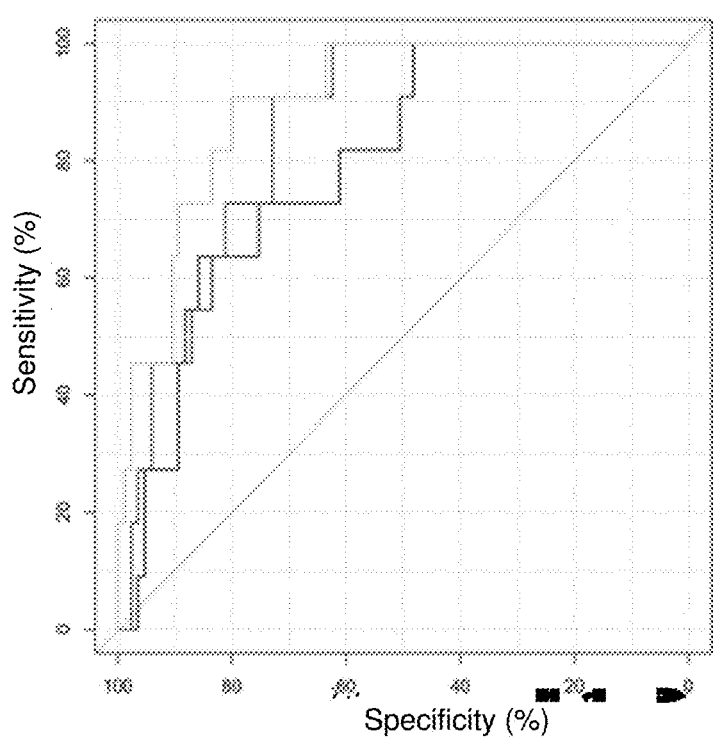
Figure 12B:
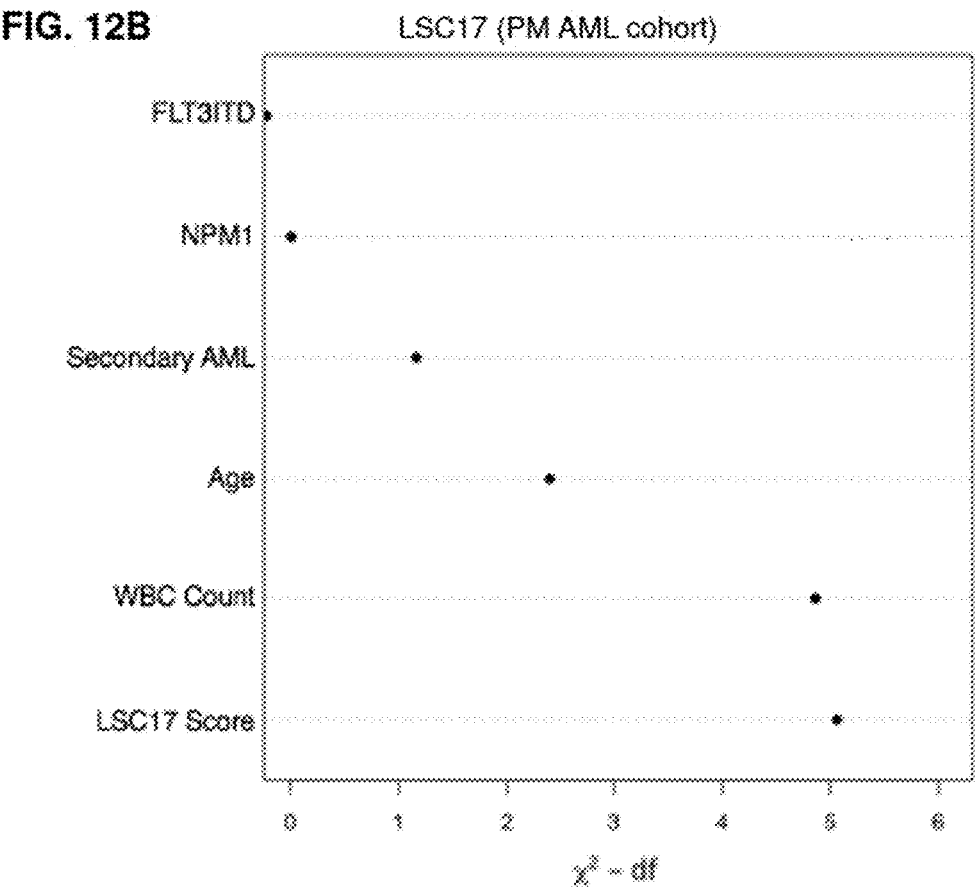
Figure 12C:
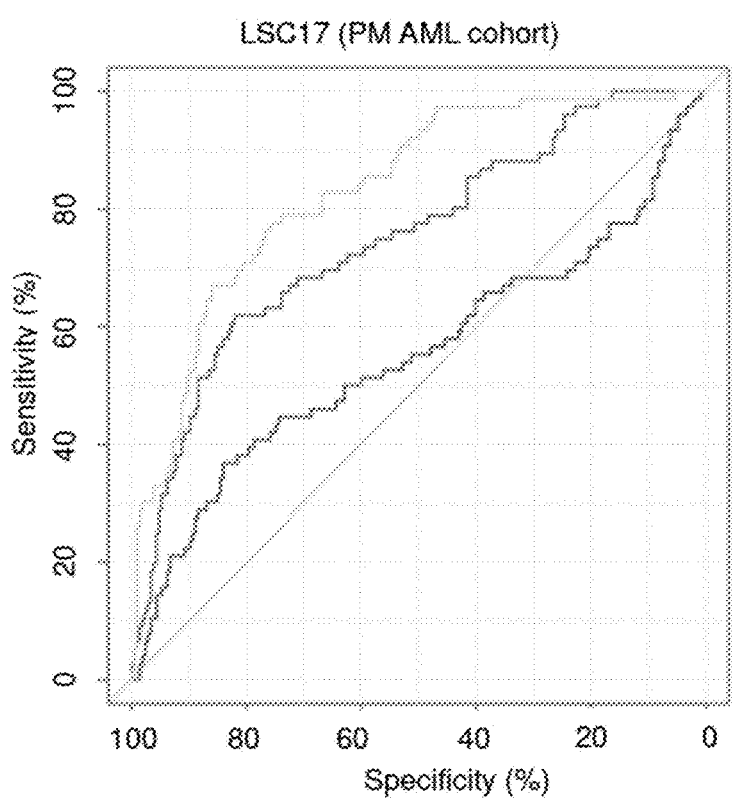
Figure 12D:
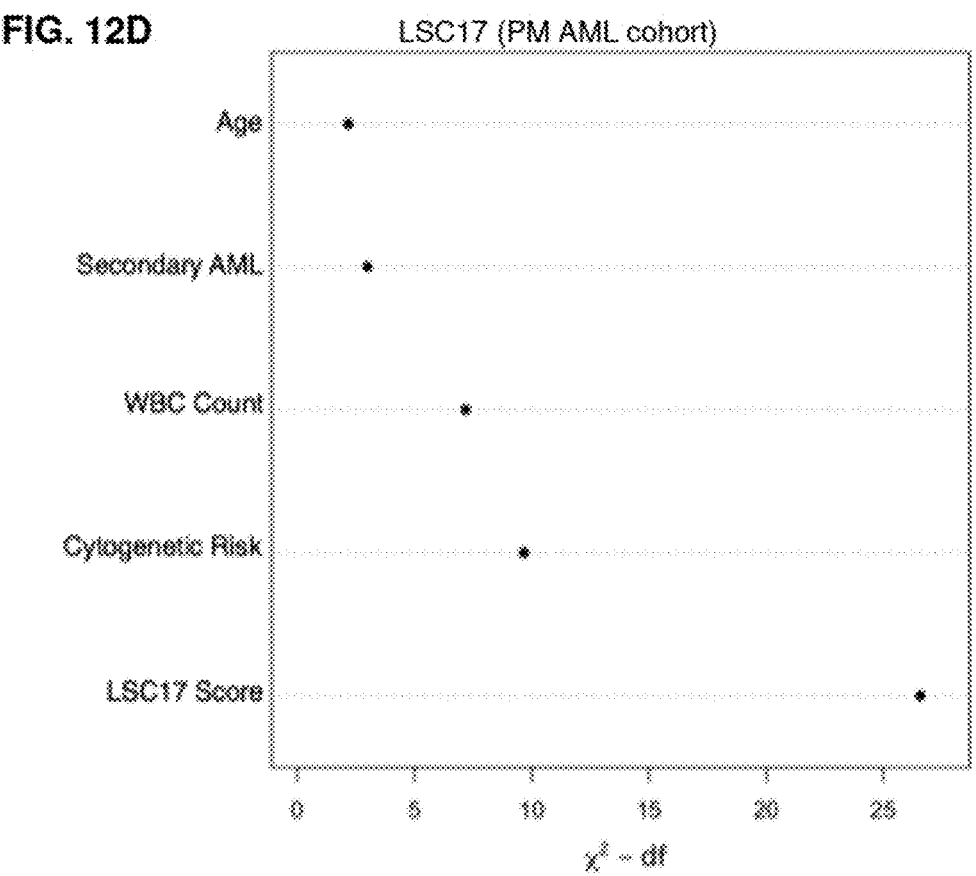
Figure 12E:
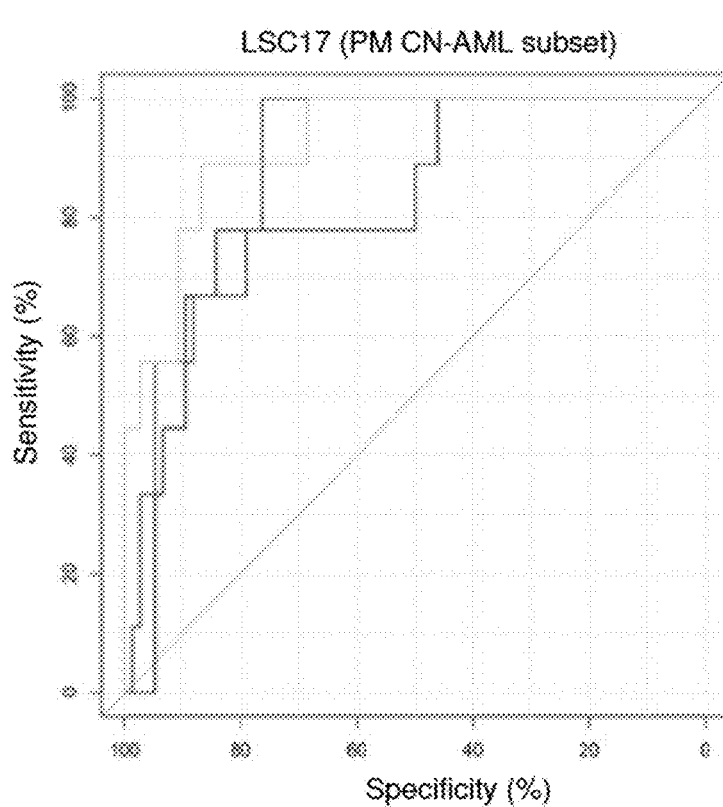
Figure 12F:
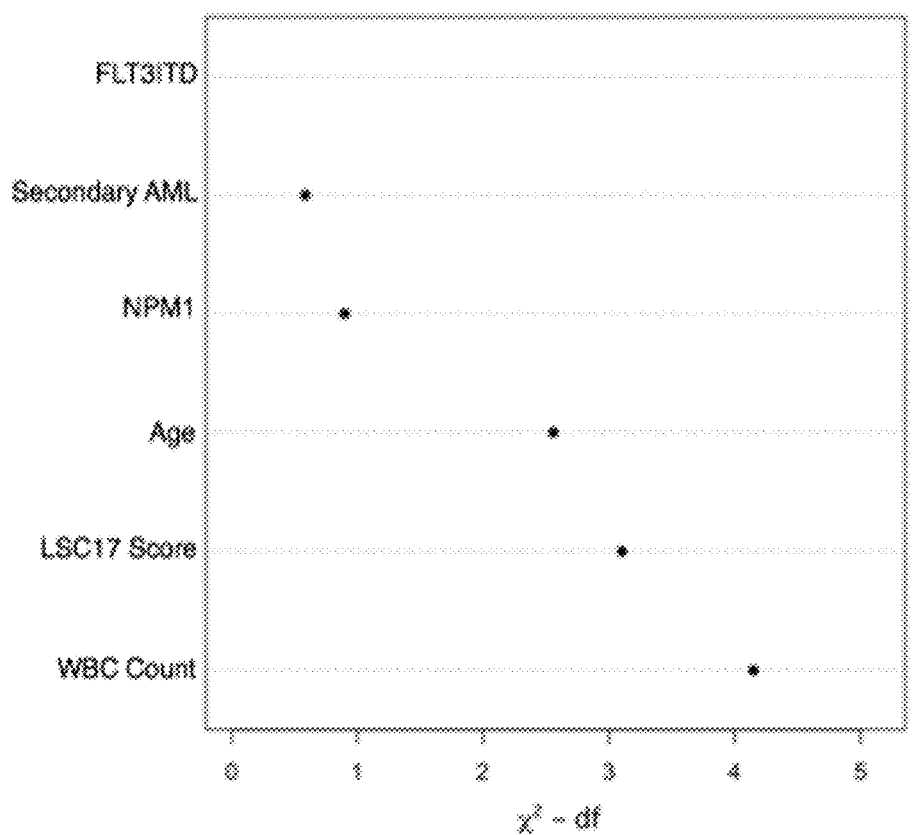
Figure 12F:
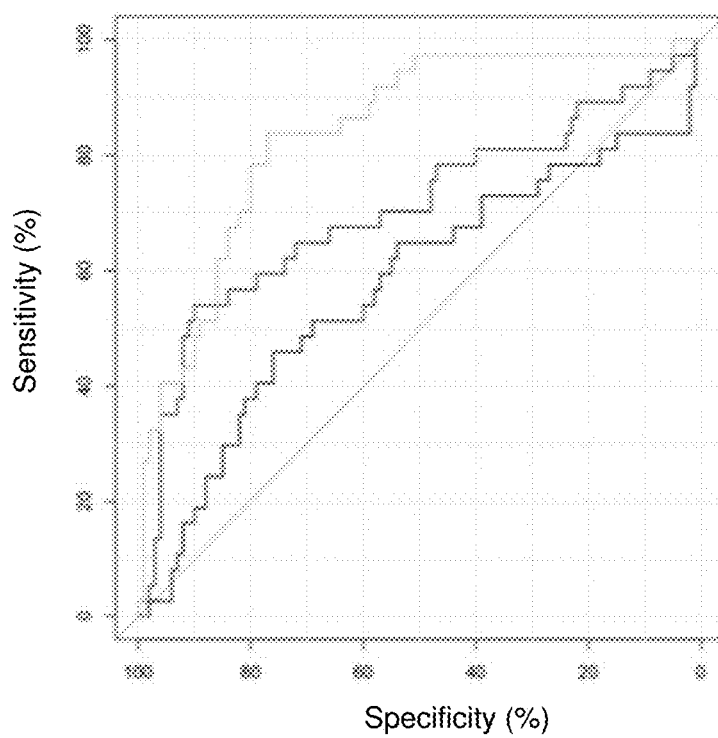
Figure 14A:
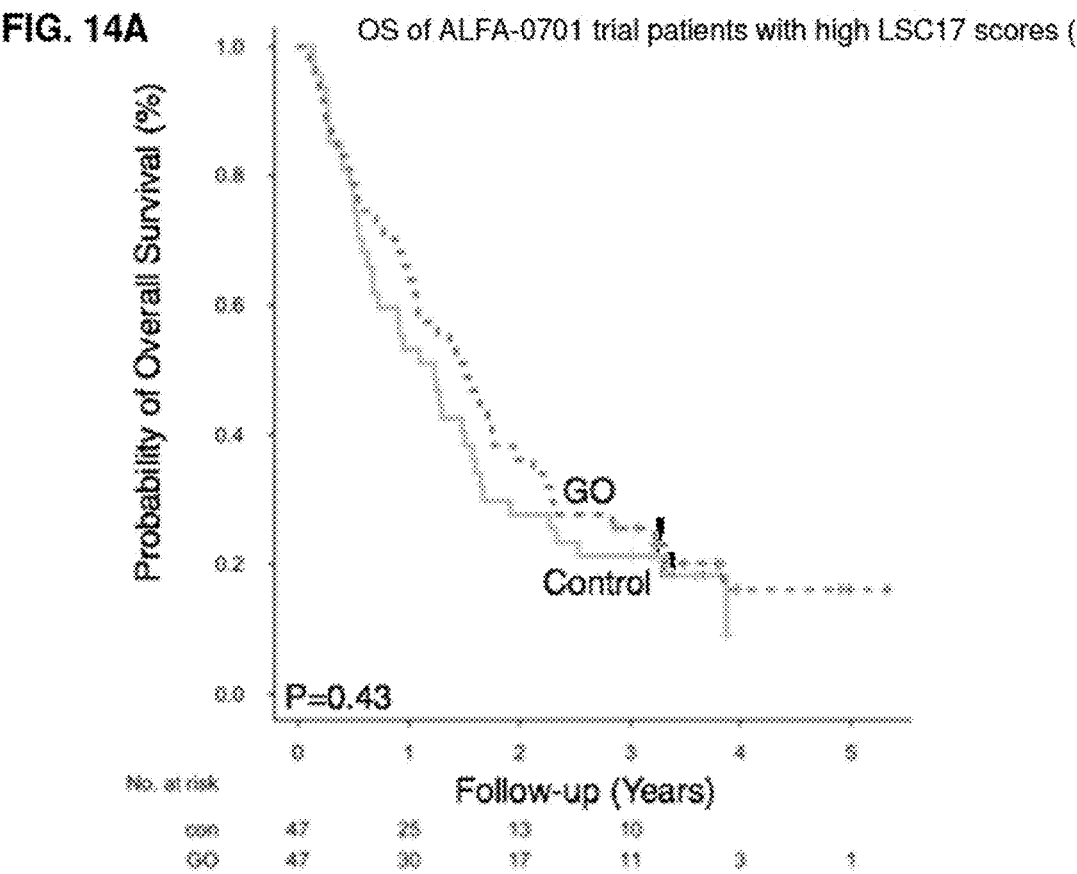
Figure 14B:
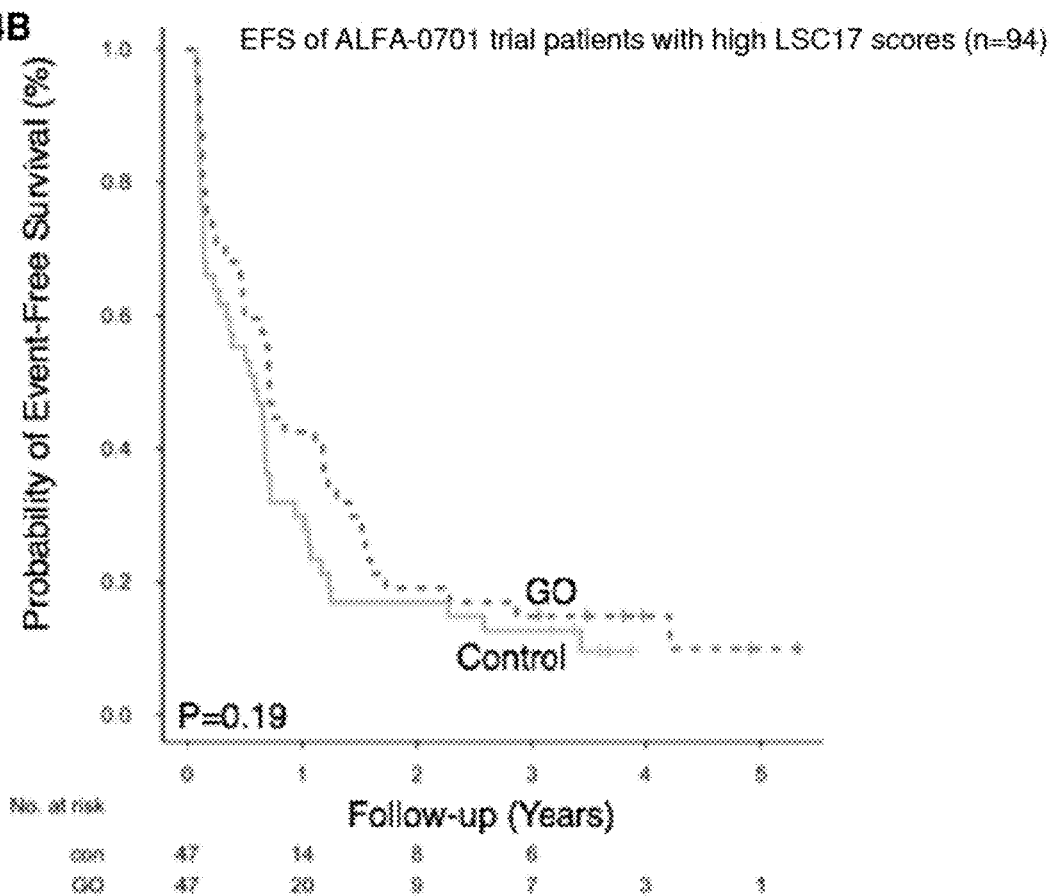
Figure 14C:
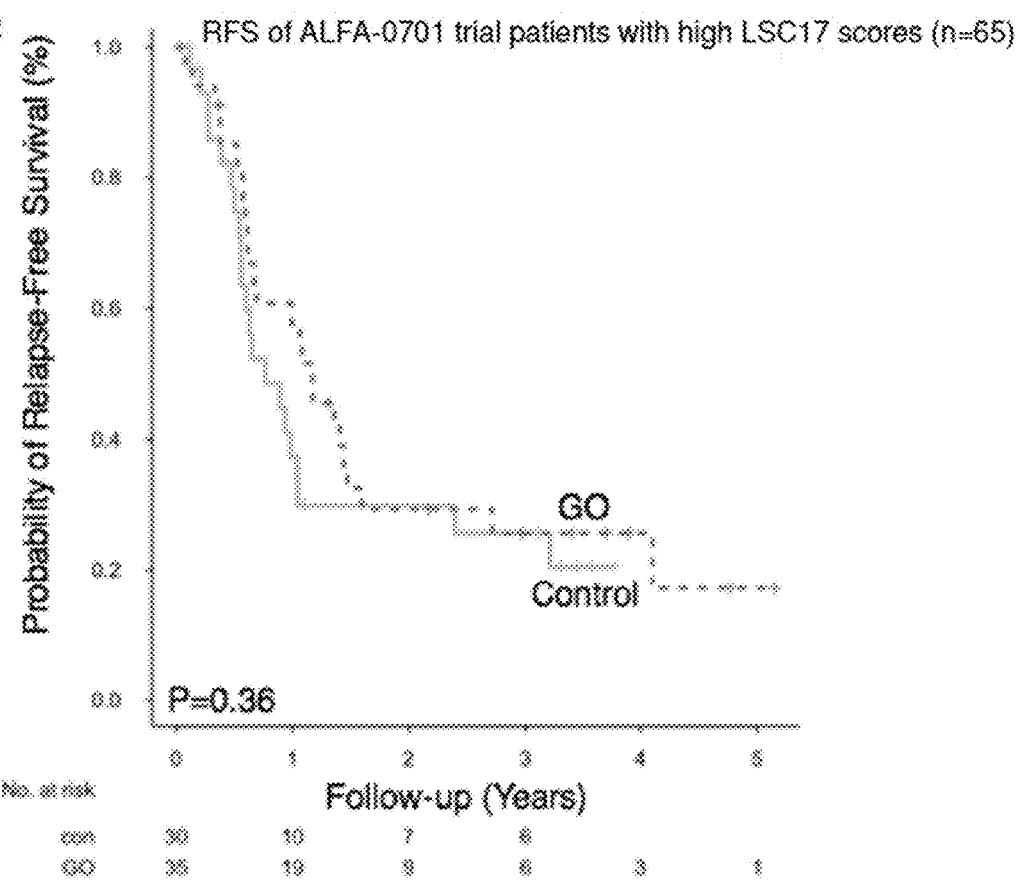
Figure 14D:
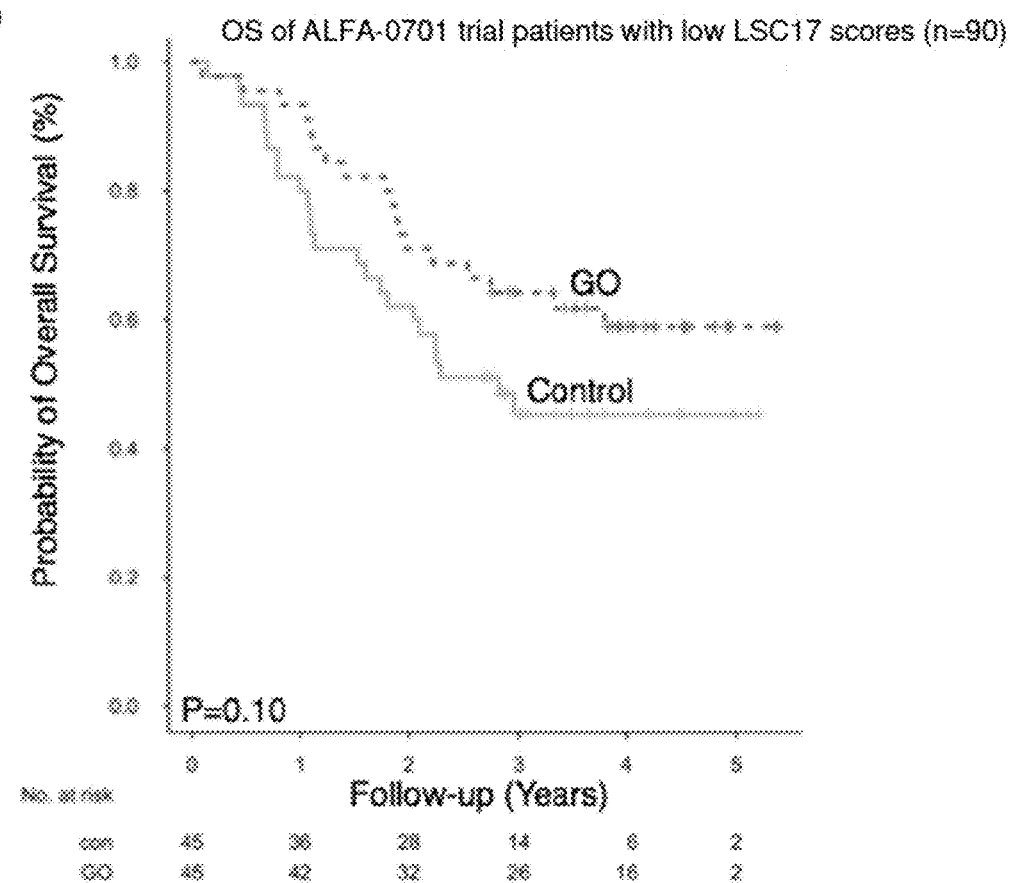
Figure 14E:
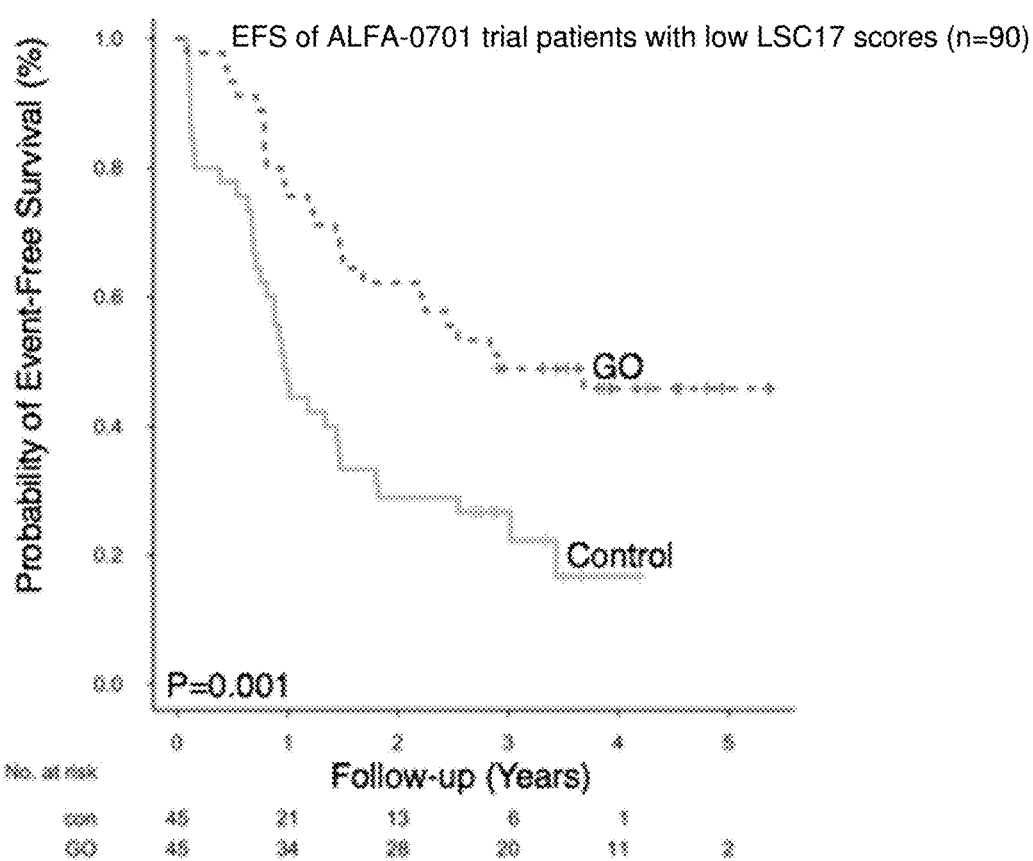
Figure 14F:
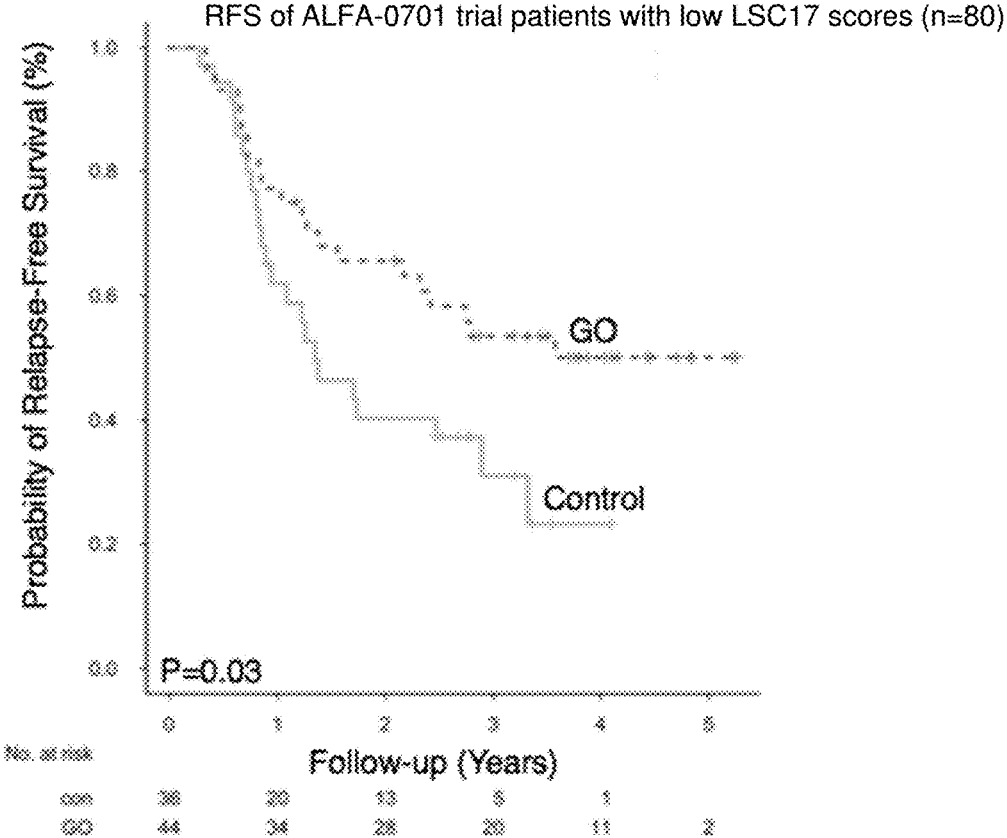
Figure 15A:
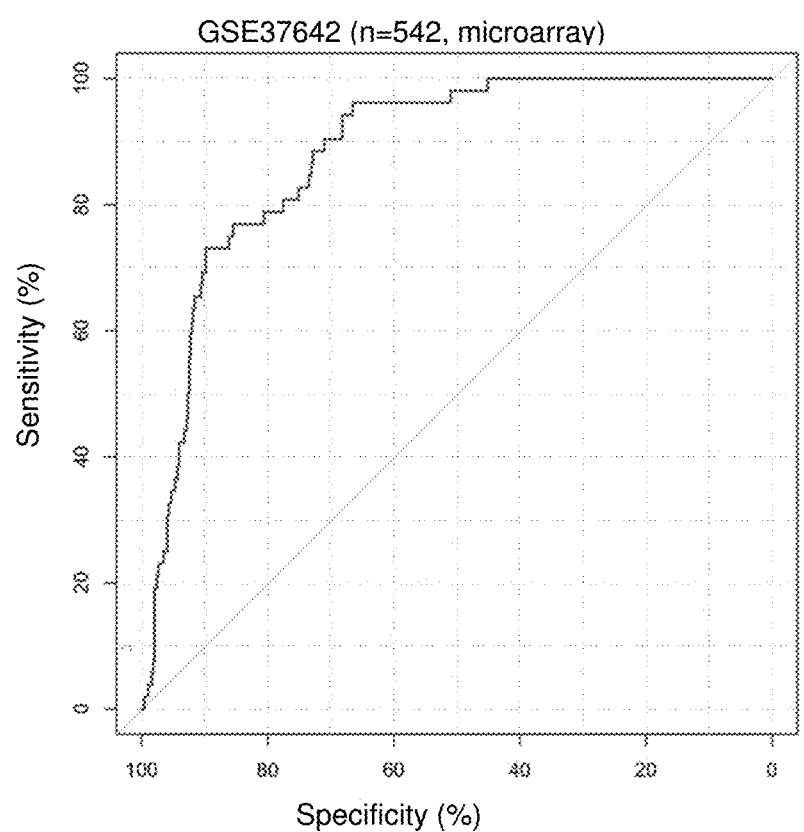
Figure 15B:
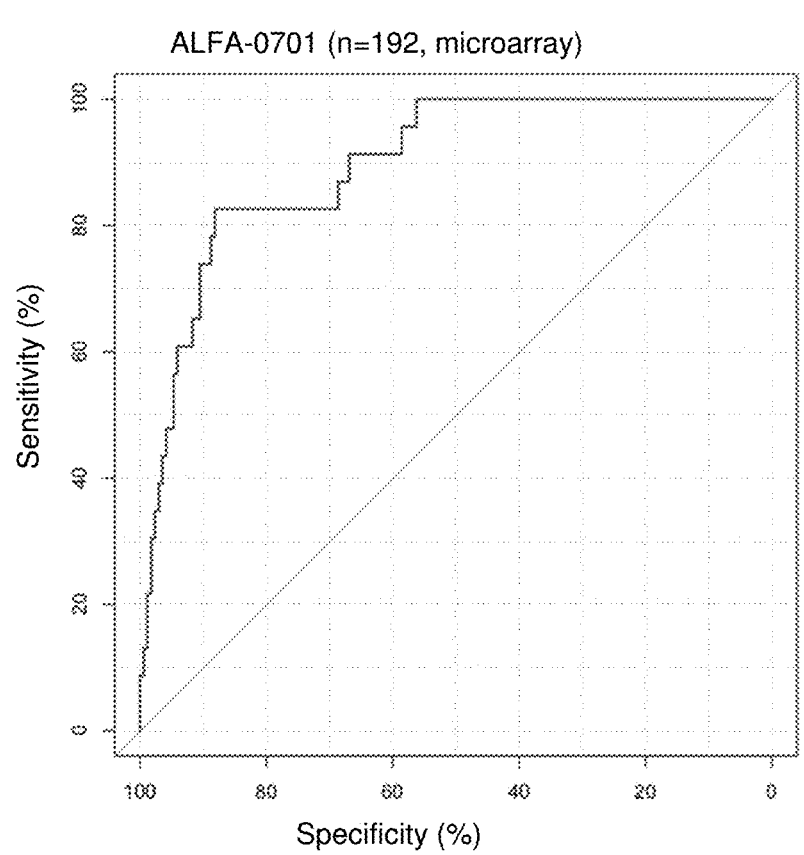
Figure 15C:
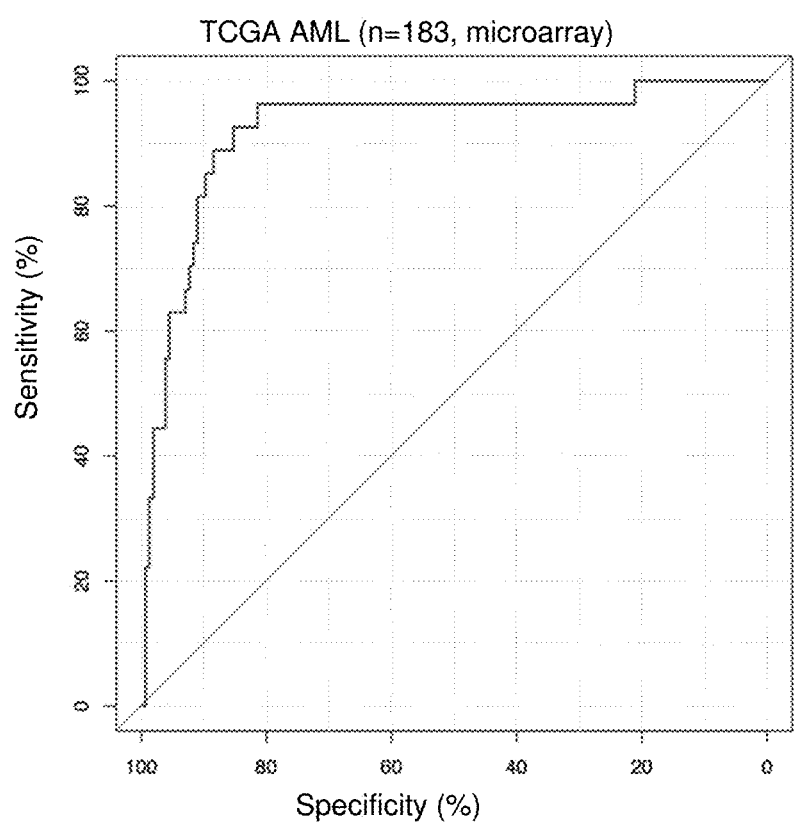
Figure 15D:
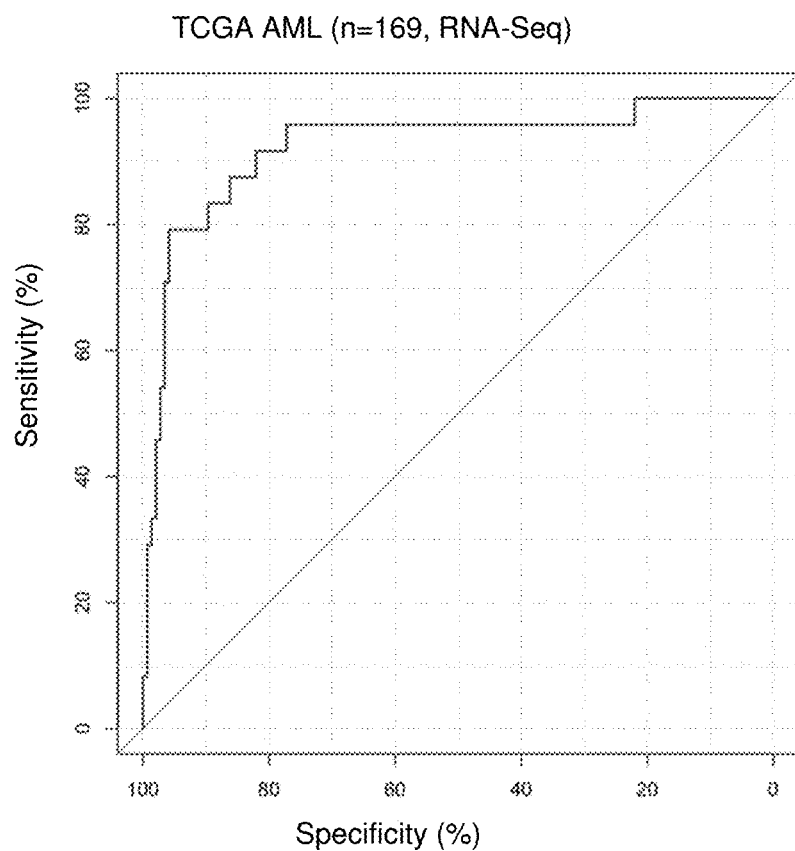
Figure 15E:
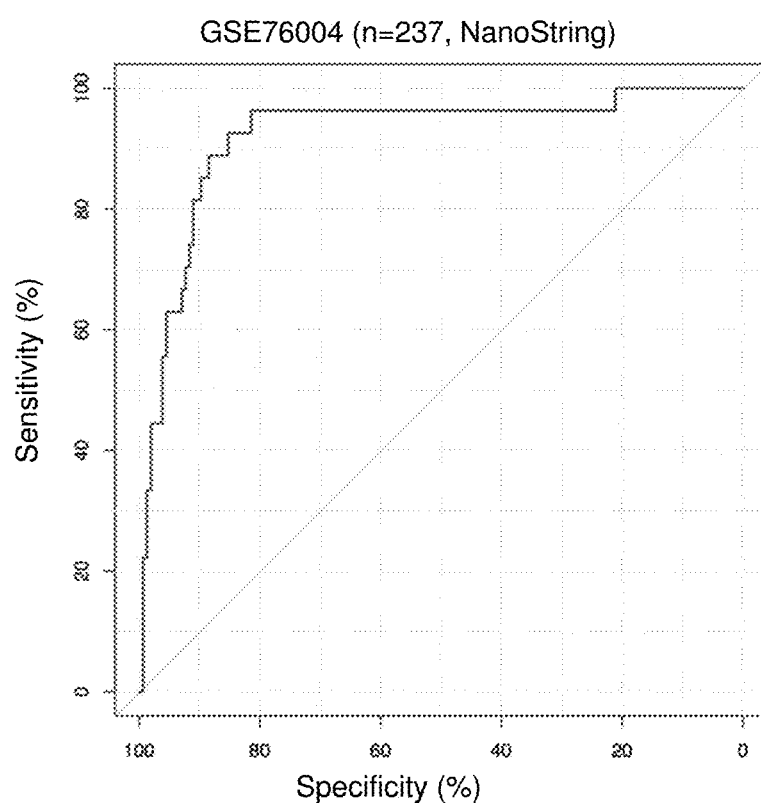
Figure 15F:
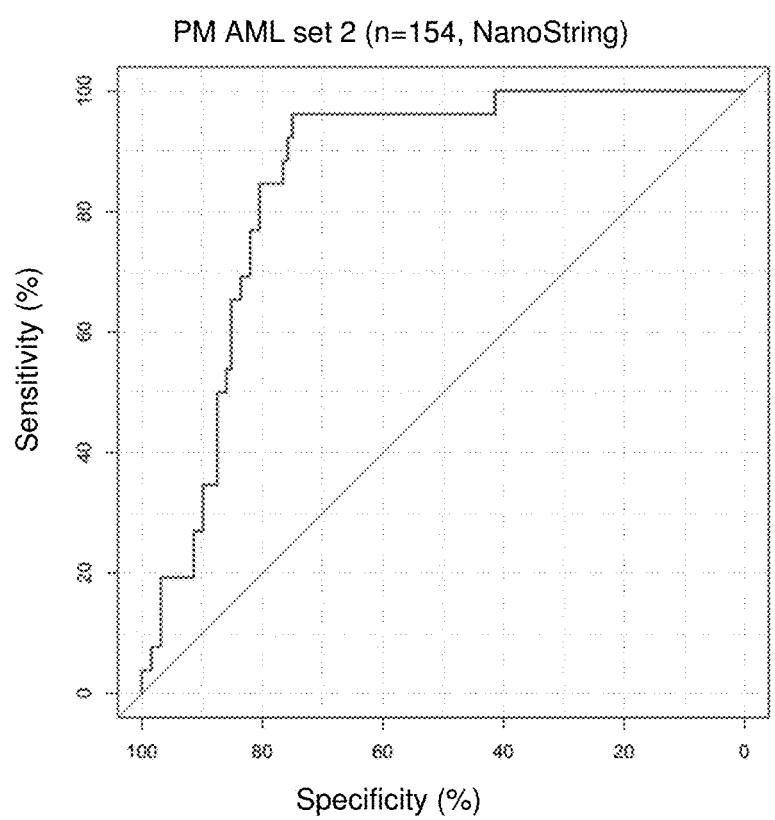

We also examined the cumulative incidence of the competing risks of relapse and death from time of first CR in patients who did or did not undergo allo-SCT in the PM AML cohort. A high vs. low LSC17 score was associated with earlier relapse in the subset of patients who did not undergo allo-SCT, in both univariate (FIG. 11G, sub-distribution HR [SHR]=1.92; Gray's test P<0.001; median TTR 9.31 vs. 65.2 months) and Fine-Gray multivariate (Table R6) analysis. allo-SCT reduced the risk of relapse, although small patient numbers precluded seeing a statistically significant difference between high and low score patients (SHR=5.26; P=0.09). However this was offset by a significantly greater risk of death in both high and low score groups compared to patients who did not undergo allo-SCT (FIG. 11H, P<0.001). Indeed, the risk of death following alto-SCT vs. relapse without allo-SCT was very similar in low score patients, suggesting that allo-SCT with its high mortality risk be considered only for high score patients who have more resistant disease.

Overall, these data provide additional evidence of the strong prognostic value of the LSC17 score, and further demonstrate the urgent need for new upfront approaches to treat AML, particularly for high score patients who do poorly following standard induction chemotherapy regardless of allo-SCT. Our LSC17 score provides a tool for identifying such patients for enrollment into clinical trials.

To determine whether other gene mutations were significantly associated with high or low LSC17 score, we examined genes mutations that occurred in at least 3 patients in the TCGA AML dataset as well as limited molecular data in a subset of the PM AML cohort (Table R7). In the TCGA AML cohort, only 6 mutations occurred in at least 3 patients and were also significantly associated with OS as single factors in univariate survival analysis: PML-RARA (n=15; HR=0.30; P=0.008), MYH11-CBFB (n=10; HR=0.33; P=0.03), TP53 (n=16; HR=3.61; P<0.001), RUNX1 (n=17; HR=1.79; P=0.03), DNMT3A (n=45; HR=1.58; P=0.02), and FLT3 in-frame mutations (n=4; HR=5.98; P<0.001). In a multivariate CPH model that included all 6 mutations as well as common clinical parameters (age, WBC count, cytogenetic risk group), only DNMT3A (barely) retained prognostic significance when the LSC17 score was included in the model, whereas the score remained a strong and significant independent prognostic factor (Table R8). Similar results were found for TCGA CN-AML cases (data not shown), and a small subset of the PM AML cohort for which limited gene mutational data was available (Table R8). These data demonstrate the utility of the LSC17 score as a risk stratification tool independent of mutational profiling, and will be added to a revised manuscript.

Table N4 contains the probe sequences designed for our NanoString-based LSC17 diagnostic assay (used in conjunction with the standard chemistry protocol available through Nanostring), which comprises of 17 LSC signature and 9 of the 12 noted reference genes. Table N4 probes can also be used in conjunction with "Elements" chemistry protocol available from Nanostring, which would be used in conjunction with all 12 of the noted reference genes. We found this probeset of particular use, and found, for example a prior codeset design did not yield similarly effective results on the NanoString platform.

Our study identified a 17-gene signature score (LSC17) that was able to discriminate between better and worse outcome patients from 4 independent AML datasets comprising 716 cases treated on different protocols, and improves prediction of resistance to induction therapy. The robustness of the LSC17 score is grounded in its derivation from a wide diversity of primary patient samples and the large number of functionally-defined LSC-containing populations from which DE genes were identified, as well as regression analysis applied to a large training cohort[25] in order to reduce statistical over-fitting. Moreover, by re-weighting the 17 signature genes, we were able to generate a 3-gene score (LSC3) optimized for survival association in CN-LMR patients. The prognostic value of both the LSC17 and LSC3 scores remained highly significant in multivariate analyses, independent of commonly used prognostic factors including cytogenetic risk, and was retained across multiple GE quantification technologies including those based on microarray, RNA-Seq, and the clinically serviceable NanoString platform.

On the NanoString platform, rapid simultaneous single-assay determination of the LSC17, LSC3, and therapy response scores is possible with the shortest turnaround time from patient material collection to score generation between 24 and 48 hours. This estimate is based on the minimal sample preparation time for analysis by NanoString technology and data processing requirements. Actual score generation times will vary depending on center-specific practice, and will depend on how frequently the assay is run (batched). This turn-around time is a significant improvement over usual wait times for cytogenetic and molecular results, and will enable incorporation of score results into early treatment decisions.

Our ability to capture in the LSC17 score a myeloid leukemia sternness program highly associated with patient outcome provides strong evidence of the clinical relevance of the AML xenotransplantation assay, which has become the gold standard for novel drug development[24;37-38]. Indeed, further analysis of the entire set of 104 DE genes and their protein-protein interactors, encompassing a core transcriptional program of LSCs, may identify regulators of sternness properties in AML, as well as putative therapeutic targets. This idea is supported by recent evidence that CDK6, one of the LSC17 genes, governs stem cell specific aspects of quiescence control in normal human HSCs[21]. Indeed, low levels of CDK6 are associated with dormancy in HSCs and the negative regression coefficient of CDK6 in the LSC17 score is consistent with a link between lower CDK6 levels, a higher score, dormancy, therapy resistance, and poorer outcome. Conversely, higher expression of genes with a positive regression coefficient in the LSC17 score would be predicted to confer increased stemness properties to LSCs. The functional relevance of the DE LSC genes and their associated pathways derives from the use of functionally-rather than phenotypically-defined cell populations in our approach[18,34,40]; surface markers are often aberrantly expressed in AML and not directly related to functional properties. We previously used a similar approach to report a prognostic 42-gene LSC signature derived from 16 AML patient samples[18]. However, a much shorter list of DE genes was generated in that study, and signature risk scores were not significantly associated with survival when tested against additional datasets including the TCGA AML cohort[27], suggesting that the number and/or diversity of patient samples used to generate the 42-gene signature was not sufficient to capture the critical transcriptional features of LSC+ populations that relate to patient outcome in the broad spectrum of AML patients.

All patients in our training and testing cohorts received induction chemotherapy typically involving standard or high-dose cytarabine plus an anthracycline. The association between a high LSC17 score and failure to achieve initial CR and shorter RFS and OS likely reflects biologic properties of LSCs in those patients that confer increased resistance to conventional chemotherapy. Such patients, who are not cured by standard therapy and who can now be identified by a high LSC17 score soon after diagnosis, could be candidates for evaluation of investigational induction therapies. The LSC17 score will also be of help to clinicians working in AML centers where all patients are already enrolled in trials to evaluate the efficacy of investigational vs. standard regimens, based on the rationale that the current ability to identify patients who could be cured with standard induction therapy is only fair[9]. With the availability of a robust prognostic test such as the LSC17 score, recommendation of more intensified investigational therapies can be directed to high-risk patients predicted to have resistant disease and who may derive benefit from added therapy early in the disease course. Conversely, low-score patients who have a better chance of cure with standard therapy could be spared unnecessary added toxicity. Finally, the LSC3 score identifies a subset of CN-LMR patients with shorter survival, allowing evaluation of the possible benefits of maintenance therapy or early transplantation in first CR. Overall, the LSC17 and LSC3 scores, implemented on the NanoString platform, will enable rapid identification of high-risk patients for enrolment into clinical trials to evaluate novel approaches to induction and post-induction therapy in an effort to prevent relapse and increase cure rates.

Rapid Identification of CN-LMR AML Cases

AML is an acute condition that progresses quickly and therefore patients will benefit from earlier risk level determination so that the most appropriate treatment strategy can be decided earlier. Currently, most AML patients receive standard induction chemotherapy upfront at diagnosis regardless of risk level because risk stratification has depended on cytogenetic and molecular tests that typically take weeks to return results. A small subset of CN-LMR patients are considered to have favourable outcomes, but ~35% relapse within 2 years following conventional therapy. A high LSC3 score identifies CN-LMR patients who have poor outcomes following standard induction therapy, and who might benefit from novel frontline therapy. Currently however, the LSC3 score can only be employed in the post-remission setting, as CN-LMR patients are only identified following cytogenetic and molecular testing. Earlier identification of high-risk CN-LMR patients will facilitate clinical trials of novel frontline therapy targeted to this patient subset. Here we derived a new 13-gene sub-score (LSC13) utilizing the LSC17 signature genes by applying sparse binomial regression to a training cohort to identify CN-LMR patients using microarray expression data of the 17 LSC17 genes (GSE6891, n=48 [9%] CN-LMR of 495 patients). The resulting LSC13 score can accurately identify CN-LMR patients in five large validation cohorts spanning n=1308 cytogenetically and molecularly diverse AML patients (FIG. 15; microarray datasets: GSE37642, n=542, AUROC=0.88; TCGA AML, n=183, AUROC=0.92; ALFA-0701, n=192, AUROC=0.89; RNA-Seq dataset: TCGA AML, n=169, AUROC=0.92; NanoString datasets: GSE76004, n=237, AUROC=0.96; PM AML, n=154), providing direct support that the LSC13 score, which can be calculated using the LSC17 assay at the same time as the LSC17 and LSC3 scores, is a quick (24h to 48h) alternative to waiting for traditional genetic test results for CN-LMR patient identification. This new feature enhances the clinical utility of the LSC17 assay and will enable clinicians to simultaneously identify and risk stratify CN-LMR patients upfront so that more intensive or alternative therapies can be assigned earlier in the disease course for those predicted to be at higher risk.

We reasonably anticipate the ability use of the LSC17 genes, and subcombinations thereof, including to identify patients who are likely to benefit from new and currently untested AML specific treatments, particularly in view of our analysis and modeling represented by Table S13. This is particularly true because of the unique nature of these 17 genes—uniquely tested for their ability to initiate and propagate leukemia in xenotransplanted mice. This application of our assay is supported by the totality of all of our data, and the application of this signature to known AML risk stratification systems (and the fact that our LSC17 genes refines and enhances the accuracy of current stratification systems), and is further supported by our showing that the LSC17 score can identify high score patients who have significantly poorer survival relative to those with low LSC17 scores when treated with standard induction chemotherapy.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCES

1. Ferrara F, Schiffer C A. Acute myeloid leukaemia in adults. Lancet 2013; 381:484-495.
2. Alibhai S M, Leach M, Minden M D, Brandwein J. Outcomes and quality of care in acute myeloid leukemia over 40 years. Cancer 2009; 115:2903-2911.
3. Grimwade D, Hills R K, Moorman A V et al. Refinement of cytogenetic classification in acute myeloid leukemia: determination of prognostic significance of rare recurring chromosomal abnormalities among 5876 younger adult patients treated in the United Kingdom Medical Research Council trials. Blood 2010; 116:354-365.
4. Dohner H, Estey E H, Amadori S et al. Diagnosis and management of acute myeloid leukemia in adults: recommendations from an international expert panel, on behalf of the European LeukemiaNet. Blood 2010; 115:453-474.
5. National Comprehensive Cancer Network Guidelines: Acute myeloid leukemia, v.I.2015 (Dec. 3, 2014), NCCN, Fort Washington, P A. (Accessed Feb. 2, 2016, at http://www.nccn.org/professionals/physician_gls/f_guidelines.asp#am1).
6. Rollig C, Bornhauser M, Thiede C et al. Long-term prognosis of acute myeloid leukemia according to the new genetic risk classification of the European LeukemiaNet recommendations: evaluation of the proposed reporting system. J Clin Oncol 2011; 29:2758-2765.
7. Brandwein J M, Gupta V, Schuh A C et al. Predictors of response to reinduction chemotherapy for patients with acute myeloid leukemia who do not achieve complete remission with frontline induction chemotherapy. Am J Hematol 2008; 83:54-58.
8. Walter R B, Sandmaier B M, Storer B E et al. Number of courses of induction therapy independently predicts outcome after allogeneic transplantation for acute myeloid leukemia in first morphological remission. Biol Blood Marrow Transplant 2015; 21:373-378.
9. Walter R B, Othus M, Burnett A K et al. Resistance prediction in AML: analysis of 4601 patients from MRC/NCRI, HOVON/SAKK, SWOG and M D Anderson Cancer Center. Leukemia 2015; 29:312-320.
10. Kreso A, Dick J E. Evolution of the Cancer Stem Cell Model. Cell Stem Cell 2014; 14:275-291.
11. Saito Y, Kitamura H, Hijikata A et al. Identification of therapeutic targets for quiescent, chemotherapy-resistant human leukemia stem cells. Sci Transl Med 2010; 2:17ra9.
12. Guzman M L, Rossi R M, Karnischky L et al. The sesquiterpene lactone parthenolide induces apoptosis of human acute myelogenous leukemia stem and progenitor cells. Blood 2005; 105:4163-4169.
13. Li L, Osdal T, Ho Y et al. SIRT1 activation by a c-MYC oncogenic network promotes the maintenance and drug resistance of human FLT3-ITD acute myeloid leukemia stem cells. Cell Stem Cell 2014; 15:431-446.
14. Fong C Y, Gilan O, Lam E Y et al. BET inhibitor resistance emerges from leukaemia stem cells. Nature 2015; 525:538-542.
15. Lechman E R, Gentner B, Ng S W K et al. miR-126 regulates distinct self-renewal outcomes in normal and malignant hematopoietic stem cells. Cancer Cell 2016; in press.
16. Krivtsov A V, Figueroa M E, Sinha A U et al. Cell of origin determines clinically relevant subtypes of MLL-rearranged AML. Leukemia 2013; 27:852-860.
17. Sarry J E, Murphy K, Perry R et al. Human acute myelogenous leukemia stem cells are rare and heterogeneous when assayed in NOD/SCID/IL2Rgammac-deficient mice. J Clin Invest 2011; 121:384-395.
18. Eppert K, Takenaka K, Lechman E R et al. Stem cell gene expression programs influence clinical outcome in human leukemia. Nat Med 2011; 17:1086-1093.
19. Notta F, Doulatov S, Laurenti E, Poeppl A, Jurisica I, Dick J E. Isolation of single human hematopoietic stem cells capable of long-term multilineage engraftment. Science 2011; 333:218-221.
20. Milyavsky M, Gan 01, Trottier M et al. A distinctive DNA damage response in human hematopoietic stem cells reveals an apoptosis-independent role for p53 in self-renewal. Cell Stem Cell 2010; 7:186-197.
21. Laurenti E, Frelin C, Xie S et al. CDK6 levels regulate quiescence exit in human hematopoietic stem cells. Cell Stem Cell 2015; 16:302-313.
22. van Galen P, Kreso A, Mbong N et al. The unfolded protein response governs integrity of the haematopoietic stem-cell pool during stress. Nature 2014; 510:268-272.
23. Pearce D J, Taussig D, Zibara K et al. AML engraftment in the NOD/SCID assay reflects the outcome of AML: implications for our understanding of the heterogeneity of AML. Blood 2006; 107:1166-1173.
24. Chen W C, Yuan J S, Xing Y et al. An integrated analysis of heterogeneous drug responses in acute myeloid leukemia that enables the discovery of predictive biomarkers. Cancer Res 2016; in press.
25. Verhaak R G, Wouters B J, Erpelinck C A et al. Prediction of molecular subtypes in acute myeloid leukemia based on gene expression profiling. Haematologica 2009; 94:131-134.
26. Metzeler K H, Hummel M, Bloomfield C D et al. An 86-probe-set gene-expression signature predicts survival in cytogenetically normal acute myeloid leukemia. Blood 2008; 112:4193-4201.
27. Genomic and epigenomic landscapes of adult de novo acute myeloid leukemia. N Engl J Med 2013; 368:2059-2074.
28. Kohlmann A, Bullinger L, Thiede C et al. Gene expression profiling in AML with normal karyotype can predict mutations for molecular markers and allows novel insights into perturbed biological pathways. Leukemia 2010; 24:1216-1220.
29. Novershtern N, Subramanian A, Lawton L N et al. Densely interconnected transcriptional circuits control cell states in human hematopoiesis. Cell 2011; 144:296-309.
30. *Laurenti* E, Doulatov S, Zandi S et al. The transcriptional architecture of early human hematopoiesis identifies multilevel control of lymphoid commitment. Nat Immunol 2013; 14:756-763.
31. Qiao W, Quon G, Csaszar E, Yu M, Morris Q, Zandstra P W. PERT: a method for expression deconvolution of human blood samples from varied microenvironmental and developmental conditions. PLoS Comput Biol 2012; 8:e1002838.
32. Friedman J, Hastie T, Tibshirani R. Regularization Paths for Generalized Linear Models via Coordinate Descent. J Stat Softw 2010; 33:1-22.
33. Simon N, Friedman J, Hastie T, Tibshirani R. Regularization Paths for Cox's Proportional Hazards Model via Coordinate Descent. J Stat Softw 2011; 39:1-13.
34. Levine J H, Simonds E F, Bendall S C et al. Data-Driven Phenotypic Dissection of AML Reveals Progenitor-like Cells that Correlate with Prognosis. Cell 2015; 162:184-197.
35. Nielsen T, Wallden B, Schaper C et al. Analytical validation of the PAM50-based Prosigna Breast Cancer Prognostic Gene Signature Assay and nCounter Analysis System using formalin-fixed paraffin-embedded breast tumor specimens. BMC Cancer 2014; 14:177.
36. Geiss G K, Bumgarner R E, Birditt B et al. Direct multiplexed measurement of gene expression with color-coded probe pairs. Nat Biotechnol 2008; 26:317-325.
37. Jin L, Hope K J, Zhai Q, Smadja-Joffe F, Dick J E. Targeting of CD44 eradicates human acute myeloid leukemic stem cells. Nat Med 2006; 12:1167-1174.
38. Jin L, Lee E M, Ramshaw H S et al. Monoclonal antibody-mediated targeting of CD123, IL-3 receptor alpha chain, eliminates human acute myeloid leukemic stem cells. Cell Stem Cell 2009; 5:31-42.
39. Schenk T, Chen W C, Goliner S et al. Inhibition of the LSD1 (KDM1A) demethylase reactivates the all-trans-retinoic acid differentiation pathway in acute myeloid leukemia. Nat Med 2012; 18:605-611.
40. Gentles A J, Plevritis S K, Majeti R, Alizadeh A A. Association of a leukemic stem cell gene expression signature with clinical outcomes in acute myeloid leukemia. JAMA 2010; 304:2706-2715.
S1. Eppert K, Takenaka K, Lechman E R et al. Stem cell gene expression programs influence clinical outcome in human leukemia. Nat Med 2011; 17:1086-1093.
S2. Grimwade D, Hills R K, Moorman A V et al. Refinement of cytogenetic classification in acute myeloid leukemia: determination of prognostic significance of rare recurring chromosomal abnormalities among 5876 younger adult patients treated in the United Kingdom Medical Research Council trials. Blood 2010; 116:354-365.
S3. How J, Sykes J, Gupta V et al. Influence of FLT3-internal tandem duplication allele burden and white blood cell count on the outcome in patients with intermediate-risk karyotype acute myeloid leukemia. Cancer 2012; 118:6110-6117.
S4. Du P, Kibbe W A, Lin S M. lumi: a pipeline for processing Illumina microarray. Bioinformatics 2008; 24:1547-1548.
S5. Ritchie M E, Phipson B, Wu D et al. limma powers differential expression analyses for RNA-sequencing and microarray studies. Nucleic Acids Res 2015;43:e47.
S6. Verhaak R G, Wouters B J, Erpelinck C A et al. Prediction of molecular subtypes in acute myeloid leukemia based on gene expression profiling. Haematologica 2009; 94:131-134.
S7. Gautier L, Cope L, Bolstad B M, Irizarry R A. affy-analysis of Affymetrix GeneChip data at the probe level. Bioinformatics 2004; 20:307-315.
S8. Wu J, Irizarry R, MacDonald J, Gentry J. Gcrma: Background adjustment using sequence information. R package. version 2.36.0. http://www.bioconductor.org/packages/release/bioc/html/gcrma.html
S9. Dai M, Wang P, Boyd A D et al. Evolving gene/transcript definitions significantly alter the interpretation of GeneChip data. Nucleic Acids Res 2005;33:e175.
S10. Friedman J, Hastie T, Tibshirani R. Regularization Paths for Generalized Linear Models via Coordinate Descent. J Stat Softw 2010; 33:1-22.
S11. Simon N, Friedman J, Hastie T, Tibshirani R. Regularization Paths for Cox's Proportional Hazards Model via Coordinate Descent. J Stat Softw 2011; 39:1-13.
S12. Metzeler K H, Hummel M, Bloomfield C D et al. An 86-probe-set gene-expression signature predicts survival in cytogenetically normal acute myeloid leukemia. Blood 2008; 112:4193-4201.
S13. Genomic and epigenomic landscapes of adult de novo acute myeloid leukemia. N Engl J Med 2013; 368:2059-2074.
S14. Kohlmann A, Bullinger L, Thiede C et al. Gene expression profiling in AML with normal karyotype can predict mutations for molecular markers and allows novel insights into perturbed biological pathways. Leukemia 2010; 24:1216-1220.
S15. Klein H U, Ruckert C, Kohlmann A et al. Quantitative comparison of microarray experiments with published leukemia related gene expression signatures. BMC Bioinformatics 2009; 10:422.
S16. Geiss G K, Bumgarner R E, Birditt B et al. Direct multiplexed measurement of gene expression with color-coded probe pairs. Nat Biotechnol 2008; 26:317-325.
S17. MacRae T, Sargeant T, Lemieux S, Hebert J, Deneault E, Sauvageau G. RNA-Seq reveals spliceosome and proteasome genes as most consistent transcripts in human cancer cells. PLoS One 2013;8:e72884.
S18. Altschul S F, Gish W, Miller W, Myers E W, Lipman D J. Basic local alignment search tool. J Mol Biol 1990; 215:403-410.
S19. Scott D W, Wright G W, Williams P M et al. Determining cell-of-origin subtypes of diffuse large B-cell lymphoma using gene expression in formalin-fixed paraffin-embedded tissue. Blood 2014; 123:1214-1217.
S20. Nielsen T, Wallden B, Schaper C et al. Analytical validation of the PAM50-based Prosigna Breast Cancer Prognostic Gene Signature Assay and nCounter Analysis System using formalin-fixed paraffin-embedded breast tumor specimens. BMC Cancer 2014; 14:177.
S21. Robin X, Turck N, Hainard A et al. pROC: an open-source package for R and S+ to analyze and compare ROC curves. BMC Bioinformatics 2011; 12:77.
S22. Kundu S, Aulchenko Y S, Van Duijn C M, Janssens A C. PredictABEL: an R package for the assessment of risk prediction models. Eur J Epidemiol 2011; 26:261-264.
S23. Walter R B, Othus M, Burnett A K et al. Resistance prediction in AML: analysis of 4601 patients from MRC/NCRI, HOVON/SAKK, SWOG and M D Anderson Cancer Center. Leukemia 2015; 29:312-320.
S24. Cheson B D, Bennett J M, Kopecky K J et al. Revised recommendations of the International Working Group for Diagnosis, Standardization of Response Criteria, Treatment Outcomes, and Reporting Standards for Therapeutic Trials in Acute Myeloid Leukemia. J Clin Oncol 2003; 21:4642-4649.
S25. Fine J P, Gray R J. A proportional hazards model for the subdistribution of a competing risk. J Am Stat Assoc 1999; 94:496-509.
S26. Therneau T M, Grambsch P M. Modeling Survival Data: Extending the Cox Model. 2000. New York, Springer.
S27. Valk P J, Verhaak R G, Beijen M A et al. Prognostically useful gene-expression profiles in acute myeloid leukemia. N Engl J Med 2004; 350:1617-1628.

TABLE 1

LSC17 Score Retains Prognostic Value in Multivariate Survival Analysis

| | Overall Survival | | | |
|---|---|---|---|---|
| | TCGA AML (n = 183)* | | PM AML (n = 284)* | |
| Covariate | Hazard Ratio (95% CI)† | P-value‡ | Hazard Ratio (95% CI)† | P-value‡ |
| LSC17 Score | 2.50 (1.37-4.58) | 0.002 | 2.49 (1.78-3.48) | <0.001 |
| Age | Stratifier§ | N/A | 1.00 (0.99-1.01) | 0.25 |

TABLE 1-continued

LSC17 Score Retains Prognostic Value in Multivariate Survival Analysis

| | | | | |
|---|---|---|---|---|
| WBC count | 1.01 (1.00-1.015) | 0.004 | 1.00 (1.00-1.00) | 0.003 |
| Favorable Cytogenetics | 0.73 (0.36-1.49) | 0.39 | 0.46 (0.26-0.79) | 0.005 |
| Adverse Cytogenetics | 1.52 (0.80-2.89) | 0.19 | 1.96 (1.33-2.91) | <0.001 |
| Secondary/t-AML | N/A | N/A | 2.39 (1.61-3.54) | <0.001 |

| | TCGA CN-AML (n = 83)* | | PM CN-AML (n = 85)* | |
|---|---|---|---|---|
| Covariate | Hazard Ratio (95% CI)† | P-value‡ | Hazard Ratio (95% CI)† | P-value‡ |
| LSC17 Score | 5.32 (1.27-22.3) | 0.02 | 2.02 (1.04-3.92) | 0.03 |
| Age | Stratifier§ | N/A | 1.01 (0.98-1.03) | 0.40 |
| WBC count | 1.02 (1.00-1.03) | 0.01 | 1.00 (0.99-1.0) | 0.11 |
| NPM1 Mutation | 1.01 (0.26-3.90) | 0.98 | 0.44 (0.22-0.92) | 0.02 |
| FLT3-ITD | 5.23 (1.12-24.4) | 0.03 | 1.96 (0.97-3.95) | 0.05 |
| Secondary/t-AML | N/A | N/A | 2.63 (1.15-6.01) | 0.02 |

| | GSE12417 CN-AML Cohort 1 (n = 156)* | | GSE12417 CN-AML Cohort 2 (n = 68)* | |
|---|---|---|---|---|
| Covariate | Hazard Ratio (95% CI)† | P-value‡ | Hazard Ratio (95% CI)† | P-value‡ |
| LSC17 Score | 2.45 (1.54-3.89) | <0.001 | 2.29 (1.08-4.84) | 0.02 |
| Age | 1.02 (1.00-1.04) | 0.009 | 1.03 (1.00-1.06) | 0.04 |
| WBC count | 1.00 (1.00-1.00) | 0.95 | 1.00 (1.00-1.00) | 0.002 |
| NPM1 Mutation | 0.72 (0.47-1.10) | 0.13 | 0.52 (0.25-1.08) | 0.08 |
| FL73-ITD | 1.88 (1.17-3.02) | 0.009 | 1.08 (0.47-2.48) | 0.85 |
| Secondary/t-AML | 1.49 (0.65-3.42) | 0.34 | 0.56 (0.17-1.83) | 0.34 |

*No. of patients with full clinical annotations are shown.
†The 95% confidence interval is displayed for each hazard ratio calculated by means of multivariate Cox regression analysis.
‡P value was calculated by means of the Wald test.
§Age was used as a stratifying variable in multivariate Cox regression analysis since this parameter (as a covariate) was determined to be violating the proportional hazards assumption by examining its Schoenfeld residuals. Using Age as a stratification parameter corrected the problem.
t-AML, therapy-associated AML

TABLE 2

LSC3 Score Retains Prognostic Value in Multivariate Survival Analysis

| | Overall Survival | | | |
|---|---|---|---|---|
| | GSE15434 CN-LMR (n = 70)* | | PM CN-LMR (n = 29)* | |
| Covariate | Hazard Ratio (95% CI)† | P-value‡ | Hazard Ratio (95% CI)† | P-value‡ |
| LSC3 Score | 8.49 (2.46-29.3) | <0.001 | 6.30 (1.22-32.3) | 0.02 |
| Age | 0.99 (0.94-1.04) | 0.81 | 0.99 (0.93-1.05) | 0.84 |
| WBC count | N/A | N/A | 1.01 (1.00-1.02) | 0.02 |
| Secondary/t-AML | 1.19 (0.34-4.22) | 0.78 | 11.5 (1.42-93.5) | 0.02 |

*No. of patients with full clinical annotations are shown.
†The 95% confidence interval is displayed for each hazard ratio calculated by means of multivariate Cox regression analysis.
‡P value was calculated by means of the Wald test.

TABLE S1

Clinical Characteristics of the 78 AML Patients Analyzed by Xenotransplantation and Microarray GE Analysis

| Characteristic | |
|---|---|
| Female Sex [n (%)] | 27 (34.6) |
| Age at AML Diagnosis [years] | |
| median (range) | 61.6 (20.1-86.2) |
| De novo vs. Secondary AML [n (%)] | |
| De novo AML | 54 (69.2) |
| Secondary AML/t-AML | 23 (29.4) |
| CMML | 1 (1.3) |
| PB WBC count at diagnosis (×10⁹/L) | |
| median (range) | 49.7 (1.3-606) |
| Blast % at diagnosis (×10⁹/L) | n = 60 |
| Median BM Blasts (range) | 80 (23-96) |
| MRC cytogenetic class at diagnosis [n (%)] | n = 67 |
| Favorable | 0 (0) |
| Intermediate | 46 (68.7) |
| Adverse | 21 (31.3) |
| Karyotype [n (%)] | n = 76 |

TABLE S1-continued

Clinical Characteristics of the 78 AML Patients Analyzed by Xenotransplantation and Microarray GE Analysis

| Characteristic | |
| --- | --- |
| Normal karyotype | 34 (50.7) |
| Abnormal karyotype | 42 (55.2) |
| AML subtypes [n (%)] | |
| APL | 0 (0) |
| Non-APL | 78 (100) |
| CN AML- NPM1 [n (%)] | n = 28 |
| NPM1 mutation | 18 (64.3) |
| No NPM1 mutation | 10 (35.7) |
| CN AML- FLT3-ITD [n (%)] | n = 26 |
| FLT3-ITD positive | 13 (50) |
| FL73-ITD negative | 13 (50) |

CMML, chronic myelomonocytic leukemia;
t-AML, therapy-associated AML

TABLE S2

Key Clinical Characteristics of the GSE6891 Signature Training Cohort

| Characteristic | GSE6891 Training Cohort (n = 495) | High LSC17 score subset (n = 248) | Low LSC17 score subset (n = 247) | P-value |
| --- | --- | --- | --- | --- |
| Female Sex [n (%)] | 252 (50.9) | 132 (53.2) | 120 (48.6) | $0.34\chi^2$ |
| Age at AML Diagnosis [years] | | | | |
| median (range) | 46 (15-77) | 47 (15-77) | 45 (15-77) | 0.33† |
| De novo vs. Secondary AML [n (%)] | | | | |
| De novo | 495 (100) | 248 (100) | 247 (100) | N/A |
| Secondary/t-AML | 0 (0) | 0 (0) | 0 (0) | |
| PB WBC count at diagnosis (×10⁹/L) | | | | |
| median (range) | 31 (0.30-510) | 32 (0.8-278) | 30 (0.3-510) | 0.82¶ |
| Blast % at diagnosis (×10⁹/L) | | | | |
| Median BM Blasts (range) | 66 (0-98) | 71 (0-98) | 60 (0-98) | 0.004¶ |
| Cytogenetic risk class at diagnosis [n (%)]* | n = 483 | n = 241 | n = 242 | |
| Favorable | 99 (20.5) | 7 (2.9) | 92 (38) | <0.001‖ |
| Intermediate | 302 (62.5) | 171 (71) | 131 (54.1) | |
| Adverse | 82 (17) | 63 (26.1) | 19 (7.85) | |
| Karyotype [n (%)] | n = 494 | | n = 246 | |
| Normal karyotype | 210 (42.5) | 118 (47.6) | 92 (37.4) | $0.02\chi^2$ |
| Abnormal karyotype | 284 (57.5) | 130 (52.4) | 154 (62.6) | |
| AML subtypes [n (%)] | | | | |
| APL | 23 (4.65) | 4 (1.61) | 19 (7.69) | 0.001‖ |
| Non-APL | 472 (95.4) | 244 (98.4) | 228 (92.3) | |
| CN AML- NPM1 [n (%)] | n = 210 | n = 118 | n = 92 | |
| NPM1 mutation | 124 (59) | 63 (53.4) | 61 (66.3) | $0.08\chi^2$ |
| No NPM1 mutation | 86 (41) | 55 (46.6) | 31 (33.7) | |
| CN AML- FLT3-ITD [n (%)] | n = 210 | n = 118 | n = 92 | |
| FLT3-ITD positive | 93 (44.3) | 71 (60.2) | 22 (23.9) | $<0.001\chi^2$ |
| FLT3-ITD negative | 117 (55.7) | 47 (39.8) | 70 (76.1) | |
| Treatment Response [n (%)] | | | | |
| Complete Response | 394 (79.6) | 175 (70.6) | 219 (88.7) | $<0.001\chi^2$ |
| No Response | 101 (20.4) | 73 (29.4) | 28 (11.3) | |
| Events [n (%)] | | | | |
| Relapse | 202 (40.8) | 117 (47.2) | 85 (34.4) | $0.005\chi^2$ |
| Survival Parameters [days] | | | | |
| Median Overall Survival | 576 | 318 | 3960 | <0.001** |
| Median Event-Free Survival | 3678 | 3003 | 3732 | 0.01** |

†P-value calculated using the Student's t-test
¶P-value calculated using the Wilcoxon rank-sum test
$\chi^2$P-value calculated using Pearson's chi-square test
‖P-value calculated using Fisher's exact test
*Cytogenetic risk groups were defined as per GSE6891 investigators[6, 26]
**P-value calculated using log-rank test

TABLE S3

Key Clinical Characteristics of GSE12417 Cytogenetically Normal AML Cohort 1

| Characteristic | GSE12417 CN-AML cohort 1 (n = 156) | High LSC17 score subset (n = 78) | Low LSC17 score subset (n = 78) | P-value |
|---|---|---|---|---|
| Female Sex [n (%)] | 84 (53.8) | 39 (50) | 45 (57.7) | 0.42$\chi^2$ |
| Age at AML Diagnosis [years] | | | | |
| median (range) | 57 (17-83) | 61 (20-81) | 54.5 (17-83) | 0.03† |
| De novo vs. Secondary AML [n (%)] | | | | |
| De novo | 149 (95.5) | 74 (94.9) | 75 (96.2) | 1.00‖ |
| Secondary/t-AML | 7 (4.49) | 4 (5.13) | 3 (3.85) | |
| PB WBC count at diagnosis (×10$^9$/L) | | | | |
| median (range) | 36.2 (0.095-486) | 45.3 (0.9-486) | 30.6 (0.095-289) | 0.18¶ |
| BM blast % at diagnosis (×10$^9$/L) | n = 153 | n = 77 | n = 76 | |
| median (range) | 85 (20-100) | 90 (20-100) | 80 (20-100) | 0.04¶ |
| NPM1 [n (%)] | | | | |
| NPM1 mutation | 83 (53.2) | 42 (53.8) | 41 (52.6) | 1.00$\chi^2$ |
| No NPM1 mutation | 73 (46.8) | 36 (46.2) | 37 (47.4) | |
| FLT3-ITD [n (%)] | | | | |
| FLT3-ITD positive | 75 (48.1) | 53 (67.9) | 22 (28.2) | <0.001$\chi^2$ |
| FLT3-ITD negative | 81 (51.9) | 25 (32.1) | 56 (71.8) | |
| Treatment Response [n (%)] | | | | |
| Complete Response | 94 (60.3) | 37 (47.4) | 57 (73.1) | 0.001$\chi^2$ |
| No Response | 62 (39.7) | 41 (52.6) | 21 (26.9) | |
| Survival Parameters [days] | | | | |
| Median Overall Survival | 294 | 223 | not reached | <0.001** |
| Median Event-Free Survival | 192 (n = 153) | 83 (n = 76) | 371 (n = 77) | <0.001** |
| Median Relapse-Free Survival | 384 (n = 91) | 178 (n = 36) | 627 (n = 55) | 0.001** |

†P-value calculated using the Student's t-test
¶P-value calculated using the Wilcoxon rank-sum test
$\chi^2$P-value calculated using Pearson's chi-square test
‖P-value calculated using Fisher's exact test
**P-value calculated using log-rank test

TABLE S4

Key Clinical Characteristics of the GSE12417 Cytogenetically Normal AML Cohort 2

| Characteristic | GSE12417 CN-AML cohort 2 (n = 70) | High LSC17 score subset (n = 35) | Low LSC17 score subset (n = 35) | P-value |
|---|---|---|---|---|
| Female Sex [n (%)] | 29 (41.4) | 18 (51.4) | 11 (31.4) | 0.14‖ |
| Age at AML Diagnosis [years] | | | | |
| median (range) | 62 (18-85) | 62 (22-81) | 62 (18-85) | 0.15† |
| De novo vs. Secondary AML [n (%)] | | | | |
| De novo | 62 (88.6) | 28 (80) | 34 (97.1) | 0.05‖ |
| Secondary/t-AML | 8 (11.4) | 7 (20) | 1 (2.86) | |
| PB WBC count at diagnosis (×10$^9$/L) | n = 68 | n = 34 | n = 34 | |
| median (range) | 15 (1-440.3) | 14.0 (1-440.3) | 17.8 (1-280) | 0.85¶ |
| BM blast % at diagnosis (×10$^9$/L) | n = 67 | n = 33 | n = 34 | |
| median (range) | 80 (18-97) | 80 (18-95) | 87.5 (20-97) | 0.26¶ |
| NPM1 [n (%)] | | | | |
| NPM1 mutation | 36 (51.4) | 13 (37.1) | 23 (65.7) | 0.03‖ |
| No NPM1 mutation | 34 (48.6) | 22 (62.9) | 12 (34.3) | |
| FLT3-ITD [n (%)] | | | | |
| FLT3-ITD positive | 19 (27.1) | 14 (40) | 5 (14.3) | 0.03‖ |
| FLT3-ITD negative | 51 (72.9) | 21 (60) | 30 (85.7) | |
| Treatment Response [n (%)] | n = 68 | n = 33 | | |
| Complete Response | 43 (63.2) | 15 (45.5) | 28 (80) | 0.005‖ |
| No Response | 25 (36.8) | 18 (54.5) | 7 (20) | |

TABLE S4-continued

Key Clinical Characteristics of the GSE12417 Cytogenetically Normal AML Cohort 2

| Characteristic | GSE12417 CN-AML cohort 2 (n = 70) | High LSC17 score subset (n = 35) | Low LSC17 score subset (n = 35) | P-value |
|---|---|---|---|---|
| Survival Parameters [days] | | | | |
| Median Overall Survival | 500 | 301 | not reached | 0.001** |
| Median Event-Free Survival | 243 (n = 69) | 120 (n = 34) | 398 | <0.001** |
| Median Relapse-Free Survival | 368 (n = 40) | 183 (n = 14) | not reached (n = 26) | 0.02** |

†P-value calculated using the Student's t-test
¶P-value calculated using the Wilcoxon rank-sum test
‖P-value calculated using Fisher's exact test
**P-value calculated using log-rank test

TABLE S5

Key Clinical Characteristics of the TCGA AML Cohort

| Characteristic | TCGA AML cohort (n = 183) | High LSC17 score subset (n = 92) | Low LSC17 score subset (n = 91) | P-value |
|---|---|---|---|---|
| Female Sex [n (%)] | 85 (46.4) | 39 (42.4) | 46 (50.5) | 0.33$\chi^2$ |
| Age at AML Diagnosis [years] | | | | |
| median (range) | 57 (18-88) | 61 (21-88) | 55 (18-82) | 0.002† |
| PB WBC count at diagnosis (×10$^9$/L) | | | | |
| median (range) | 16.8 (0.5-298.4) | 12.1 (0.5-297.4) | 26.1 (0.6-298.4) | 0.06¶ |
| Blast % at diagnosis (×10$^9$/L) | | | | |
| Median BM Blasts (range) | 72 (30-100) | 73 (30-99) | 72 (30-100) | 0.97¶ |
| Median PB Blasts (range) | 33 (0-98) | 35.5 (0-98) | 33 (0-97) | 0.57¶ |
| AML subtypes [n (%)] | | | | |
| APL | 17 (9.29) | 4 (4.35) | 13 (14.3) | 0.02‖ |
| Non-APL | 166 (90.7) | 88 (95.7) | 78 (85.7) | |
| Cytogenetic risk class at diagnosis [n (%)]* | | | | |
| Favorable | 38 (20.8) | 7 (7.61) | 31 (34.1) | <0.001‖ |
| Intermediate | 105 (57.4) | 53 (57.6) | 52 (57.1) | |
| Adverse | 40 (21.9) | 32 (34.8) | 8 (8.79) | |
| Karyotype [n (%)] | n = 179 | n = 90 | n = 89 | |
| Normal karyotype | 83 (46.4) | 36 (40) | 47 (52.8) | 0.11$\chi^2$ |
| Abnormal karyotype | 96 (53.6) | 54 (60) | 42 (47.2) | |
| Molecular Risk at diagnosis [n (%)] | n = 180 | n = 91 | n = 89 | |
| Favorable | 35 (19.4) | 5 (5.49) | 30 (33.7) | <0.001‖ |
| Intermediate | 98 (54.4) | 50 (54.9) | 48 (53.9) | |
| Adverse | 47 (26.1) | 36 (39.6) | 11 (12.4) | |
| CN AML- NPM1 [n (%)] | n = 83 | n = 36 | n = 47 | |
| NPM1 mutation | 42 (50.6) | 18 (50) | 24 (51.1) | 1.00$\chi^2$ |
| No NPM1 mutation | 41 (49.4) | 18 (50) | 23 (48.9) | |
| CN AML- FLT3-ITD [n (%)] | n = 83 | n = 36 | n = 47 | |
| FLT3-ITD positive | 23 (27.7) | 16 (44.4) | 7 (14.9) | 0.005‖ |
| FLT3-ITD negative | 60 (72.3) | 20 (55.6) | 40 (85.1) | |
| Survival Parameters [days] | | | | |
| Median Overall Survival | 492 | 303 | 1029 | <0.001** |

†P-value calculated using the Student's t-test
¶P-value calculated using the Wilcoxon rank-sum test
$\chi^2$P-value calculated using Pearson's chi-square test
‖P-value calculated using Fisher's exact test
*Cytogenetic and molecular risk groups were defined as per reference[13]
**P-value calculated using log-rank test

TABLE S6

Key Clinical Characteristics of the GSE15434 CN-LMR Cohort

| Characteristic | CN-LMR cohort (n = 70) | High LSC17 score subset (n = 35) | Low LSC17 score subset (n = 35) | P-value |
|---|---|---|---|---|
| Female Sex [n (%)] | 34 (48.6) | 16 (45.7) | 18 (51.4) | 0.81$\chi^2$ |
| Age at AML Diagnosis [years] | | | | |
| median (range) | 54 (30-83) | 57 (36-83) | 51 (30-75) | 0.08† |
| De novo vs. Secondary AML [n (%)] | | | | |
| De novo | 65 (92.9) | 32 (91.4) | 33 (94.3) | 1.00‖ |
| Secondary/t-AML | 5 (7.14) | 3 (8.57) | 2 (5.71) | |
| PB WBC count at diagnosis (×10$^9$/L) | n = 45 | n = 21 | n = 24 | |
| median (range) | 17.9 (0.9-365) | 29.4 (1.6-365) | 14.4 (0.9-86) | 0.11¶ |
| Blast % at diagnosis (×10$^9$/L) | n = 69, 67 | n = 35, 33 | n = 34 | |
| Median BM Blasts (range) | 69 (0-95) | 75 (0-95) | 65.5 (14-95) | 0.11¶ |
| Median PB Blasts (range) | 18 (0-94) | 60 (0-94) | 9 (0-90) | 0.003¶ |
| Karyotype [n (%)] | | | | |
| Normal karyotype | 70 (100) | 35 (100) | 35 (100) | 1.00‖ |
| Abnormal karyotype | 0 (0) | 0 (0) | 0 (0) | |
| Treatment Response [n (%)] | n = 39 | n = 20 | n = 19 | |
| Complete Response | 35 (89.7) | 18 (90) | 17 (89.5) | 1.00‖ |
| No Response | 4 (10.3) | 2 (10) | 2 (10.5) | |
| CN AML- NPM1 [n (%)] | | | | |
| NPM1 mutation | 70 (100) | 35 (100) | 35 (100) | 1.00‖ |
| No NPM1 mutation | 0 (0) | 0 (0) | 0 (0) | |
| CN AML- FLT3-ITD [n (%)] | | | | |
| FLT3-ITD positive | 0 (0) | 0 (0) | 0 (0) | 1.00‖ |
| FLT3-ITD negative | 70 (100) | 35 (100) | 35 (100) | |
| Survival Parameters [days] | | | | |
| Median Overall Survival | 1767 | 679 | not reached | <0.001** |

†P-value calculated using the Student's t-test
¶P-value calculated using the Wilcoxon rank-sum test
$\chi^2$P-value calculated using Pearson's chi-square test
‖P-value calculated using Fisher's exact test
**P-value calculated using log-rank test

TABLE S7

Clinical Characteristics of the PM Cohort

| Characteristic | PM AML (n = 307) | High LSC17 score (n = 154) | Low LSC17 score (n = 153) | P-value |
|---|---|---|---|---|
| Female Sex [n (%)] | 148 (48.2) | 77 (50) | 71 (46.4) | 0.60$\chi^2$ |
| Age at AML Diagnosis [years] | | | | |
| median (range) | 52 (18-81) | 56 (18-81) | 49 (20-81) | <0.001† |
| De novo vs. Secondary AML [n (%)] | | | | |
| De novo | 268 (87.3) | 130 (84.4) | 138 (90.2) | 0.17$\chi^2$ |
| Secondary/t-AML | 39 (12.7) | 24 (15.6) | 15 (9.8) | |
| PB WBC count at diagnosis (×10$^9$/L) | | | | |
| median (range) | 17.6 (0.7-399) | 12.2 (0.7-212) | 26.8 (1.6-399) | <0.001¶ |
| BM blast % at diagnosis (×10$^9$/L) | n = 284 | n = 142 | n = 142 | |
| median (range) | 80 (10-98) | 80 (10-98) | 80 (16-95) | 0.05¶ |
| AML subtypes [n (%)] | n = 251 | n = 126 | n = 125 | |
| APL | 12 (4.78) | 7 (5.56) | 5 (4) | 0.77‖ |
| Non-APL | 239 (95.2) | 119 (94.4) | 120 (96) | |
| Karyotype [n (%)] | n = 284 | n = 141 | n = 143 | |
| Normal karyotype | 141 (49.6) | 61 (43.3) | 80 (55.9) | 0.04$\chi^2$ |
| Abnormal karyotype | 143 (50.4) | 80 (56.7) | 63 (44.1) | |
| MRC Cytogenetic risk class at diagnosis [n (%)] | n = 284 | n = 141 | n = 143 | |
| Favorable | 48 (16.9) | 13 (9.22) | 35 (24.5) | <0.001‖ |
| Intermediate | 196 (69) | 91 (64.5) | 105 (73.4) | |
| Adverse | 40 (14.1) | 37 (26.2) | 3 (2.1) | |
| CN AML- NPM1 [n (%)] | n = 87 | n = 29 | n = 58 | |

TABLE S7-continued

Clinical Characteristics of the PM Cohort

| Characteristic | PM AML (n = 307) | High LSC17 score (n = 154) | Low LSC17 score (n = 153) | P-value |
|---|---|---|---|---|
| NPM1 mutation | 48 (55.2) | 9 (31) | 39 (67.2) | 0.002‖ |
| No NPM1 mutation | 39 (44.8) | 20 (69) | 19 (32.8) | |
| CN AML- FLT3-ITD [n (%)] | n = 95 | n = 34 | n = 61 | |
| FLT3-ITD positive | 23 (24.2) | 8 (23.5) | 15 (24.6) | 1.00‖ |
| FLT3-ITD negative | 72 (75.8) | 26 (76.5) | 46 (75.4) | |
| Treatment Response [n (%)] | n = 306 | n = 153 | n = 153 | |
| Complete Remission | 223 (72.9) | 85 (55.6) | 138 (90.2) | <0.001‖ |
| No Response | 83 (27.1) | 68 (44.4) | 15 (9.8) | |
| Survival Parameters [n (%)] | | | | |
| Median Overall Survival Days | 671 | 400 | 2035 | <0.001** |
| Median Event-Free Survival Days | 301 | 161 | 541 | <0.001** |
| Median Relapse-Free Survival Days | 378 (n = 267) | 265 (n = 118) | 689 (n = 149) | <0.001** |

†P-value calculated using the Student's t-test
¶P-value calculated using the Wilcoxon rank-sum test
$\chi^2$P-value calculated using Pearson's chi-square test
‖P-value calculated using Fisher's exact test
**P-value calculated using log-rank test

TABLE S8

Genes and Microarray Probes Significantly Associated With LSC+ vs. LSC− Samples

| Gene Symbol | Entrez ID | Illumina Probe ID¶ | Log$_2$ Fold Change† | P-value‡ | Affymetrix Probeset ID§ | Signature Gene |
|---|---|---|---|---|---|---|
| CD34 | 947 | ILMN_1732799 | 2.15 | <0.0001 | 209543_s_at | LSC17 |
| SPINK2 | 6691 | ILMN_1763516 | 1.99 | <0.0001 | 206310_at | N/A |
| LAPTM4B | 55353 | ILMN_2101832 | 1.8 | <0.0001 | 214039_s_at | LSC17 |
| HOXA5 | 3202 | ILMN_1753613 | 1.72 | <0.0001 | 213844_at | N/A |
| GUCY1A3 | 2982 | ILMN_1808590 | 1.62 | <0.0001 | 229530_at | N/A |
| SHANK3 | 85358 | ILMN_2317581 | 1.59 | <0.0001 | 227923_at | N/A |
| ANGPT1 | 284 | ILMN_1677723 | 1.51 | <0.0001 | 205609_at | N/A |
| ARHGAP22 | 58504 | ILMN_1676361 | 1.48 | <0.0001 | 206298_at | LSC17 |
| LOC284422 | 284422 | ILMN_1774375 | 1.45 | <0.0001 | 231982_at | LSC17 |
| MYCN | 4613 | ILMN_2219767 | 1.41 | <0.0001 | 209757_s_at | N/A |
| MAMDC2 | 256691 | ILMN_1679391 | 1.4 | <0.0001 | 228885_at | N/A |
| PRSSL1 | 400668 | ILMN_1673605 | 1.4 | <0.0001 | N/A | N/A |
| KIAA0125 | 9834 | ILMN_1707491 | 1.4 | <0.0001 | 206478_at | LSC17 |
| GPSM1 | 26086 | ILMN_1709307 | 1.38 | <0.0001 | 226043_at | N/A |
| HOXA9 | 3205 | ILMN_1739582 | 1.38 | <0.0001 | N/A | N/A |
| MMRN1 | 22915 | ILMN_1660114 | 1.36 | <0.0001 | 205612_at | LSC17 |
| FSCN1 | 6624 | ILMN_1808707 | 1.32 | <0.0001 | 210933_s_at | N/A |
| DNMT3B | 1789 | ILMN_2328972 | 1.31 | <0.0001 | 220668_s_at | LSC17 |
| HOXA6 | 3203 | ILMN_1815570 | 1.28 | <0.0001 | 208557_at | N/A |
| AIF1L | 83543 | ILMN_3246401 | 1.25 | <0.0001 | 223075_s_at | N/A |
| SOCS2 | 8835 | ILMN_1798926 | 1.24 | <0.0001 | 203373_at | LSC17 |
| CDK6 | 1021 | ILMN_1802615 | 1.23 | <0.0001 | 224851_at | LSC17 |
| FAM69B | 138311 | ILMN_1757440 | 1.2 | <0.0001 | 229002_at | N/A |
| NGFRAP1 | 27018 | ILMN_2370091 | 1.2 | <0.0001 | 217963_s_at | LSC17 |
| C3orf54 | 389119 | ILMN_1690454 | 1.2 | <0.0001 | 229507_at | N/A |
| CPXM1 | 56265 | ILMN_1712046 | 1.2 | <0.0001 | 227860_at | LSC17 |
| TNFRSF4 | 7293 | ILMN_2112256 | 1.2 | <0.0001 | 214228_x_at | N/A |
| ZBTB46 | 140685 | ILMN_1710092 | 1.19 | <0.0001 | 227329_at | LSC17 |
| DPYSL3 | 1809 | ILMN_1679262 | 1.16 | <0.0001 | 201431_s_at | LSC17 & LSC3 |
| NYNRIN | 57523 | ILMN_3236858 | 1.15 | <0.0001 | 220911_s_at | LSC17 & LSC3 |
| COL24A1 | 255631 | ILMN_1810996 | 1.13 | <0.0001 | 238732_at | N/A |
| FAM30A | 29064 | ILMN_3187535 | 1.11 | <0.0001 | N/A | N/A |
| C10orf140 | 387640 | ILMN_3239861 | 1.1 | <0.0001 | N/A | N/A |
| SPNS2 | 124976 | ILMN_3301749 | 1.07 | <0.0001 | 225671_at | N/A |
| GPR56 | 9289 | ILMN_2384122 | 1.07 | 0.00054 | 212070_at | LSC17 |
| AKR1C3 | 8644 | ILMN_1713124 | 1.06 | <0.0001 | 209160_at | LSC17 & LSC3 |
| FLT3 | 2322 | ILMN_1766363 | 1.05 | <0.0001 | 206674_at | N/A |
| TFPI | 7035 | ILMN_1707124 | 1.05 | <0.0001 | 213258_at | N/A |
| KCNK17 | 89822 | ILMN_1717702 | 1.04 | <0.0001 | 224049_at | N/A |
| EPDR1 | 54749 | ILMN_1675797 | 1.03 | <0.0001 | 223253_at | N/A |
| C1orf150 | 148823 | ILMN_1762204 | 1.02 | <0.0001 | N/A | N/A |
| BIVM | 54841 | ILMN_2214098 | 1.02 | <0.0001 | 222761_at | N/A |
| H2AFY2 | 55506 | ILMN_1705570 | 1.02 | <0.0001 | 218445_at | N/A |
| VWF | 7450 | ILMN_1752755 | 1.02 | 0.000103 | 202112_at | N/A |

TABLE S8-continued

Genes and Microarray Probes Significantly Associated With LSC+ vs. LSC− Samples

| Gene Symbol | Entrez ID | Illumina Probe ID¶ | Log$_2$ Fold Change† | P-value‡ | Affymetrix Probeset ID§ | Signature Gene |
| --- | --- | --- | --- | --- | --- | --- |
| EMP1 | 2012 | ILMN_1801616 | 1.01 | <0.0001 | 201324_at | LSC17 |
| RAGE | 5891 | ILMN_1745282 | 1.01 | <0.0001 | 205130_at | N/A |
| ATP8B4 | 79895 | ILMN_1783956 | 1.01 | <0.0001 | 220416_at | N/A |
| GATA2 | 2624 | ILMN_2102670 | 1 | <0.0001 | 209710_at | N/A |
| SLC25A37 | 51312 | ILMN_1715969 | −1.01 | <0.0001 | 222528_s_at | N/A |
| SGK | 6446 | ILMN_3305938 | −1.01 | <0.0001 | 201739_at | N/A |
| LOC652694 | 652694 | ILMN_1680274 | −1.01 | <0.0001 | N/A | N/A |
| ITPR3 | 3710 | ILMN_1815500 | −1.02 | <0.0001 | 201187_s_at | N/A |
| LOC654103 | 654103 | ILMN_1802808 | −1.02 | <0.0001 | N/A | N/A |
| CXCR4 | 7852 | ILMN_1801584 | −1.04 | <0.0001 | 217028_at | N/A |
| FCRL3 | 115352 | ILMN_1691693 | −1.05 | <0.0001 | N/A | N/A |
| RBM38 | 55544 | ILMN_2404049 | −1.05 | <0.0001 | 212430_at | N/A |
| LILRA5 | 353514 | ILMN_2357419 | −1.06 | <0.0001 | 215838_at | N/A |
| IL18RAP | 8807 | ILMN_1721762 | −1.06 | <0.0001 | 207072_at | N/A |
| CCDC109B | 55013 | ILMN_1801766 | −1.08 | <0.0001 | 218802_at | N/A |
| ISG20 | 3669 | ILMN_1659913 | −1.09 | <0.0001 | 33304_at | N/A |
| MTSS1 | 9788 | ILMN_2073289 | −1.09 | <0.0001 | 203037_s_at | N/A |
| CECR1 | 51816 | ILMN_1751851 | −1.1 | <0.0001 | 219505_at | N/A |
| ADAM19 | 8728 | ILMN_1713751 | −1.1 | <0.0001 | 209765_at | N/A |
| FCGR2A | 2212 | ILMN_1666932 | −1.11 | <0.0001 | N/A | N/A |
| AIM2 | 9447 | ILMN_1681301 | −1.11 | <0.0001 | 206513_at | N/A |
| NPL | 80896 | ILMN_1782070 | −1.14 | <0.0001 | 223405_at | N/A |
| IL10RA | 3587 | ILMN_1652825 | −1.15 | <0.0001 | 204912_at | N/A |
| CTSL1 | 1514 | ILMN_1812995 | −1.16 | <0.0001 | 202087_s_at | N/A |
| GNLY | 10578 | ILMN_1708779 | −1.19 | <0.0001 | 205495_s_at | N/A |
| CKAP4 | 10970 | ILMN_1790891 | −1.19 | <0.0001 | 200999_s_at | N/A |
| ADM | 133 | ILMN_1708934 | −1.19 | <0.0001 | 202912_at | N/A |
| KLRB1 | 3820 | ILMN_2079655 | −1.19 | <0.0001 | 214470_at | N/A |
| SLC15A3 | 51296 | ILMN_2085862 | −1.21 | <0.0001 | 219593_at | N/A |
| FGR | 2268 | ILMN_1795158 | −1.22 | <0.0001 | 208438_s_at | N/A |
| FCRLA | 84824 | ILMN_1691071 | −1.22 | <0.0001 | 235372_at | N/A |
| IL2RB | 3560 | ILMN_1684349 | −1.23 | <0.0001 | 205291_at | N/A |
| CXCL16 | 58191 | ILMN_1728478 | −1.24 | <0.0001 | 223454_at | N/A |
| SLC4A1 | 6521 | ILMN_1772809 | −1.24 | <0.0001 | 205592_at | N/A |
| GZMH | 2999 | ILMN_1731233 | −1.27 | <0.0001 | 210321_at | N/A |
| FLJ22662 | 79887 | ILMN_1707286 | −1.27 | <0.0001 | 218454_at | N/A |
| LOC647506 | 647506 | ILMN_3240375 | −1.28 | <0.0001 | N/A | N/A |
| GIMAP4 | 55303 | ILMN_1748473 | −1.29 | <0.0001 | 219243_at | N/A |
| JAZF1 | 221895 | ILMN_1682727 | −1.32 | <0.0001 | 225798_at | N/A |
| CTSH | 1512 | ILMN_2390853 | −1.33 | <0.0001 | 202295_s_at | N/A |
| GZMA | 3001 | ILMN_1779324 | −1.35 | <0.0001 | 205488_at | N/A |
| CHST15 | 51363 | ILMN_1670926 | −1.35 | <0.0001 | 203066_at | N/A |
| AQP9 | 366 | ILMN_1715068 | −1.4 | <0.0001 | 205568_at | N/A |
| CD247 | 919 | ILMN_1676924 | −1.41 | <0.0001 | 210031_at | N/A |
| BCL6 | 604 | ILMN_1737314 | −1.42 | <0.0001 | 203140_at | N/A |
| SLC7A7 | 9056 | ILMN_1810275 | −1.43 | <0.0001 | 204588_s_at | N/A |
| E2F2 | 1870 | ILMN_1777233 | −1.45 | <0.0001 | 228361_at | N/A |
| LOC647450 | 647450 | ILMN_1699214 | −1.45 | <0.0001 | N/A | N/A |
| GZMB | 3002 | ILMN_2109489 | −1.47 | <0.0001 | 210164_at | N/A |
| LOC652493 | 652493 | ILMN_1739508 | −1.61 | <0.0001 | N/A | N/A |
| HBM | 3042 | ILMN_2091454 | −1.62 | <0.0001 | 240336_at | N/A |
| CD14 | 929 | ILMN_2396444 | −1.74 | <0.0001 | 201743_at | N/A |
| ALAS2 | 212 | ILMN_2367126 | −1.76 | <0.0001 | 211560_s_at | N/A |
| HBB | 3043 | ILMN_2100437 | −1.78 | <0.0001 | 209116_x_at | N/A |
| LOC642113 | 642113 | ILMN_1652199 | −1.79 | <0.0001 | N/A | N/A |
| AHSP | 51327 | ILMN_1696512 | −1.84 | <0.0001 | 219672_at | N/A |
| FCN1 | 2219 | ILMN_1668063 | −1.85 | <0.0001 | 205237_at | N/A |
| CD48 | 962 | ILMN_2061043 | −1.85 | <0.0001 | 204118_at | N/A |
| HBA2 | 3040 | ILMN_2127842 | −2.06 | <0.0001 | N/A | N/A |
| HBA1 | 3039 | ILMN_3240144 | −2.07 | <0.0001 | N/A | N/A |

†Fold change in gene expression was calculated between LSC+ vs. LSC− profiles. Positive values indicate higher expression in LSC+ sorted cell fractions.
‡P values for the fold changes were calculated using empirical Bayes moderated t-test while the Benjamini-Hochberg method was used to control for multiple testing.
§Affymetrix probesets chosen to represent the genes of interest are those with the maximum mean expression of all probesets for the genes in the GSE6891 training data
¶Illumine probes chosen to represent the genes of interest are those that have the maximum fold change between LSC+ vs. LSC− profiles in the PM LSC gene identification data

TABLE S9

Multivariate Survival Analysis of the LSC17 Scores Applied to RNA-Seq

| | Overall Survival | | | |
|---|---|---|---|---|
| | TCGA AML RNA-Seq (n = 166)* | | TCGA CN-AML RNA-Seq (n = 76)* | |
| Covariate | Hazard Ratio (95% CI)† | P-value‡ | Hazard Ratio (95% CI)† | P-value‡ |
| LSC17 Score | 1.91 (1.23-2.98) | 0.003 | 2.44 (1.25-4.77) | 0.008 |
| Age | 1.03 (1.02-1.05) | <0.001 | 1.02 (1.00-1.046) | 0.02 |
| WBC count | 1.01 (1.00-1.01) | <0.001 | 1.01 (1.00-1.01) | 0.002 |
| NPM1 Mutation | N/A | N/A | 0.96 (0.53-1.74) | 0.90 |
| FLT3-ITD Mutation | N/A | N/A | 1.28 (0.64-2.56) | 0.48 |
| Favorable Cytogenetics | 0.71 (0.37-1.36) | 0.30 | N/A | N/A |
| Adverse Cytogenetics | 1.57 (1.02-2.41) | 0.04 | N/A | N/A |

*No. of patients with full clinical annotations are shown.
†The 95% confidence interval is displayed for each hazard ratio calculated by means of multivariate Cox regression analysis.
‡P value was calculated by means of the Wald test.
§ Age was used as a stratifying variable in multivariate Cox regression analysis since this parameter (as a covariate was determined to be violating the proportional hazards assumption by examining its Schoenfeld residuals. Using Age as a stratification parameter corrected the problem.

TABLE S10

The Functionally-Defined LSC17 Signature Scores vs. the SDPC Signature

| | Overall Survival | | | |
|---|---|---|---|---|
| | GSE12417 CN-AML Cohort 1 Univariate Analysis (n = 156)* | | TCGA AML Univariate Analysis (n = 183)* | |
| Covariate | Hazard Ratio (95% CI)† | P-value‡ | Hazard Ratio (95% CI)† | P-value‡ |
| SDPC Signature Score | 2.26 (1.50-3.40) | <0.001 | 0.96 (0.68-1.35) | 0.82 |

| | GSE12417 CN-AML Cohort 1 Multivariate Analysis 1 | | TCGA AML Multivariate Analysis 1 | |
|---|---|---|---|---|
| Covariate | Hazard Ratio (95% CI)† | P-value‡ | Hazard Ratio (95% CI)† | P-value‡ |
| SDPC Signature Score | 1.62 (0.99-2.65) | 0.05 | 0.88 (0.51-1.53) | 0.66 |
| Age | 1.02 (1.01-1.040) | 0.002 | Stratifier§ | N/A |
| WBC count | 1.00 (1.00-1.00) | 0.80 | 1.00 (1.00-1.013) | 0.01 |
| Favorable Cytogenetics | N/A | N/A | 0.60 (0.29-1.21) | 0.15 |
| Adverse Cytogenetics | N/A | N/A | 1.91 (1.00-3.65) | 0.04 |
| Secondary/t-AML | 1.67 (0.72-3.85) | 0.22 | N/A | N/A |
| FLT3-ITD Mutation | 2.19 (1.36-3.51) | 0.001 | N/A | N/A |
| NPM1 Mutation | 0.94 (0.59-1.49) | 0.80 | N/A | N/A |

| | GSE12417 CN-AML Cohort 1 Multivariate Analysis 2 (P < 0.001)¶ | | TCGA AML Multivariate Analysis 2 (P = 0.001)¶ | |
|---|---|---|---|---|
| Covariate | Hazard Ratio (95% CI)† | P-value‡ | Hazard Ratio (95% CI)† | P-value‡ |
| LSC17 Score | 2.31 (1.42-3.76) | <0.001 | 2.67 (1.45-4.92) | 0.001 |
| SDPC Signature Score | 1.20 (0.73-1.98) | 0.46 | 0.71 (0.40-1.26) | 0.24 |
| Age | 1.02 (1.00-1.03) | 0.01 | Stratifier§ | N/A |
| WBC count | 1.00 (1.00-1.00) | 0.92 | 1.01 (1.00-1.01) | 0.006 |
| Favorable Cytogenetics | N/A | N/A | 0.84 (0.39-1.77) | 0.64 |
| Adverse Cytogenetics | N/A | N/A | 1.70 (0.86-3.36) | 0.12 |
| Secondary/t-AML | 1.54 (0.67-3.55) | 0.30 | N/A | N/A |
| FLT3-ITD Mutation | 1.81 (1.11-2.94) | 0.01 | N/A | N/A |
| NPM1 Mutation | 0.77 (0.48-1.23) | 0.27 | N/A | N/A |

*No. of patients with full clinical annotations are shown.
†The 95% confidence interval is displayed for each hazard ratio calculated by means of multivariate Cox regression analysis.
‡P value was calculated by means of the Wald test.
§Age was used as a stratifying variable in multivariate Cox regression analysis since this parameter (as a covariate) was determined to be violating the proportional hazards assumption by examining its Schoenfeld residuals. Using Age as a stratification parameter corrected the problem.
¶Inclusion of LSC17 scores in multivariate model 2 for GSE12417 CN-AML Cohort 1 significantly improves predictions of patient outcomes compared to multivariate model 1.

TABLE S11

The Functionally-Defined LSC17 Signature Scores vs. the IFPC Signature

| | Overall Survival | | | |
|---|---|---|---|---|
| | GSE12417 CN-AML Cohort 1 Univariate Analysis (n = 156)* | | TCGA AML Univariate Analysis (n = 183)* | |
| Covariate | Hazard Ratio (95% CI)† | P-value‡ | Hazard Ratio (95% CI)† | P-value‡ |
| IFPC Signature Score | 2.18 (1.45-3.27) | <0.001 | 1.19 (0.85-1.68) | 0.30 |
| | GSE12417 CN-AML Cohort 1 Multivariate Analysis 1 | | TCGA AML Multivariate Analysis 1 | |
| Covariate | Hazard Ratio (95% CI)† | P-value‡ | Hazard Ratio (95% CI)† | P-value‡ |
| IFPC Signature Score | 1.55 (0.98-2.46) | 0.06 | 1.37 (0.79-2.35) | 0.25 |
| Age | 1.02 (1.00-1.040) | 0.004 | Stratifier§ | N/A |
| WBC count | 1.00 (1.00-1.00) | 0.93 | 1.00 (1.00-1.01) | 0.007 |
| Favorable Cytogenetics | N/A | N/A | 0.55 (0.28-1.09) | 0.08 |
| Adverse Cytogenetics | N/A | N/A | 1.73 (0.93-3.22) | 0.07 |
| Secondary/t-AML | 1.57 (0.68-3.60) | 0.28 | N/A | N/A |
| FLT3-ITD Mutation | 2.15 (1.34-3.46) | 0.001 | N/A | N/A |
| NPM1 Mutation | 0.76 (0.50-1.16) | 0.21 | N/A | N/A |
| | GSE12417 CN-AML Cohort 1 Multivariate Analysis 2 (P < 0.001)¶ | | TCGA AML Multivariate Analysis 2 (P = 0.003)¶ | |
| Covariate | Hazard Ratio (95% CI)† | P-value‡ | Hazard Ratio (95% CI)† | P-value‡ |
| LSC17 Score | 2.31 (1.44-3.71) | <0.001 | 2.47 (1.30-4.69) | 0.005 |
| IFPC Signature Score | 1.28 (0.81-2.04) | 0.23 | 1.03 (0.58-1.83) | 0.91 |
| Age | 1.02 (1.00-1.03) | 0.01 | Stratifier§ | N/A |
| WBC count | 1.00 (1.00-1.00) | 0.99 | 1.01 (1.00-1.01) | 0.004 |
| Favorable Cytogenetics | N/A | N/A | 0.73 (0.35-1.49) | 0.38 |
| Adverse Cytogenetics | N/A | N/A | 1.51 (0.79-2.89) | 0.20 |
| Secondary/t-AML | 1.52 (0.66-3.48) | 0.32 | N/A | N/A |
| FLT3-ITD Mutation | 1.75 (1.07-2.85) | 0.02 | N/A | N/A |
| NPM1 Mutation | 0.71 (0.46-1.09) | 0.12 | N/A | N/A |

*No. of patients with full clinical annotations are shown.
†The 95% confidence interval is displayed for each hazard ratio calculated by means of multivariate Cox regression analysis.
‡P value was calculated by means of the Wald test.
§Age was used as a stratifying variable in multivariate Cox regression analysis since this parameter (as a covariate) was determined to be violating the proportional hazards assumption by examining its Schoenfeld residuals. Using Age as a stratification parameter corrected the problem.
¶Inclusion of the LSC17 scores in multivariate model 2 for GSE12417 CN-AML Cohort 1 significantly improves predictions of patient outcomes compared to multivariate model 1.

TABLE S12

Multivariate Logistic Regression Models for Failure to Achieve Initial CR

| Overall Survival | PM AML (n = 283)* | | PM AML (n = 283)* | | PM AML (n = 283)* | |
|---|---|---|---|---|---|---|
| Covariate | Odds Ratio (95% CI)† | P-value‡ | Odds Ratio (95% CI)† | P-value‡ | Odds Ratio (95% CI)† | P-value‡ |
| LSC17 Score | N/A | N/A | 112.6 (29.2-433.8) | <0.001 | 58.4 (13.3-255.4) | <0.001 |
| Age | 0.99 (0.97-1.01) | 0.36 | 0.98 (0.96-1.00) | 0.13 | 0.98 (0.95-1.00) | 0.07 |
| WBC count | 1.00 (0.99-1.01) | 0.21 | 1.00 (1.00 = 1.01) | 0.002 | 1.01 (1.00-1.01) | 0.003 |
| Favorable Cytogenetics | 0.14 (0.03-0.61) | 0.009 | N/A | N/A | 0.20 (0.04-0.92) | 0.04 |
| Adverse Cytogenetics | 6.17 (2.89-13.1) | <0.001 | N/A | N/A | 3.01 (1.30-6.96) | 0.009 |
| Secondary AML | 2.77 (1.21-6.30) | 0.01 | 2.25 (0.98-5.17) | 0.05 | 2.51 (1.01-6.23) | 0.04 |
| ba-AUROC | 0.73 | | 0.79 | | 0.82 | |

*No. of patients with full clinical annotations are shown.
†The 95% confidence interval is displayed for each hazard ratio calculated by means of multivariate Cox regression analysis.
‡P value was calculated by means of the Wald test.

TABLE S13

| ID | DNMT38 | Z6TB46 | NYN81N | ARHGAP22 | LAPTM4B | MMRN1 | DPYSL3 | KIAA0125 | CDK6 | CPKM1 | SOSC2 | LOC284422 | EMP1 | NGFRAP1 | CD34 | AKR1C3 | GPR56 | Average Univariate Hazard Ratio |
|---|---|---|---|---|---|---|---|---|---|---|---|---|---|---|---|---|---|---|
| 131071 | 0.087 | -0.035 | 0.009 | -0.014 | 0.006 | 0.026 | 0.028 | 0.020 | -0.070 | -0.026 | 0.027 | -0.023 | 0.015 | 0.046 | 0.034 | -0.040 | 0.050 | 2.815 |
| 131022 | 0.087 | -0.035 | 0.000 | 0.000 | 0.006 | 0.026 | 0.028 | 0.020 | -0.070 | -0.026 | 0.027 | -0.023 | 0.015 | 0.046 | 0.034 | -0.040 | 0.050 | 2.819 |
| 40427 | 0.000 | 0.000 | 0.000 | 0.000 | 0.006 | 0.000 | 0.000 | 0.000 | 0.000 | 0.000 | 0.000 | -0.023 | 0.000 | 0.046 | 0.034 | -0.040 | 0.000 | 2.819 |
| 130583 | 0.087 | -0.035 | 0.009 | 0.000 | 0.006 | 0.000 | 0.028 | 0.020 | -0.070 | -0.026 | 0.027 | -0.023 | 0.015 | 0.046 | 0.034 | -0.040 | 0.050 | 2.819 |
| 111284 | 0.087 | -0.035 | 0.000 | -0.014 | 0.000 | 0.026 | 0.028 | 0.020 | -0.070 | -0.026 | 0.027 | -0.023 | 0.015 | 0.000 | 0.034 | -0.040 | 0.050 | 2.819 |
| 113530 | 0.087 | -0.035 | 0.000 | -0.014 | 0.006 | 0.000 | 0.028 | 0.020 | -0.070 | -0.026 | 0.027 | -0.023 | 0.015 | 0.046 | 0.034 | -0.040 | 0.050 | 2.819 |
| 122903 | 0.087 | -0.035 | 0.009 | -0.014 | 0.000 | 0.000 | 0.028 | 0.000 | -0.070 | 0.000 | 0.027 | -0.023 | 0.015 | 0.046 | 0.034 | -0.040 | 0.050 | 2.819 |
| 130193 | 0.000 | 0.000 | 0.000 | -0.014 | 0.006 | 0.000 | 0.000 | 0.000 | -0.070 | -0.026 | 0.027 | 0.000 | 0.015 | 0.046 | 0.034 | -0.040 | 0.050 | 2.820 |
| 108765 | 0.087 | 0.000 | 0.009 | -0.014 | 0.006 | 0.000 | 0.000 | 0.020 | -0.070 | 0.000 | 0.027 | -0.023 | 0.015 | 0.046 | 0.034 | 0.000 | 0.050 | 2.820 |
| 100066 | 0.087 | 0.000 | 0.000 | -0.014 | 0.006 | 0.000 | 0.000 | 0.000 | -0.070 | 0.000 | 0.027 | -0.023 | 0.015 | 0.046 | 0.034 | 0.000 | 0.050 | 2.821 |
| 107014 | 0.000 | 0.000 | 0.009 | -0.014 | 0.006 | 0.000 | 0.000 | 0.020 | -0.070 | 0.000 | 0.027 | -0.023 | 0.015 | 0.046 | 0.034 | 0.000 | 0.050 | 2.822 |
| 129144 | 0.087 | -0.035 | 0.000 | -0.014 | 0.000 | 0.000 | 0.028 | 0.020 | -0.070 | -0.026 | 0.027 | -0.023 | 0.015 | 0.046 | 0.034 | -0.040 | 0.050 | 2.822 |
| 130523 | 0.000 | -0.035 | 0.000 | -0.014 | 0.000 | 0.000 | 0.000 | 0.020 | -0.070 | 0.000 | 0.027 | -0.023 | 0.015 | 0.046 | 0.034 | -0.040 | 0.050 | 2.822 |
| 35921 | 0.000 | 0.000 | 0.009 | -0.014 | 0.006 | 0.000 | 0.000 | 0.020 | -0.070 | 0.000 | 0.027 | -0.023 | 0.000 | 0.046 | 0.034 | 0.000 | 0.050 | 2.823 |
| 85606 | 0.087 | -0.035 | 0.000 | -0.014 | 0.000 | 0.000 | 0.000 | 0.020 | -0.070 | -0.026 | 0.027 | -0.023 | 0.000 | 0.046 | 0.034 | -0.040 | 0.000 | 2.831 |
| 129136 | 0.000 | 0.000 | 0.009 | -0.014 | 0.000 | 0.000 | 0.028 | 0.020 | -0.070 | 0.000 | 0.027 | -0.023 | 0.000 | 0.046 | 0.034 | -0.040 | 0.050 | 2.832 |
| 116335 | 0.087 | -0.035 | 0.000 | -0.014 | 0.006 | 0.026 | 0.028 | 0.020 | -0.070 | -0.026 | 0.027 | -0.023 | 0.000 | 0.000 | 0.034 | -0.040 | 0.050 | 2.832 |
| 124359 | 0.087 | -0.035 | 0.000 | -0.014 | 0.000 | 0.000 | 0.028 | 0.000 | -0.070 | -0.026 | 0.027 | -0.023 | 0.000 | 0.046 | 0.034 | -0.040 | 0.050 | 2.833 |
| 19905 | 0.000 | 0.000 | 0.000 | -0.014 | 0.000 | 0.000 | 0.028 | 0.020 | -0.070 | 0.000 | 0.027 | 0.000 | 0.015 | 0.046 | 0.034 | 0.000 | 0.050 | 2.834 |
| 66479 | 0.000 | 0.000 | 0.000 | -0.014 | 0.006 | 0.000 | 0.000 | 0.020 | -0.070 | 0.000 | 0.027 | -0.023 | 0.000 | 0.046 | 0.034 | 0.000 | 0.050 | 2.835 |
| 124343 | 0.087 | -0.035 | 0.009 | -0.014 | 0.000 | 0.000 | 0.028 | 0.000 | -0.070 | -0.026 | 0.027 | -0.023 | 0.015 | 0.046 | 0.034 | -0.040 | 0.050 | 2.836 |
| 21683 | 0.000 | 0.000 | 0.009 | 0.000 | 0.000 | 0.000 | 0.000 | 0.020 | 0.000 | 0.000 | 0.027 | 0.000 | 0.015 | 0.046 | 0.034 | 0.000 | 0.050 | 2.836 |
| 130691 | 0.087 | -0.035 | 0.000 | -0.014 | 0.000 | 0.000 | 0.028 | 0.020 | -0.070 | -0.026 | 0.000 | -0.023 | 0.015 | 0.046 | 0.034 | -0.040 | 0.050 | 2.837 |
| 131007 | 0.087 | -0.035 | 0.009 | 0.000 | 0.006 | 0.000 | 0.028 | 0.020 | -0.070 | -0.026 | 0.027 | -0.023 | 0.015 | 0.046 | 0.034 | -0.040 | 0.050 | 2.838 |
| 60815 | 0.000 | 0.000 | 0.000 | -0.014 | 0.000 | 0.000 | 0.000 | 0.020 | -0.070 | 0.000 | 0.027 | 0.000 | 0.015 | 0.046 | 0.034 | 0.000 | 0.050 | 2.838 |
| 64171 | 0.087 | -0.035 | 0.009 | -0.014 | 0.006 | 0.000 | 0.000 | 0.020 | -0.070 | -0.026 | 0.027 | -0.023 | 0.015 | 0.046 | 0.034 | -0.040 | 0.050 | 2.839 |
| 129043 | 0.000 | 0.000 | 0.000 | -0.014 | 0.006 | 0.000 | 0.028 | 0.020 | -0.070 | 0.000 | 0.027 | -0.023 | 0.000 | 0.046 | 0.034 | 0.000 | 0.050 | 2.840 |
| 66736 | 0.087 | -0.035 | 0.009 | -0.014 | 0.006 | 0.026 | 0.000 | 0.000 | -0.070 | -0.026 | 0.027 | -0.023 | 0.015 | 0.046 | 0.034 | -0.040 | 0.050 | 2.841 |
| 18754 | 0.087 | 0.000 | 0.000 | 0.000 | 0.000 | 0.000 | 0.000 | 0.020 | -0.070 | 0.000 | 0.027 | -0.023 | 0.000 | 0.046 | 0.034 | 0.000 | 0.050 | 2.843 |
| 112273 | 0.000 | -0.035 | 0.009 | -0.014 | 0.000 | 0.000 | 0.028 | 0.020 | 0.000 | -0.026 | 0.000 | -0.023 | 0.015 | 0.046 | 0.034 | -0.040 | 0.050 | 2.844 |
| 40339 | 0.000 | 0.000 | 0.000 | -0.014 | 0.006 | 0.000 | 0.028 | 0.000 | -0.070 | 0.000 | 0.027 | 0.000 | 0.015 | 0.046 | 0.034 | -0.040 | 0.000 | 2.845 |
| 131020 | 0.087 | -0.035 | 0.000 | -0.014 | 0.006 | 0.000 | 0.000 | 0.020 | -0.070 | -0.026 | 0.027 | -0.023 | 0.015 | 0.046 | 0.034 | -0.040 | 0.050 | 2.846 |
| 131065 | 0.087 | -0.035 | 0.000 | -0.014 | 0.000 | 0.000 | 0.028 | 0.020 | -0.070 | -0.026 | 0.027 | -0.023 | 0.015 | 0.046 | 0.034 | -0.040 | 0.050 | 2.846 |
| 64016 | 0.087 | 0.000 | 0.009 | 0.000 | 0.006 | 0.000 | 0.000 | 0.000 | -0.070 | 0.000 | 0.000 | 0.000 | 0.000 | 0.046 | 0.034 | 0.000 | 0.050 | 2.846 |
| 130662 | 0.087 | -0.035 | 0.009 | -0.014 | 0.006 | 0.000 | 0.000 | 0.020 | -0.070 | -0.026 | 0.027 | -0.023 | 0.015 | 0.046 | 0.034 | -0.040 | 0.050 | 2.848 |
| 99282 | 0.087 | 0.000 | 0.000 | -0.014 | 0.000 | 0.000 | 0.028 | 0.000 | 0.000 | -0.026 | 0.027 | 0.000 | 0.000 | 0.046 | 0.034 | -0.040 | 0.050 | 2.848 |
| 130417 | 0.087 | -0.035 | 0.009 | -0.014 | 0.006 | 0.000 | 0.028 | 0.020 | -0.070 | -0.026 | 0.027 | -0.023 | 0.015 | 0.046 | 0.034 | -0.040 | 0.050 | 2.849 |
| 77099 | 0.087 | 0.000 | 0.000 | -0.014 | 0.000 | 0.000 | 0.000 | 0.000 | -0.070 | 0.000 | 0.000 | -0.023 | 0.015 | 0.046 | 0.034 | 0.000 | 0.050 | 2.852 |

TABLE S13-continued

| ID | DNMT3B | Z6TB46 | NYN81N | ARHGAP22 | LAPTM4B | MMRN1 | DPYSL3 | KIAA0125 | CDK6 | CPKM1 | SOSC2 | LOC284422 | EMP1 | NGFRAP1 | CD34 | AKR1C3 | GPR56 | Average Univariate Hazard Ratio |
|---|---|---|---|---|---|---|---|---|---|---|---|---|---|---|---|---|---|---|
| 97977 | 0.087 | 0.000 | 0.009 | -0.014 | 0.000 | 0.000 | 0.000 | 0.000 | -0.070 | -0.026 | 0.000 | -0.023 | 0.015 | 0.046 | 0.034 | 0.000 | 0.050 | 2.853 |
| 128529 | 0.087 | -0.035 | 0.000 | -0.014 | 0.000 | 0.000 | 0.028 | 0.020 | -0.070 | -0.026 | 0.027 | 0.000 | 0.015 | 0.046 | 0.034 | 0.000 | 0.050 | 2.853 |
| 129210 | 0.087 | 0.000 | 0.009 | 0.000 | 0.006 | 0.000 | 0.000 | 0.020 | -0.070 | -0.026 | 0.027 | -0.023 | 0.015 | 0.046 | 0.034 | -0.040 | 0.050 | 2.856 |
| 115521 | 0.087 | -0.035 | 0.009 | -0.014 | 0.000 | 0.000 | 0.028 | 0.000 | -0.070 | -0.026 | 0.000 | -0.023 | 0.015 | 0.046 | 0.034 | 0.000 | 0.050 | 2.857 |
| 71369 | 0.087 | 0.000 | 0.000 | 0.000 | 0.000 | 0.000 | 0.000 | 0.000 | 0.000 | 0.000 | 0.027 | -0.023 | 0.000 | 0.046 | 0.034 | -0.040 | 0.050 | 2.859 |
| 77109 | 0.087 | -0.035 | 0.000 | -0.014 | 0.006 | 0.000 | 0.028 | 0.020 | 0.000 | 0.000 | 0.027 | -0.023 | 0.015 | 0.046 | 0.034 | -0.040 | 0.050 | 2.860 |
| 97987 | 0.087 | 0.000 | 0.009 | -0.014 | 0.000 | 0.026 | 0.028 | 0.020 | 0.000 | 0.000 | 0.000 | 0.000 | 0.015 | 0.046 | 0.034 | -0.040 | 0.050 | 2.860 |
| 106154 | 0.000 | 0.000 | 0.000 | 0.000 | 0.000 | 0.026 | 0.028 | 0.020 | -0.070 | 0.000 | 0.027 | -0.023 | 0.015 | 0.046 | 0.034 | -0.040 | 0.050 | 2.861 |
| 61566 | 0.000 | 0.000 | 0.009 | 0.000 | 0.006 | 0.000 | 0.028 | 0.020 | -0.070 | 0.000 | 0.027 | 0.000 | 0.015 | 0.046 | 0.034 | -0.040 | 0.050 | 2.862 |
| 130589 | 0.000 | -0.035 | 0.000 | 0.000 | 0.006 | 0.000 | 0.000 | 0.020 | -0.070 | 0.000 | 0.027 | -0.023 | 0.015 | 0.046 | 0.034 | 0.000 | 0.000 | 2.862 |
| 55302 | 0.000 | -0.035 | 0.009 | 0.000 | 0.006 | 0.000 | 0.028 | 0.020 | -0.070 | -0.026 | 0.027 | -0.023 | 0.015 | 0.046 | 0.034 | 0.000 | 0.050 | 2.863 |
| 130667 | 0.087 | -0.035 | 0.000 | -0.014 | 0.006 | 0.000 | 0.000 | 0.020 | -0.070 | 0.000 | 0.027 | -0.023 | 0.000 | 0.046 | 0.034 | -0.040 | 0.050 | 2.863 |
| 88558 | 0.000 | 0.000 | 0.000 | -0.014 | 0.006 | 0.000 | 0.028 | 0.020 | -0.070 | 0.000 | 0.027 | 0.000 | 0.000 | 0.046 | 0.034 | 0.000 | 0.050 | 2.863 |
| 107005 | 0.000 | 0.000 | 0.009 | -0.014 | 0.006 | 0.000 | 0.028 | 0.020 | -0.070 | 0.000 | 0.027 | -0.023 | 0.015 | 0.046 | 0.034 | -0.040 | 0.050 | 2.866 |
| 78402 | 0.087 | -0.035 | 0.000 | 0.000 | 0.000 | 0.000 | 0.028 | 0.000 | -0.070 | -0.026 | 0.027 | -0.023 | 0.015 | 0.046 | 0.034 | 0.000 | 0.050 | 2.867 |
| 121586 | 0.000 | 0.000 | 0.000 | -0.014 | 0.006 | 0.000 | 0.028 | 0.020 | -0.070 | 0.000 | 0.027 | -0.023 | 0.015 | 0.046 | 0.034 | -0.040 | 0.050 | 2.868 |
| 127683 | 0.000 | 0.000 | 0.009 | -0.014 | 0.000 | 0.000 | 0.028 | 0.020 | -0.070 | 0.000 | 0.027 | -0.023 | 0.000 | 0.046 | 0.034 | 0.000 | 0.050 | 2.868 |
| 34424 | 0.000 | -0.035 | 0.000 | 0.000 | 0.006 | 0.000 | 0.000 | 0.020 | 0.000 | 0.000 | 0.027 | -0.023 | 0.015 | 0.046 | 0.034 | -0.040 | 0.050 | 2.870 |
| 100506 | 0.087 | 0.000 | 0.009 | -0.014 | 0.006 | 0.000 | 0.000 | 0.000 | -0.070 | -0.026 | 0.027 | -0.023 | 0.015 | 0.046 | 0.034 | 0.000 | 0.000 | 2.870 |
| 130983 | 0.087 | -0.035 | 0.009 | -0.014 | 0.006 | 0.000 | 0.000 | 0.020 | -0.070 | 0.000 | 0.027 | 0.000 | 0.015 | 0.046 | 0.034 | -0.040 | 0.050 | 2.870 |
| 115081 | 0.000 | 0.000 | 0.000 | -0.014 | 0.006 | 0.000 | 0.000 | 0.000 | -0.070 | 0.000 | 0.000 | -0.023 | 0.015 | 0.046 | 0.034 | -0.040 | 0.050 | 2.871 |
| 124113 | 0.087 | -0.035 | 0.009 | -0.014 | 0.000 | 0.000 | 0.028 | 0.000 | -0.070 | 0.000 | 0.027 | -0.023 | 0.015 | 0.046 | 0.034 | -0.040 | 0.050 | 2.872 |
| 128299 | 0.087 | -0.035 | 0.000 | -0.014 | 0.006 | 0.000 | 0.028 | 0.000 | -0.070 | -0.026 | 0.000 | -0.023 | 0.015 | 0.046 | 0.034 | -0.040 | 0.050 | 2.872 |
| 128555 | 0.087 | -0.035 | 0.000 | -0.014 | 0.006 | 0.000 | 0.000 | 0.000 | -0.070 | -0.026 | 0.027 | -0.023 | 0.000 | 0.046 | 0.034 | -0.000 | 0.050 | 2.875 |
| 129075 | 0.087 | -0.035 | 0.009 | -0.014 | 0.006 | 0.000 | 0.028 | 0.020 | -0.070 | 0.020 | 0.027 | -0.023 | 0.015 | 0.046 | 0.034 | -0.040 | 0.050 | 2.879 |
| 130979 | 0.087 | -0.035 | 0.000 | -0.014 | 0.006 | 0.000 | 0.028 | 0.020 | -0.070 | -0.026 | 0.027 | -0.023 | 0.015 | 0.046 | 0.034 | -0.040 | 0.050 | 2.887 |
| 125164 | 0.087 | -0.035 | 0.009 | -0.014 | 0.000 | 0.000 | 0.028 | 0.000 | -0.070 | -0.026 | 0.000 | 0.000 | 0.015 | 0.046 | 0.034 | -0.040 | 0.050 | 2.891 |
| 130663 | 0.087 | -0.035 | 0.009 | -0.014 | 0.006 | 0.000 | 0.028 | 0.020 | -0.070 | -0.026 | 0.027 | -0.023 | 0.015 | 0.046 | 0.034 | -0.040 | 0.050 | 2.892 |
| 129061 | 0.087 | -0.035 | 0.000 | -0.014 | 0.006 | 0.000 | 0.000 | 0.000 | -0.070 | -0.026 | 0.027 | -0.023 | 0.015 | 0.046 | 0.034 | 0.000 | 0.050 | 2.894 |
| 130440 | 0.087 | -0.035 | 0.009 | -0.014 | 0.000 | 0.000 | 0.028 | 0.020 | -0.070 | -0.026 | 0.027 | -0.023 | 0.015 | 0.046 | 0.034 | -0.040 | 0.050 | 2.894 |
| 124162 | 0.087 | -0.035 | 0.009 | -0.014 | 0.006 | 0.000 | 0.000 | 0.000 | -0.070 | -0.026 | 0.027 | -0.023 | 0.000 | 0.046 | 0.034 | -0.040 | 0.050 | 2.898 |
| 113580 | 0.087 | -0.035 | 0.000 | -0.014 | 0.006 | 0.000 | 0.028 | 0.000 | -0.070 | -0.026 | 0.027 | -0.023 | 0.015 | 0.046 | 0.034 | -0.040 | 0.050 | 2.899 |
| 130679 | 0.087 | -0.035 | 0.009 | -0.014 | 0.000 | 0.000 | 0.028 | 0.000 | -0.070 | -0.026 | 0.027 | -0.023 | 0.015 | 0.046 | 0.034 | -0.040 | 0.050 | 2.900 |
| 130995 | 0.087 | -0.035 | 0.000 | -0.014 | 0.006 | 0.000 | 0.000 | 0.020 | -0.070 | -0.026 | 0.027 | -0.023 | 0.015 | 0.046 | 0.034 | -0.040 | 0.050 | 2.900 |
| 113579 | 0.087 | -0.035 | 0.009 | -0.014 | 0.006 | 0.000 | 0.000 | 0.000 | -0.070 | -0.026 | 0.027 | -0.023 | 0.015 | 0.046 | 0.034 | -0.040 | 0.050 | 2.907 |
| 122952 | 0.087 | -0.035 | 0.009 | -0.014 | 0.006 | 0.000 | 0.000 | 0.000 | -0.070 | -0.026 | 0.027 | 0.000 | 0.000 | 0.046 | 0.034 | -0.040 | 0.050 | 2.907 |
| 110988 | 0.087 | -0.035 | 0.000 | -0.014 | 0.000 | 0.000 | 0.000 | 0.000 | -0.070 | -0.026 | 0.027 | -0.023 | 0.000 | 0.046 | 0.034 | -0.040 | 0.050 | 2.910 |
| 94983 | 0.087 | -0.035 | 0.009 | -0.014 | 0.000 | 0.000 | 0.000 | 0.000 | -0.070 | 0.000 | 0.027 | -0.023 | 0.000 | 0.046 | 0.034 | -0.040 | 0.050 | 2.915 |
| 110999 | 0.087 | -0.035 | 0.009 | -0.014 | 0.000 | 0.000 | 0.000 | 0.000 | -0.070 | 0.000 | 0.027 | -0.023 | 0.000 | 0.046 | 0.034 | -0.040 | 0.050 | 2.916 |

TABLE S13-continued

| ID | DNMT3B | Z6TB46 | NYN81N | ARHGAP22 | LAPTM4B | MMRN1 | DPYSL3 | KIAA0125 | CDK6 | CPKM1 | SOSC2 | LOC284422 | EMP1 | NGFRAP1 | CD34 | AKR1C3 | GPR56 | Average Univariate Hazzard Ratio |
|---|---|---|---|---|---|---|---|---|---|---|---|---|---|---|---|---|---|---|
| 113078 | 0.087 | −0.035 | 0.000 | −0.014 | 0.006 | 0.000 | 0.000 | 0.000 | −0.070 | 0.000 | 0.027 | −0.023 | 0.000 | 0.046 | 0.034 | −0.040 | 0.050 | 2.917 |
| 94972 | 0.087 | −0.035 | 0.000 | −0.014 | 0.000 | 0.000 | 0.000 | 0.000 | −0.070 | −0.026 | 0.027 | 0.000 | 0.000 | 0.046 | 0.034 | −0.040 | 0.050 | 2.920 |
| 113582 | 0.087 | −0.035 | 0.000 | −0.014 | 0.000 | 0.000 | 0.000 | 0.000 | −0.070 | 0.000 | 0.027 | −0.023 | 0.015 | 0.046 | 0.034 | −0.040 | 0.050 | 2.930 |
| 122955 | 0.087 | −0.035 | 0.000 | −0.014 | 0.000 | 0.000 | 0.000 | 0.000 | −0.070 | −0.026 | 0.027 | −0.023 | 0.015 | 0.046 | 0.034 | −0.040 | 0.050 | 2.930 |
| 128514 | 0.087 | −0.035 | 0.009 | −0.014 | 0.000 | 0.000 | 0.000 | 0.000 | −0.070 | −0.026 | 0.027 | −0.023 | 0.015 | 0.046 | 0.034 | −0.040 | 0.050 | 2.942 |
| 101062 | 0.087 | 0.000 | 0.000 | 0.000 | 0.006 | 0.000 | 0.000 | 0.000 | −0.070 | −0.026 | 0.027 | 0.000 | 0.015 | 0.046 | 0.034 | −0.040 | 0.050 | 2.942 |
| 122953 | 0.087 | −0.035 | 0.009 | −0.014 | 0.006 | 0.000 | 0.000 | 0.000 | −0.070 | −0.026 | 0.027 | 0.000 | 0.015 | 0.046 | 0.034 | −0.040 | 0.050 | 2.946 |
| 130422 | 0.087 | −0.035 | 0.000 | −0.014 | 0.006 | 0.000 | 0.028 | 0.000 | −0.070 | −0.026 | 0.027 | −0.023 | 0.015 | 0.046 | 0.034 | −0.040 | 0.050 | 2.950 |
| 100567 | 0.087 | −0.035 | 0.000 | −0.014 | 0.000 | 0.000 | 0.000 | 0.000 | −0.070 | −0.026 | 0.027 | −0.023 | 0.015 | 0.046 | 0.034 | −0.040 | 0.050 | 2.953 |
| 124369 | 0.087 | −0.035 | 0.000 | −0.014 | 0.006 | 0.000 | 0.000 | 0.000 | −0.070 | −0.026 | 0.027 | −0.023 | 0.015 | 0.046 | 0.034 | −0.040 | 0.050 | 2.957 |
| 124165 | 0.087 | −0.035 | 0.000 | −0.014 | 0.006 | 0.000 | 0.000 | 0.000 | −0.070 | −0.026 | 0.027 | −0.023 | 0.015 | 0.046 | 0.034 | −0.040 | 0.050 | 2.962 |
| 128351 | 0.087 | −0.035 | 0.000 | −0.014 | 0.006 | 0.000 | 0.000 | 0.000 | −0.070 | −0.026 | 0.027 | −0.023 | 0.015 | 0.046 | 0.034 | −0.040 | 0.050 | 2.969 |
| 96277 | 0.087 | −0.035 | 0.000 | 0.000 | 0.000 | 0.000 | 0.000 | 0.000 | −0.070 | 0.000 | 0.027 | 0.000 | 0.015 | 0.046 | 0.034 | −0.040 | 0.050 | 2.973 |
| 116792 | 0.087 | 0.000 | 0.000 | −0.014 | 0.006 | 0.000 | 0.000 | 0.000 | −0.070 | −0.026 | 0.027 | 0.000 | 0.015 | 0.046 | 0.034 | −0.040 | 0.050 | 2.974 |
| 112293 | 0.087 | −0.035 | 0.000 | 0.000 | 0.000 | 0.000 | 0.000 | 0.000 | −0.070 | −0.026 | 0.027 | −0.023 | 0.015 | 0.046 | 0.034 | −0.040 | 0.050 | 2.978 |
| 124386 | 0.087 | −0.035 | 0.000 | −0.014 | 0.006 | 0.000 | 0.000 | 0.000 | −0.070 | −0.026 | 0.027 | −0.023 | 0.015 | 0.046 | 0.034 | −0.040 | 0.050 | 2.997 |
| 129078 | 0.087 | −0.035 | 0.009 | 0.000 | 0.000 | 0.000 | 0.000 | 0.000 | −0.070 | −0.026 | 0.027 | 0.000 | 0.015 | 0.046 | 0.034 | −0.040 | 0.050 | 3.003 |
| 114075 | 0.087 | −0.035 | 0.000 | 0.000 | 0.006 | 0.000 | 0.000 | 0.000 | −0.070 | −0.026 | 0.027 | −0.023 | 0.015 | 0.046 | 0.034 | −0.040 | 0.050 | 3.015 |
| 123448 | 0.087 | −0.035 | 0.000 | 0.000 | 0.006 | 0.000 | 0.000 | 0.000 | −0.070 | −0.026 | 0.027 | −0.023 | 0.015 | 0.046 | 0.034 | −0.040 | 0.050 | 3.015 |
| 28791 | 0.087 | 0.000 | 0.000 | 0.000 | 0.006 | 0.000 | 0.000 | 0.000 | −0.070 | −0.026 | 0.000 | 0.000 | 0.015 | 0.046 | 0.034 | 0.000 | 0.000 | 3.018 |
| 71961 | 0.087 | −0.035 | 0.000 | 0.000 | 0.000 | 0.000 | 0.000 | 0.000 | −0.070 | −0.026 | 0.027 | −0.023 | 0.015 | 0.046 | 0.034 | −0.040 | 0.050 | 3.019 |
| 130457 | 0.087 | −0.035 | 0.009 | −0.014 | 0.006 | 0.000 | 0.000 | 0.000 | −0.070 | −0.026 | 0.027 | 0.000 | 0.015 | 0.046 | 0.034 | −0.040 | 0.050 | 3.037 |
| 124163 | 0.087 | −0.035 | 0.000 | −0.014 | 0.000 | 0.000 | 0.000 | 0.000 | −0.070 | −0.026 | 0.027 | −0.023 | 0.015 | 0.046 | 0.034 | −0.040 | 0.050 | 3.041 |
| 128572 | 0.087 | −0.035 | 0.000 | −0.014 | 0.000 | 0.000 | 0.000 | 0.000 | −0.070 | −0.026 | 0.027 | 0.000 | 0.015 | 0.046 | 0.034 | −0.040 | 0.050 | 3.046 |
| 128349 | 0.087 | −0.035 | 0.009 | −0.014 | 0.006 | 0.000 | 0.000 | 0.000 | −0.070 | −0.026 | 0.027 | 0.000 | 0.015 | 0.046 | 0.034 | −0.040 | 0.050 | 3.049 |
| 24694 | 0.087 | −0.035 | 0.000 | 0.000 | 0.000 | 0.000 | 0.000 | 0.000 | −0.070 | 0.000 | 0.000 | 0.000 | 0.000 | 0.046 | 0.034 | 0.000 | 0.000 | 3.089 |
| 94844 | 0.087 | −0.035 | 0.000 | −0.014 | 0.006 | 0.000 | 0.000 | 0.000 | −0.070 | 0.000 | 0.027 | −0.023 | 0.000 | 0.046 | 0.034 | −0.040 | 0.050 | 3.151 |
| 110860 | 0.087 | −0.035 | 0.009 | −0.014 | 0.000 | 0.000 | 0.028 | 0.000 | −0.070 | 0.000 | 0.000 | −0.023 | 0.000 | 0.046 | 0.034 | −0.040 | 0.050 | 3.187 |
| 122312 | 0.087 | −0.035 | 0.009 | −0.014 | 0.006 | 0.000 | 0.028 | 0.000 | −0.070 | 0.000 | 0.000 | −0.023 | 0.000 | 0.046 | 0.034 | −0.040 | 0.050 | 3.192 |
| 112939 | 0.087 | −0.035 | 0.000 | −0.014 | 0.006 | 0.000 | 0.028 | 0.000 | −0.070 | 0.000 | 0.000 | −0.023 | 0.000 | 0.046 | 0.034 | −0.040 | 0.050 | 3.197 |

TABLE R1

The Functionally-Defined LSC17 Score vs. the Jung et al. Score

| | Overall Survival | | | |
|---|---|---|---|---|
| | GSE12417 CN-AML Cohort 1 Univariate Analysis (n = 156)* | | TCGA AML Univariate Analysis (n = 183)* | |
| Covariate | Hazard Ratio (95% CI)† | P-value‡ | Hazard Ratio (95% CI)† | P-value‡ |
| Jung et al. Score | 2.35 (1.56-3.54) | <0.001 | 2.02 (1.42-2.87) | <0.001 |
| | GSE12417 CN-AML Cohort 1 Multivariate Analysis 1 | | TCGA AML Multivariate Analysis 1 | |
| Covariate | Hazard Ratio (95% CI)† | P-value‡ | Hazard Ratio (95% CI)† | P-value‡ |
| Jung et al. Score | 1.65 (1.05-2.58) | 0.02 | 1.86 (1.01-3.43) | 0.04 |
| Age | 1.02 (1.01-1.04) | 0.002 | Stratifier§ | N/A |
| WBC count | 1.00 (1.00-1.00) | 0.51 | 1.01 (1.00-1.01) | 0.004 |
| Favorable Cytogenetics | N/A | N/A | 0.58 (0.29-1.16) | 0.12 |
| Adverse Cytogenetics | N/A | N/A | 1.52 (0.79-2.89) | 0.20 |
| Secondary/t-AML | 1.39 (0.61-3.21) | 0.42 | N/A | N/A |
| FLT3-ITD Mutation | 2.13 (1.32-3.42) | 0.001 | N/A | N/A |
| NPM1 Mutation | 0.81 (0.53-1.23) | 0.33 | N/A | N/A |
| | GSE12417 CN-AML Cohort 1 Multivariate Analysis 2 (P = 0.001)¶ | | TCGA AML Multivariate Analysis 2 (P = 0.01)¶ | |
| Covariate | Hazard Ratio (95% CI)† | P-value‡ | Hazard Ratio (95% CI)† | P-value‡ |
| LSC17 Score | 2.30 (1.38-3.85) | 0.001 | 2.25 (1.17-4.29) | 0.01 |
| Jung et al. Score | 1.14 (0.69-1.88) | 0.59 | 1.37 (0.70-2.67) | 0.35 |
| Age | 1.02 (1.00-1.04) | 0.01 | Stratifier§ | N/A |
| WBC count | 1.00 (1.00-1.00) | 0.84 | 1.01 (1.00-1.01) | 0.003 |
| Favorable Cytogenetics | N/A | N/A | 0.71 (0.34-1.46) | 0.35 |
| Adverse Cytogenetics | N/A | N/A | 1.41 (0.73-2.74) | 0.30 |
| Secondary/t-AML | 1.48 (0.64-3.40) | 0.35 | N/A | N/A |
| FLT3-ITD Mutation | 1.82 (1.11-2.97) | 0.01 | N/A | N/A |
| NPM1 Mutation | 0.73 (0.47-1.12) | 0.15 | N/A | N/A |

*No. of patients with full clinical annotations are shown.
†The 95% confidence interval is displayed for each hazard ratio calculated by means of multivariate Cox regression analysis.
‡P value was calculated by means of the Wald test.
§Age was used as a stratifying variable in multivariate Cox regression analysis since this parameter (as a covariate) was determined to be violating the proportional hazards assumption by examining its Schoenfeld residuals. Using Age as a stratification parameter corrected the problem.
¶Inclusion of the LSC17 scores in multivariate model 2 significantly improves predictions of patient outcomes compared to multivariate model 1. P value was calculated by means of the likelihood ratio test.

TABLE R2

The Functionally-Defined LSC17 Score vs. the Gentles et al. Score

| | Overall Survival | | | |
|---|---|---|---|---|
| | GSE12417 CN-AML Cohort 1 Univariate Analysis (n = 156)* | | TCGA AML Univariate Analysis (n = 183)* | |
| Covariate | Hazard Ratio (95% CI)† | P-value‡ | Hazard Ratio (95% CI)† | P-value‡ |
| Gentles et al. Score | 2.15 (1.43-3.22) | <0.001 | 1.68 (1.18-2.38) | 0.003 |
| | GSE12417 CN-AML Cohort 1 Multivariate Analysis 1 | | TCGA AML Multivariate Analysis 1 | |
| Covariate | Hazard Ratio (95% CI)† | P-value‡ | Hazard Ratio (95% CI)† | P-value‡ |
| Gentles et al. Score | 1.76 (1.14-2.69) | 0.009 | 1.72 (1.01-2.93) | 0.04 |
| Age | 1.02 (1.01-1.04) | <0.001 | Stratifier§ | N/A |
| WBC count | 1.00 (1.00-1.00) | 0.53 | 1.00 (1.00-1.01) | 0.006 |
| Favorable Cytogenetics | N/A | N/A | 0.54 (0.27-1.09) | 0.08 |
| Adverse Cytogenetics | N/A | N/A | 1.55 (0.82-2.92) | 0.17 |

TABLE R2-continued

The Functionally-Defined LSC17 Score vs. the Gentles et al. Score

| | | | | |
|---|---|---|---|---|
| Secondary/t-AML | 1.50 (0.65-3.44) | 0.33 | N/A | N/A |
| FLT3-ITD Mutation | 2.15 (1.36-3.40) | 0.001 | N/A | N/A |
| NPM1 Mutation | 0.80 (0.53-1.22) | 0.30 | N/A | N/A |

| | GSE12417 CN-AML Cohort 1 Multivariate Analysis 2 (P = 0.001)¶ | | TCGA AML Multivariate Analysis 2 (P = 0.009)¶ | |
|---|---|---|---|---|
| Covariate | Hazard Ratio (95% CI)† | P-value‡ | Hazard Ratio (95% CI)† | P-value‡ |
| LSC17 Score | 2.17 (1.31-3.58) | 0.002 | 2.27 (1.21-4.28) | 0.01 |
| Gentles et al. Score | 1.33 (0.83-2.11) | 0.23 | 1.37 (0.79-2.38) | 0.25 |
| Age | 1.02 (1.00-1.04) | 0.008 | Stratifier§ | N/A |
| WBC count | 1.00 (1.00-1.00) | 0.74 | 1.00 (1.00-1.01) | 0.003 |
| Favorable Cytogenetics | N/A | N/A | 0.70 (0.34-1.43) | 0.33 |
| Adverse Cytogenetics | N/A | N/A | 1.41 (0.73-2.71) | 0.29 |
| Secondary/t-AML | 1.49 (0.65-3.41) | 0.34 | N/A | N/A |
| FLT3-ITD Mutation | 1.80 (1.12-2.91) | 0.01 | N/A | N/A |
| NPM1 Mutation | 0.74 (0.48-1.13) | 0.16 | N/A | N/A |

*No. of patients with full clinical annotations are shown.
†The 95% confidence interval is displayed for each hazard ratio calculated by means of multivariate Cox regression analysis.
‡P value was calculated by means of the Wald test.
§Age was used as a stratifying variable in multivariate Cox regression analysis since this parameter (as a covariate) was determined to be violating the proportional hazards assumption by examining its Schoenfeld residuals. Using Age as a stratification parameter corrected the problem.
¶Inclusion of the LSC17 scores in multivariate model 2 significantly improves predictions of patient outcomes compared to multivariate model 1. P value was calculated by means of the likelihood ratio test.

TABLE R3

Predictive Ability of Multivariate Logistic Regression Models for Failure to Achieve Initial CR

| PM AML (n = 96)* | Model 1a | | Model 2a (P = 0.09)¶ | | Model 3a (P = 0.002)¶ | |
|---|---|---|---|---|---|---|
| Covariate | Odds Ratio (95% CI)† | P-value‡ | Odds Ratio (95% CI)† | P-value‡ | Odds Ratio (95% CI)† | P-value‡ |
| LSC17 Score§ | Not included in model | N/A | Not included in model | N/A | 1.99 (1.15-3.46) | 0.01 |
| Age | 1.09 (1.01-1.16) | 0.01 | 1.10 (1.02-1.19) | 0.009 | 1.09 (0.99-1.19) | 0.06 |
| WBC count | 1.00 (0.99-1.01) | 0.71 | 1.00 (0.99-1.01) | 0.20 | 1.01 (1.00-1.03) | 0.01 |
| Secondary/t-AML | 3.12 (0.61-15.8) | 0.17 | 1.77 (0.30-10.2) | 0.52 | 4.28 (0.61-29.7) | 0.14 |
| NPM1 Mutation | Not included in model | N/A | 0.18 (0.03-1.11) | 0.06 | 0.34 (0.04-2.76) | 0.31 |
| FLT3-ITD Mutation | Not included in model | N/A | 0.61 (0.09-3.83) | 0.60 | 0.40 (0.05-3.06) | 0.37 |
| AUROC | 72.8 | | 76.7 | | 82.6 | |

| PM AML (n = 283)* | Model 1b | | Model 2b (P < 0.001)¶ | | Model 3b (P < 0.001)¶ | |
|---|---|---|---|---|---|---|
| Covariate | Odds Ratio (95% CI)† | P-value‡ | Odds Ratio (95% CI)† | P-value‡ | Odds Ratio (95% CI)† | P-value‡ |
| LSC17 Score§ | Not included in model | N/A | Not included in model | N/A | 1.46 (1.27-1.68) | <0.001 |
| Age | 0.99 (0.97-1.01) | 0.64 | 0.99 (0.97-1.01) | 0.36 | 0.98 (0.95-1.00) | 0.07 |
| WBC count | 1.00 (0.99-1.00) | 0.36 | 1.00 (0.99-1.00) | 0.21 | 1.00 (1.00-1.01) | 0.004 |
| Secondary/t-AML | 2.84 (1.34-6.03) | 0.006 | 2.77 (1.21-6.30) | 0.01 | 2.50 (1.01-6.18) | 0.04 |
| Favorable Cytogenetics | Not included in model | N/A | 0.14 (0.03-0.61) | 0.009 | 0.20 (0.04-0.91) | 0.03 |
| Adverse Cytogenetics | Not included in model | N/A | 6.17 (2.89-13.1) | <0.001 | 2.87 (1.25-6.61) | 0.01 |
| AUROC | 51.6 | | 73.1 | | 81.6 | |

| PM CN-AML (n = 85)* | Model 1c | | Model 2c (P = 0.03)¶ | | Model 3c (P = 0.01)¶ | |
|---|---|---|---|---|---|---|
| Covariate | Odds Ratio (95% CI)† | P-value‡ | Odds Ratio (95% CI)† | P-value‡ | Odds Ratio (95% CI)† | P-value‡ |
| LSC17 Score§ | Not included in model | N/A | Not included in model | N/A | 1.80 (1.02-3.20) | 0.04 |
| Age | 1.09 (1.01-1.18) | 0.02 | 1.12 (1.02-1.23) | 0.01 | 1.10 (0.99-1.23) | 0.06 |
| WBC count | 1.00 (0.99-1.01) | 0.51 | 1.01 (0.99-1.02) | 0.09 | 1.02 (1.00-1.04) | 0.02 |
| Secondary/t-AML | 3.80 (0.70-20.5) | 0.12 | 1.74 (0.26-11.4) | 0.56 | 3.81 (0.47-30.6) | 0.20 |
| NPM1 Mutation | Not included in model | N/A | 0.08 (0.006-0.99) | 0.05 | 0.13 (0.007-2.37) | 0.16 |
| FLT3-ITD Mutation | Not included in model | N/A | 0.48 (0.04-5.08) | 0.54 | 0.37 (0.03-4.46) | 0.43 |
| AUROC | 74.1 | | 79.1 | | 83.9 | |

TABLE R3-continued

Predictive Ability of Multivariate Logistic Regression Models for Failure to Achieve Initial CR

| PM AML Testing Set (n = 137)* | Model 1d | | Model 2d (P < 0.001)¶ | | Model 3d (P < 0.001)¶ | |
|---|---|---|---|---|---|---|
| Covariate | Odds Ratio (95% CI)† | P-value‡ | Odds Ratio (95% CI)† | P-value‡ | Odds Ratio (95% CI)† | P-value‡ |
| Response Score§ | Not included in model | N/A | Not included in model | N/A | 1.50 (1.23-1.83) | <0.001 |
| Age | 1.00 (0.97-1.03) | 0.69 | 1.00 (0.97-1.03) | 0.95 | 1.00 (0.96-1.03) | 0.95 |
| WBC count | 1.00 (0.99-1.00) | 0.97 | 1.00 (0.99-1.01) | 0.32 | 1.00 (0.99-1.01) | 0.18 |
| Secondary/t-AML | 1.69 (0.49-5.75) | 0.40 | 1.83 (0.47-7.06) | 0.37 | 1.30 (0.30-5.65) | 0.72 |
| Favorable Cytogenetics | Not included in model | N/A | Not included in model** | N/A | Not included in model** | N/A |
| Adverse Cytogenetics | Not included in model | N/A | 14.8 (4.26-51.9) | <0.001 | 5.83 (1.55-21.9) | 0.009 |
| AUROC | 49.7 | | 64.9 | | 81.0 | |

‡P value was calculated by means of the Wald test.
*No. of patients with full clinical annotations are shown.
†The 95% confidence interval is displayed for each hazard ratio calculated by means of multivariate Cox regression analysis.
¶Inclusion of additional covariates in successive multivariate models significantly improves predictions of therapy resistance compared to immediately preceding multivariate models. P value was calculated by means of the likelihood ratio test.
§raw LSC scores were binned into deciles.
**Favorable cytogenetic risk was not included in the model due to collinearity.

TABLE R4

Raw Continuous LSC17 Scores are Strongly Associated With OS

| | Overall Survival | | | |
|---|---|---|---|---|
| | PM AML (n = 307)* | | PM CN-AML (n = 141)* | |
| Covariate | Hazard Ratio (95% CI)† | P-value‡ | Hazard Ratio (95% CI)† | P-value‡ |
| Raw LSC17 Scores | 4.85 (3.01-7.82) | <0.001 | 9.07 (3.95-20.8) | <0.001 |

| | PM AML (n = 284)* | | PM CN-AML (n = 85)* | |
|---|---|---|---|---|
| Covariate | Hazard Ratio (95% CI)† | P-value‡ | Hazard Ratio (95% CI)† | P-value‡ |
| Raw LSC17 Scores | 4.30 (2.39-7.72) | <0.001 | 7.77 (1.92-31.4) | 0.004 |
| Age | 1.00 (0.99-1.01) | 0.15 | 1.00 (0.98-1.03) | 0.74 |
| WBC count | 1.00 (1.00-1.00) | 0.002 | 1.00 (1.00-1.01) | 0.02 |
| NPM1 Mutation | Not included in model | N/A | 0.46 (0.23-0.95) | 0.03 |
| FLT3-ITD Mutation | Not included in model | N/A | 1.88 (0.92-3.84) | 0.08 |
| Favorable Cytogenetics | 0.46 (0.27-0.81) | 0.006 | Not included in model | N/A |
| Adverse Cytogenetics | 1.98 (1.33-2.95) | <0.001 | Not included in model | N/A |
| Secondary/t-AML | 2.18 (1.47-3.23) | <0.001 | 2.94 (1.29-6.71) | 0.01 | t-AML, therapy-associated AML
*No. of patients with full clinical annotations are shown.
†The 95% confidence interval is displayed for each hazard ratio calculated by means of multivariate Cox regression analysis.
‡P value was calculated by means of the Wald test.
§Age was used as a stratifying variable in multivariate Cox regression analysis since this parameter (as a covariate) was determined to be violating the proportional hazards assumption by examining its Schoenfeld residuals. Using Age as a stratification parameter corrected the problem.

TABLE R5

Multivariate Analysis of OS in Patient Subsets Defined by LSC17 Score and Allo-SCT in the PM AML Cohort

| | Overall Survival | | | |
|---|---|---|---|---|
| | Allo-SCT (n = 79)* | | No Allo-SCT (n = 283)* | |
| Covariate | Hazard Ratio (95% CI)† | P-value‡ | Hazard Ratio (95% CI)† | P-value‡ |
| LSC17 Score | 2.00 (1.02-3.91) | 0.04 | 2.63 (1.77-3.91) | <0.001 |
| Age | Stratifier§ | N/A | 1.01 (1.00-1.02) | 0.04 |
| WBC count | 1.00 (0.99-1.00) | 0.41 | 1.00 (1.00-1.00) | 0.02 |
| Favorable Cytogenetics | 0.93 (0.31-2.72) | 0.89 | 0.42 (0.22-0.82) | 0.01 |

TABLE R5-continued

Multivariate Analysis of OS in Patient Subsets Defined by LSC17 Score and Allo-SCT in the PM AML Cohort

| | Overall Survival | | | |
|---|---|---|---|---|
| | Allo-SCT (n = 79)* | | No Allo-SCT (n = 283)* | |
| Covariate | Hazard Ratio (95% CI)† | P-value‡ | Hazard Ratio (95% CI)† | P-value‡ |
| Adverse Cytogenetics | 0.96 (0.40-2.34) | 0.94 | 2.47 (1.57-3.87) | <0.001 |
| Secondary/t-AML | 0.82 (0.23-2.83) | 0.75 | 2.71 (1.77-4.15) | <0.001 |

*No. of patients with full clinical annotations are shown.
†The 95% confidence interval is displayed for each hazard ratio calculated by means of multivariate Anderson-Gill analysis.
‡P value was calculated by means of the Wald test.
§Age was used as a stratifying variable in multivariate Cox regression analysis since this parameter (as a covariate) was determined to be violating the proportional hazards assumption by examining its Schoenfeld residuals. Using Age as a stratification parameter corrected the problem.
t-AML, therapy-associated AML

TABLE R6

Multivariate Competing Risks Regression in Patient Subsets Defined by LSC17 Score and Allo-SCT in the PM AML Cohort

| | Cumulative Incidence of Relapse No Allo-SCT (n = 199)* | |
|---|---|---|
| Covariate | Sub-distribution Hazard Ratio (95% CI)† | P-value‡ |
| LSC17 Score | 1.85 (1.23-2.78) | 0.003 |
| Age | 0.99 (0.98-1.01) | 0.80 |
| WBC count | 1.00 (0.99-1.00) | 0.33 |
| Favorable Cytogenetics | 0.45 (0.24-0.83) | 0.01 |
| Adverse Cytogenetics | 2.06 (1.25-3.38) | 0.004 |
| Secondary/t-AML | 1.91 (0.88-4.13) | 0.10 |

*No. of patients with full clinical annotations are shown.
†The 95% confidence interval is displayed for each SHR calculated by means of Fine-Gray competing risks regression analysis.
‡P value was calculated by means of Gray's test.
t-AML, therapy-associated AML

TABLE R7

Association of Gene Mutations with LSC17

| Characteristic | TCGA AML cohort (n = 183) | High LSC17 score subset (n = 92) | Low LSC17 score subset (n = 91) | P-value∥ |
|---|---|---|---|---|
| MYH11-CBFB [n (%)] | | | | |
| MYH11-CBFB positive | 10 (5.46) | 1 (1.08) | 9 (9.89) | 0.009 |
| MYH11-CBFB negative | 173 (94.5) | 91 (98.9) | 82 (90.1) | |
| RUNX1-RUNX1T1 [n (%)] | | | | |
| RUNX1-RUNX1T1 positive | 7 (3.82) | 0 (0.00) | 7 (7.69) | 0.006 |
| RUNX1-RUNX1T1 negative | 176 (96.1) | 92 (100.0) | 84 (92.3) | |
| RUNX1 [n (%)] | | | | |
| RUNX1 mutation | 17 (9.29) | 15 (16.3) | 2 (2.19) | 0.001 |
| No RUNX1 mutation | 166 (90.7) | 77 (83.7) | 89 (97.8) | |
| TP53 [n (%)] | | | | |
| TP53 mutation | 16 (8.74) | 15 (16.3) | 1 (1.09) | <0.001 |
| No TP53 mutation | 167 (91.2) | 77 (83.7) | 90 (98.9) | |
| Characteristic | PM AML cohort (n = 61) | High LSC17 score subset (n = 31) | Low LSC17 score subset (n = 30) | P-value∥ |
| IDH1 [n (%)]* | | | | |
| IDH1 mutation | 9 (14.7) | 8 (25.8) | 1 (3.33) | 0.02 |
| No IDH1 mutation | 52 (85.2) | 23 (74.2) | 29 (96.6) | |
| CN AML- CEBPA [n (%)] | (n = 49) | (n = 25) | (n = 24) | |

TABLE R7-continued

Association of Gene Mutations with LSC17

| | | | | |
|---|---|---|---|---|
| CEBPA mutation | 8 (16.3) | 1 (4.00) | 7 (29.2) | 0.02 |
| No CEBPA mutation | 41 (83.6) | 24 (96.0) | 17 (70.8) | |

‖P-values calculated using Fisher's exact test
*Similar results were found for the CN-AML subset

TABLE R8

Multivariate Analysis of LSC17 Association with OS When Accounting for Prognostic Gene Mutations

TCGA AML (n = 183)*

| Covariate | Multivariate Analysis 1 | | Multivariate Analysis 2 (P < 0.001)¶ | |
|---|---|---|---|---|
| | Hazard Ratio (95% CI)† | P-value‡ | Hazard Ratio (95% CI)† | P-value‡ |
| LSC17 Score | Not included in model | N/A | 3.08 (1.56-6.06) | 0.001 |
| PML-RARA Mutation | 0.43 (0.10-1.74) | 0.23 | 0.34 (0.08-1.47) | 0.15 |
| MYH11-CBFB Mutation | 0.40 (0.08-1.96) | 0.26 | 0.27 (0.05-1.38) | 0.11 |
| FLT3 in-frame Mutation | 4.78 (0.73-31.3) | 0.10 | 7.75 (0.90-66.2) | 0.06 |
| DNMT3A Mutation | 1.74 (0.95-3.17) | 0.07 | 1.92 (1.02-3.58) | 0.04 |
| RUNX1 Mutation | 1.44 (0.66-3.17) | 0.35 | 1.08 (0.48-2.45) | 0.84 |
| TP53 Mutation | 2.30 (0.92-5.71) | 0.07 | 1.71 (0.66-4.38) | 0.26 |
| Age | Stratifier§ | N/A | Stratifier§ | N/A |
| WBC count | 1.00 (1.00-1.01) | 0.006 | 1.01 (1.00-1.01) | 0.005 |
| Favorable Cytogenetics | 1.32 (0.43-4.06) | 0.62 | 2.33 (0.68-7.92) | 0.17 |
| Adverse Cytogenetics | 1.61 (0.78-3.31) | 0.19 | 1.40 (0.65-3.02) | 0.39 |

PM AML (n = 54)*

| Covariate | Multivariate Analysis 3 | | Multivariate Analysis 4 (P = 0.005)¶ | |
|---|---|---|---|---|
| | Hazard Ratio (95% CI)† | P-value‡ | Hazard Ratio (95% CI)† | P-value‡ |
| LSC17 Score | Not included in model | N/A | 4.12 (1.46-11.6) | 0.007 |
| ASXL1 Mutation | 3.09 (0.75-12.6) | 0.11 | 2.13 (0.56-7.99) | 0.26 |
| IDH1 Mutation | 3.68 (1.36-9.98) | 0.01 | 2.15 (0.74-6.22) | 0.15 |
| NRAS Mutation | 0.27 (0.09-0.81) | 0.02 | 0.30 (0.10-0.91) | 0.03 |
| Age | 0.99 (0.96-1.02) | 0.69 | 0.99 (0.96-1.02) | 0.69 |
| WBC Count | 0.99 (0.98-1.00) | 0.39 | 1.00 (0.99-1.01) | 0.68 |
| Favorable Cytogenetics | Not included in model** | N/A | Not included in model** | N/A |
| Adverse Cytogenetics | Not included in model** | N/A | Not included in model** | N/A |
| Secondary/t-AML | 3.96 (1.15-13.6) | 0.03 | 6.13 (1.85-20.3) | 0.003 |

PM CN-AML (n = 49)*

| Covariate | Multivariate Analysis 5 | | Multivariate Analysis 6 (P = 0.001)¶ | |
|---|---|---|---|---|
| | Hazard Ratio (95% CI)† | P-value‡ | Hazard Ratio (95% CI)† | P-value‡ |
| LSC17 Score | Not included in model | N/A | 7.06 (1.95-25.6) | 0.003 |
| ASXL1 Mutation | 2.57 (0.46-14.1) | 0.27 | 2.80 (0.49-16.0) | 0.24 |
| IDH1 Mutation | 5.66 (1.88-17.0) | 0.002 | 2.48 (0.72-8.57) | 0.14 |
| NRAS Mutation | 0.30 (0.10-0.93) | 0.03 | 0.35 (0.11-1.06) | 0.06 |
| Age | 0.98 (0.94-1.01) | 0.31 | 0.99 (0.95-1.02) | 0.56 |
| WBC Count | 0.99 (0.98-1.00) | 0.56 | 1.00 (0.99-1.01) | 0.23 |
| Secondary/t-AML | 6.37 (1.46-27.8) | 0.01 | 8.56 (1.84-39.7) | 0.006 |

*No. of patients with full clinical annotations are shown.
†The 95% confidence interval is displayed for each hazard ratio calculated by means of multivariate Cox regression analysis.
‡P value was calculated by means of the Wald test.
§Age was used as a stratifying variable in multivariate Cox regression analysis since this parameter (as a covariate) was determined to be violating the proportional hazards assumption by examining its Schoenfeld residuals. Using Age as a stratification parameter corrected the problem.
¶Inclusion of the LSC17 scores in multivariate models 2, 4, and 6 significantly improves association with patient outcomes compared to multivariate models 1, 3, and 5, respectively. P value was calculated by means of the likelihood ratio test.
**Cytogenetic risk was not included in the model due to insufficient data (n = 1).

TABLE N1

The Functionally-Defined LSC17 Score Remains Significant After Adjusting for the Papaemmanuil et al. Genomics Classification Scheme Overall Survival TCGA AML (n = 183)*

| Covariate | Multivariate Analysis 1 Hazard Ratio (95% CI)† | P-value‡ | Multivariate Analysis 2 (P < 0.001)¶ Hazard Ratio (95% CI)† | P-value‡ |
|---|---|---|---|---|
| High LSC17 score | Not included in model | N/A | 2.29 (1.52-3.45) | <0.001 |
| CEBPA$^{biallelic}$ | 1.61 (0.40-6.46) | 0.49 | 2.15 (0.53-8.72) | 0.28 |
| Chromatin-spliceosome | 4.22 (1.73-10.3) | 0.001 | 2.94 (1.18-7.28) | 0.02 |
| IDH2$^{R172}$‖ | <0.001 (0.00-inf) | 0.99 | 4.19 (0.00-inf) | 0.99 |
| inv(16) | 1.15 (0.32-4.11) | 0.82 | 1.50 (0.41-5.39) | 0.53 |
| MLL fusion | 2.65 (0.85-8.28) | 0.09 | 2.48 (0.79-7.76) | 0.11 |
| No class-defining drivers | 3.29 (1.31-8.24) | 0.01 | 3.34 (1.33-8.38) | 0.01 |
| No driver mutations | 1.24 (0.25-6.17) | 0.79 | 1.02 (0.20-5.08) | 0.98 |
| NPM1 mutation | 3.04 (1.27-7.28) | 0.01 | 2.75 (1.14-6.62) | 0.02 |
| t(8; 21) | 1.41 (0.35-5.67) | 0.63 | 1.87 (0.45-7.63) | 0.38 |
| TP53-aneuploidy | 4.78 (1.94-11.7) | <0.001 | 3.42 (1.37-8.56) | 0.008 |
| 2+ classes | 3.84 (0.95-15.4) | 0.05 | 3.37 (0.83-13.6) | 0.08 |

| Covariate | Multivariate Analysis 3 Hazard Ratio (95% CI)† | P-value‡ | Multivariate Analysis 4 (P = 0.001)¶ Hazard Ratio (95% CI)† | P-value‡ |
|---|---|---|---|---|
| High LSC17 score | Not included in model | N/A | 2.85 (1.47-5.52) | 0.002 |
| Age | Stratifier§ | N/A | Stratifier§ | N/A |
| WBC count | 1.00 (1.00-1.01) | 0.02 | 1.00 (1.00-1.01) | 0.01 |
| CEBPA$^{biallelic}$ | 0.86 (0.11-6.57) | 0.89 | 1.45 (0.18-11.5) | 0.72 |
| Chromatin-spliceosome | 1.80 (0.54-5.98) | 0.33 | 1.00 (0.28-3.54) | 0.99 |
| IDH2$^{R172}$ | <0.001 (0.00-inf) | 0.99 | <0.001 (0.00-inf) | 0.99 |
| inv(16) | 1.08 (0.23-5.03) | 0.91 | 0.82 (0.17-3.85) | 0.80 |
| MLL fusion | 2.19 (0.51-9.35) | 0.28 | 1.77 (0.39-7.89) | 0.45 |
| No class-defining drivers | 2.19 (0.60-7.98) | 0.23 | 1.54 (0.40-5.87) | 0.52 |
| No driver mutations | 1.20 (0.16-8.60) | 0.85 | 0.71 (0.09-5.34) | 0.74 |
| NPM1 mutation | 2.21 (0.70-6.93) | 0.17 | 1.65 (0.51-5.30) | 0.39 |
| t(8; 21) | 1.52 (0.21-10.8) | 0.67 | 2.22 (0.29-16.5) | 0.43 |
| TP53-aneuploidy | 4.53 (1.34-15.3) | 0.01 | 2.12 (0.58-7.73) | 0.25 |
| 2+ classes | 3.26 (0.48-21.9) | 0.22 | 1.70 (0.24-11.8) | 0.59 |

*No. of patients with full clinical annotations are shown.
†The 95% confidence interval is displayed for each hazard ratio calculated by means of multivariate Cox regression analysis.
‡P value was calculated by means of the Wald test.
§Age was used as a stratifying variable in multivariate Cox regression analysis since this parameter (as a covariate) was determined to be violating the proportional hazards assumption by examining its Schoenfeld residuals. Using Age as a stratification parameter corrected the problem.
¶Inclusion of LSC17 scores in multivariate model 2 and 4 significantly improves predictions of patient outcomes compared to multivariate model 1 and 3, respectively. P value was calculated by means of the likelihood ratio test.
‖There was only n = 1 case in this category
Additional Notes:
Genomic classes are compared to t(15; 17) in all CPH models. There were no t(6; 9) cases in the TCGA cohort. All inv(3) cases in the TCGA cohort are included in the 2+ classes category.

TABLE N2

The LSC17 Score Refines the Papaemmanuil et al. Genomics Classification Scheme

Overall Survival TCGA AML (n = 33)*

| Covariate | Multivariate Analysis 1 Hazard Ratio (95% CI)† | P-value‡ | Multivariate Analysis 2 (P = 0.001)¶ Hazard Ratio (95% CI)† | P-value‡ |
|---|---|---|---|---|
| High LSC17 score | Not included in model | N/A | 3.97 (1.72-9.13) | 0.001 |
| No driver mutations** | 0.39 (0.09-1.71) | 0.21 | 0.28 (0.06-1.23) | 0.09 |
| 2+ classes** | 1.08 (0.32-3.68) | 0.89 | 0.97 (0.28-3.32) | 0.96 |

TABLE N2-continued

The LSC17 Score Refines the Papaemmanuil et al. Genomics Classification Scheme

| Covariate | Multivariate Analysis 3 Hazard Ratio (95% CI)† | P-value‡ | Multivariate Analysis 4 (P = 0.01)¶ Hazard Ratio (95% CI)† | P-value‡ |
|---|---|---|---|---|
| High LSC17 score | Not included in model | N/A | 3.33 (1.30-8.51) | 0.01 |
| Age | 1.05 (1.02-1.09) | <0.001 | 1.04 (1.01-1.08) | 0.006 |
| WBC count | 1.01 (1.00-1.02) | 0.02 | 1.01 (1.00-1.02) | 0.006 |
| No driver mutations** | 0.54 (0.12-2.41) | 0.42 | 0.34 (0.07-1.53) | 0.16 |
| 2+ classes** | 1.84 (0.51-6.61) | 0.34 | 1.19 (0.32-4.37) | 0.78 |

*No. of patients with full clinical annotations are shown.
**The No Class Drivers risk group from Papaemmanuil et al. was used as a reference to compare to.
†The 95% confidence interval is displayed for each hazard ratio calculated by means of multivariate Cox regression analysis.
‡P value was calculated by means of the Wald test.
¶Inclusion of LSC17 scores in multivariate model 2 significantly improves predictions of patient outcomes compared to multivariate model 1. P value was calculated by means of the likelihood ratio test.
Additional Notes:
Genomic classes are compared to the no class-defining drivers category in all CPH models. Median of the full TCGA cohort was used to discretize raw LSC17 scores.

TABLE N3

The Effect of Gemtuzumab Ozogamicin on EFS and RFS in Patients With Low LSC17 Scores ALFA-0701 Low LSC17 Score Subset

| Covariate | Event-Free Survival (n = 90)* Hazard Ratio (95% CI)† | P-value‡ | Relapse-Free Survival (n = 80)* Hazard Ratio (95% CI)† | P-value‡ |
|---|---|---|---|---|
| GO vs. Standard Treatment | 0.34 (0.19-0.63) | <0.001 | 0.42 (0.21-0.83) | 0.01 |
| Age | 1.04 (0.99-1.10) | 0.09 | 1.03 (0.97-1.09) | 0.31 |
| WBC count | 1.00 (0.99-1.01) | 0.11 | 1.00 (0.99-1.01) | 0.10 |
| Favorable Cytogenetics | 1.29 (0.39-4.23) | 0.66 | 1.26 (0.30-5.31) | 0.75 |
| Adverse Cytogenetics | 1.98 (0.82-4.77) | 0.12 | 0.44 (0.06-3.31) | 0.43 |

*No. of patients with full clinical annotations are shown.
†The 95% confidence interval is displayed for each hazard ratio calculated by means of multivariate Cox regression analysis.
‡P value was calculated by means of the Wald test.

TABLE N4

| Gene | Target Sequence |
|---|---|
| AKR1C3 | AGAGGACGTCTCTATGCCGGTGACTGGACATATCACCTCTA CTTAAATCCGTCCTGTTTAGCGACTTCAGTCAACTACAGCT GAGTCCATAGGCCAGAAA (SEQ ID NO: 1) |
| ARHGAP22 | GGAACTCTGAACGGGCGCGGGAGGATGCGGAGAGGAGGAAC CAGCTGTTGCAGAGGGAAATGGAGGAGTTTTTTTCGACCCT AGGAAGCTTGACTGTTGG (SEQ ID NO: 2) |
| C19orf77 | GGCTCTCTGGGCAAACATGGTTTTCATGCACCCCTCTTCCT GAGCTTGGTCCCTGCCTGGTGATTCTTCTTATACTCGGAGA GCATCCCTGGTTGAGGAG (SEQ ID NO: 3) |
| CD34 | ATATGGTCATAGCCCAGATCAGCTCCTAACCCTTATCACCA GCTGCCTCTTCTGTGGGTGACCCAGGTCCTTGTTTGCTGTT GATTTCTTTCCAGAGGGG (SEQ ID NO: 4) |
| CDK6 | AGAAGCAGAACTGTCAGCTTGTGCCTTGAGGCTTCCAGAAC GTGTCAGATGGAGAAGTCCAAGTTTCCATGCTTCAGGCAAC TTAGCTGTGTACAGAAGC (SEQ ID NO: 5) |
| CPXM1 | AGCAGGTGCGCATGGGCATTGCAGGAGTGGTGAGGGACAAG GACACGGAGCTTGGGATTGCTGACGCTGTCATTGCCGTGGA TGGGATTAACCATGACGT (SEQ ID NO: 6) |
| DNMT3B | GGGGTGTGCTGAGTTCTATAATATAAGCTGCCATATATTTT GTAGACAAGTATGGCTCCTCCATATCTCCCTCTTCCCTAGG AGAGGAGTGTGAAGCAAG (SEQ ID NO: 7) |
| DPYSL3 | CCCTGGGCAGCCAGCATTCATTGTAAGTTCCCTCTTTGAAA ACTGGTGTGTGGGTGTTCAGTTCTGTGTCTGGTGGGTATGG ACAGACAGTAATCTCCTG (SEQ ID NO: 8) |
| EMP1 | TCTAGTTAAGGAAATGTTGAGGGCAAGCCACCAAATTACCT AGGCTGAGGTTAGAGAGATTGGCCAGCAAAAACTGTGGGAA GATGAACTTTGTCATTAT (SEQ ID NO: 9) |
| GPR56 | CGCCCTCGGCCGCCCATCATGGTTAATTCTGTCCAACAAAC ACACACGGGTAGATTGCTGGCCTGTTGTAGGTGGTAGGGAC ACAGATGACCGACCTGGT (SEQ ID NO: 10) |
| KIAA0125 | ACAGTTCTGAAGTCAAAGGCTGATGTCCTGTTTCTCTTTCC CTCTGTGACCGACTCCCTTCCCAGTGGTAACAAGTACCCAC AGCTTGGTTTGAATTTCT (SEQ ID NO: 11) |
| LAPTM4B | CCAACTGACTTTATCAAGTGGAATTGGGATATATTTGATAT ACTTCTGCCTAACAACATGGAAAAGGGTTTTCTTTTCCCTG CAAGCTACATCCTACTGC (SEQ ID NO: 12) |

TABLE N4-continued

| Gene | Target Sequence |
|---|---|
| MMRN1 | GCAGACATCCTTTTACTGGTGACAACTGCACTATCAAGCTT GTGGAAGAAAATGCTTTAGCTCCAGATTTTTCCAAAGGATC TTACAGATATGCACCCAT (SEQ ID NO: 13) |
| NGFRAP1 | ACCGAGAAGAGTGACAGGGCTGTGCGCTCTGGGGCACCTCA TGCAGACGGGAGTAGGGAGGCTGTTTTTTGCGCGTGCATAT GGCGGTGGCGGGTGGGGG (SEQ ID NO: 14) |
| NYNRIN | GATTAAGCTTCCTGACTCCCAGTTCACCATGAAAAGGGTTC TGGCAACAGGTTCAAGCTGGAGAATCCTTCAAAATGCTACA CCCACATTCTCTCCAACT (SEQ ID NO: 15) |
| SOCS2 | GAGAGAAAGAACTCCTCATAGGAATACTGAAGAAGTGGGAA GGAACCAAGCTGACACAGGCCTCACTGCAATTTGATATGCC TGCTGATCAGAGTCTCTT (SEQ ID NO: 16) |
| ZBTB46 | TGTATTGGAGATGTGTCTACTATTGGGGAAGAGGTTCTCG TAATCGCTCGGTGGGAAATCATGGCTCTGCCGTCCTGCCTC TCTGTGGCCGTGGGTTCA (SEQ ID NO: 17) |
| EIF4H | CTACACAGCATACGTAGGAAATCTACCTTTCAATACGGTTC AGGGCGACATAGATGCTATCTTTAAGGATCTCAGCATAAGG AGTGTACGGCTAGTCAGA (SEQ ID NO: 18) |
| HNRNPK | GATTGGTGTGCCCGTTTAATAAAAGAATATGGAAACTGAAC AGCCAGAAGAAACCTTCCCTAACACTGAAACCAATGGTGAA TTTGGTAAACGCCCTGCA (SEQ ID NO: 19) |
| HNRNPL | CTCTCTCAATGGGGCTGATATCTATTCTGGCTGTTGCACTC TGAAGATCGAATACGCAAAGCCTACACGCTTGAATGTGTTC AAGAATGATCAGGATACT (SEQ ID NO: 20) |
| PSMA1 | GGTTGCATTGAAAAGGGCGCAATCAGAGCTTGCAGCTCATC AGAAAAAAATTCTCCATGTTGACAACCATATTGGTATCTCA ATTGCGGGGCTTACTGCT (SEQ ID NO: 21) |
| PSMD6 | ATAGGTCATTAACCCTTGGCTATATGGCAGAAGCGTTTGGT GTTGGTGTGGAATTCATTGATCAGGAACTGTCCAGGTTTAT TGCTGCCGGGAGACTACA (SEQ ID NO: 22) |
| SF3B2 | GGACGGAAGTGAGACACCTCAGCTCTTCACTGTGTTGCCAG AGAAGAGAACAGCCACTGTTGGAGGGGCCATGATGGGATCA ACCCACATTTATGACATG (SEQ ID NO: 23) |
| SLC25A3 | TGGTATCTGTGTTGAATAAAGAAAAAGGTAGCAGTGCTTCT CTGGTCCTCAAGAGACTTGGATTTAAAGGTGTATGGAAGGG ACTGTTTGCCCGTATCAT (SEQ ID NO: 24) |
| UBE2I | CGGCCGCCCGAGGGACTTTGAACATGTCGGGGATCGCCCTC AGCAGACTCGCCCAGGAGAGGAAAGCATGGAGGAAAGACCA CCCATTTGGTTTCGTGGC (SEQ ID NO: 25) |
| VPS4A | CAAGCTCTGCCTCAAAGACCGAGTGACATAAGCCATTCCCA CCCTCCTAGGTTCACATCCAGGGCTGTGTCTTCCTTGGGGG AGGAGATGGTGTCGTTTA (SEQ ID NO: 26) |
| GAPDH | CACTCCTCCACCTTTGACGCTGGGGCTGGCATTGCCCTCAA CGACCACTTTGTCAAGCTCATTTCCTGGTATGACAACGAAT TTGGCTACAGCAACAGGG (SEQ ID NO: 27) |
| TBP | ACAGTGAATCTTGGTTGTAAACTTGACCTAAAGACCATTGC ACTTCGTGCCCGAAACGCCGAATATAATCCCAAGCGGTTTG CTGCGGTAATCATGAGGA (SEQ ID NO: 28) |
| ABL1 | CTGCGTGAGCTATGTGGATTCCATCCAGCAAATGAGGAACA AGTTTGCCTTCCGAGAGGCCATCAACAAACTGGAGAATAAT CTCCGGGAGCTTCAGATC (SEQ ID NO: 29) |

The invention claimed is:

1. A method of treating a human subject with acute myeloid leukemia (AML) comprising treating the subject with an aggressive cancer therapy, wherein the subject had been previously identified as being in a high risk group for worse survival by:
   (a) determining the gene expression level (GE level) of the following 17 genes in a test sample from the subject: DNMT3B, ZBTB46, NYNRIN, ARHGAP22, LAPTM4B, MMRN1, DPYSL3, KIAA0125, CDK6, CPXM1, SOCS2, SMIM24, EMP1, NGFRAP1, CD34, AKR1C3, GPR56;
   (b) calculating a leukemia stem cell score (LSC Score) comprising the weighted sum expression of each of the 17 genes; and
   (c) classifying the subject into the high risk group based on a high LSC Score in reference to a control cohort of AML patients.

2. The method of claim 1, wherein determining the GE level comprises use of quantitative PCR or an array.

3. The method of claim 1, wherein determining the GE level comprises use of a digital counting method.

4. The method of claim 1 wherein the more aggressive therapy is intensified chemotherapy or an alternative therapy through enrollment into a clinical trial for a novel therapy.

5. The method of claim 1, wherein the subject is classified into the high risk group based on a LSC Score that is higher than the median score of the control cohort of AML patients.

* * * * *